United States Patent
Araki et al.

(10) Patent No.: US 7,948,247 B2
(45) Date of Patent: May 24, 2011

(54) METAL IDENTIFYING DEVICE AND METAL IDENTIFYING METHOD

(75) Inventors: Norie Araki, Osaka (JP); Hirofumi Iwakawa, Osaka (JP); Yoshiyuki Tani, Osaka (JP); Hiroshi Iwamoto, Osaka (JP)

(73) Assignee: Panasonic Corporation, Osaka (JP)

( * ) Notice: Subject to any disclaimer, the term of this patent is extended or adjusted under 35 U.S.C. 154(b) by 280 days.

(21) Appl. No.: 12/441,290

(22) PCT Filed: Sep. 14, 2007

(86) PCT No.: PCT/JP2007/067980
§ 371 (c)(1),
(2), (4) Date: Mar. 13, 2009

(87) PCT Pub. No.: WO2008/032834
PCT Pub. Date: Mar. 20, 2008

(65) Prior Publication Data
US 2009/0261848 A1    Oct. 22, 2009

(30) Foreign Application Priority Data

| Sep. 14, 2006 | (JP) | 2006-249069 |
| Feb. 5, 2007 | (JP) | 2007-025009 |
| Mar. 26, 2007 | (JP) | 2007-078498 |
| Jul. 4, 2007 | (JP) | 2007-175817 |

(51) Int. Cl.
*G01R 27/08* (2006.01)
*G01N 27/00* (2006.01)

(52) U.S. Cl. ............... 324/705; 324/71.1; 356/313

(58) Field of Classification Search ............. 324/705, 324/71.1; 356/313
See application file for complete search history.

(56) References Cited

U.S. PATENT DOCUMENTS

| 2005/0140974 A1* | 6/2005 | Irie et al. ............. 356/313 |
| 2006/0102831 A1 | 5/2006 | Krauth et al. |
| 2006/0280285 A1 | 12/2006 | Terada |

FOREIGN PATENT DOCUMENTS

| JP | 61-010755 | 1/1986 |
| JP | 7-104026 | 4/1995 |
| JP | 7-318495 | 4/1995 |
| JP | 8-145891 | 6/1996 |
| JP | 8-178843 | 7/1996 |
| JP | 3022585 | 1/2000 |
| JP | 2000-180261 | 6/2000 |
| JP | 2001-242162 | 9/2001 |
| JP | 2002-028789 | 1/2002 |
| JP | 2005-534915 | 11/2005 |
| JP | 2006-53012 | 2/2006 |

* cited by examiner

*Primary Examiner* — Vincent Q Nguyen
(74) *Attorney, Agent, or Firm* — Hamre, Schumann, Mueller & Larson, P.C.

(57) ABSTRACT

A metal identifying device precisely identifies a metal material in a metal member having a plurality of through-hole portions penetrating through the metal member. The metal identifying device of the present invention includes a measurement unit that obtains a measurement value by measuring an electrical property and/or optical property of a test object, a threshold value determination unit that determines a threshold value with use of a reference value obtained by measuring the property of a metal member having a metal composition to be identified and information indicating a ratio of the through-hole portions to a measurement area in the test object and/or information indicating a configuration of the through-hole portion, and a comparison/identification unit that identifies a metal composition of the test object by comparing the measurement value and the threshold value.

18 Claims, 31 Drawing Sheets

METAL IDENTIFYING DEVICE AND METAL IDENTIFYING METHOD

TECHNICAL FIELD

The present invention relates to a metal identifying device and a metal identifying method for identifying the metal composition of a plate-shaped metal member having a plurality of through-hole portions penetrating through the metal member.

BACKGROUND ART

In recent years, from the viewpoint of environmental protection and effective use of resources, there has been a demand for technology for efficiently sorting and reprocessing waste products. The reuse of rare metal resources leads to a reduction in processing cost as well. For this reason, there has been a demand for technology for efficiently reprocessing shadow masks of CRT displays (hereinafter, called a "CRT shadow mask") that are widely used as displays devices in TVs and personal computers. A shadow mask is a metal plate in which small holes are regularly aligned in a honeycomb configuration. In CRT displays, a shadow mask is disposed between an electron gun and phosphor so that when the phosphor is irradiated with a beam from the electron gun, excess portions of the beam are blocked in order to make the pixel pitch smaller. In the process for recycling CRT displays, the shadow mask and support members for the shadow mask are removed from the CRT and recycled as metal resources.

Shadow masks are formed mainly from iron or an Invar alloy that is 64% iron and 36% nickel, which is normally called Invar 36. In recent years, along with increasing screen sizes and the flattening of CRT displays, Invar 36 (hereinafter, called "Invar" or "Invar alloy") has become applied widely to shadow masks due to having little thermal expansion, which is called the Invar property. Since Invar alloy includes nickel, which is valuable, the recovery of shadow masks that are made of Invar alloy is very beneficial in metal resource recycling and the reduction of recycling cost. Therefore, the identification of the metal composition of shadow masks is an important issue in metal recycling. Conventionally, the metal composition of shadow masks has been identified by, for example, human judgment using visual observation, tactile sensation or the like, which requires experience, or by analyzing devices that use X-ray fluorescence or the like, which requires advanced technology and large and expensive equipment.

Examples of the methods for identifying the material of a metal plate such as a vehicular plate include a method of identification by measuring electrical resistance (e.g., Patent Documents 1 and 2), and a method of identification by generating an arc discharge between a discharge electrode and a metal sample and performing spectral analysis on light emitted along with the discharge (e.g., Patent Document 3). Additionally, there is a method of identification by an optical method using a surface coating property of a metal plate product in a conveyor line for metal plate products in a manufacturing process (e.g., Patent Document 4), a method of identification by X-ray fluorescence analysis of a metal such as iron that is contained as an impurity in a thin film on a semiconductor substrate (e.g., Patent Document 5), a method of automatic identification by performing image processing on, among foreign matter contained in a solution, foreign matter that has metallic luster and foreign matter that does not have metallic luster (e.g., Patent Document 6), and a method of identifying a work material based on an absorption spectrum (e.g., Patent Document 7).

Patent document 1: JP 2002-28789A
Patent document 2: JP S61-10755A
Patent document 3: JP H07-318495A
Patent document 4: JP 2005-534915A
Patent document 5: JP 2006-53012A
Patent document 6: JP H08-178843A
Patent document 7: JP 2000-180261A

DISCLOSURE OF INVENTION

Problem to be Solved by the Invention

However, there have not been any devices able simply and precisely to identify the metal composition of a plate-shaped metal member having a plurality of through-hole portions penetrating through the metal member, such as a shadow mask. Also, in the case of identifying a CRT shadow mask by human judgment, the metal composition can only be identified by an experienced person, which is a problem. Furthermore, in the case of human judgment, even with an experienced person, the accuracy of identification is often insufficient since judgment errors occur due to fatigue and the like, and there is often variation between persons.

In view of this situation, an object of the present invention is to provide a metal identifying device and metal identifying method that precisely can identify the metal composition of a plate-shaped metal member having a plurality of through-hole portions penetrating through the metal member.

Means for Solving Problem

A metal identifying device of the present invention includes: a measurement unit that obtains a measurement value by measuring an electrical property and/or an optical property of a test object that is a plate-shaped metal member having a plurality of through-hole portions penetrating through the metal member; a threshold value determination unit that determines a threshold value with use of a reference value obtained by measuring the property of a metal member having a metal composition to be identified, and information indicating a ratio of the through-hole portions to a measurement area in the test object and/or information indicating a configuration of the through-hole portion; and a comparison/identification unit that identifies a metal composition of the test object by comparing the measurement value and the threshold value.

A metal identifying method of the present invention includes the steps of: obtaining a measurement value by measuring an electrical property and/or an optical property of a test object that is a plate-shaped metal member having a plurality of through-hole portions penetrating through the metal member; determining a threshold value with use of a reference value obtained by measuring the property of a metal member having a metal composition to be identified, and information indicating a ratio of the through-hole portions to a measurement area in the test object and/or information indicating a configuration of the through-hole portion; and identifying a metal composition of the test object by comparing the measurement value and the threshold value.

Effects of the Invention

A metal identifying device and metal identifying method of the present invention enable precise identification of the metal composition of a plate-shaped metal member having a plurality of through-hole portions penetrating through the metal member.

DESCRIPTION OF THE INVENTION

In the process of performing research to identify the metal composition of a plate-shaped metal member having a plurality of through-hole portions penetrating through the metal member such as a CRT shadow mask with use of an electrical property or optical property, the inventors of the present invention found that there are cases in which even though the metal composition is the same, there is a large difference in measurement values of the above properties depending on, for example, the ratio of the through-hole portions to the measurement area in the test object and the configuration of the through-hole portion. Also, as a result of further research, the inventors found that determining a threshold value using a reference value and information indicating the ratio of the through-hole portions to the measurement area in the test object and/or information indicating the configuration of the through-hole portion, and comparing the threshold value and a measurement value of the test object as described above enables highly precise identification of the metal composition (hereinafter, also called the "material", "type of metal", or "metal") of a plate-shaped metal member having a plurality of through-hole portions penetrating through the metal member, and thus arrived at the present invention.

A metal identifying device of the present invention includes the above-described measurement unit, a threshold value determination unit that determines a threshold value with use of a reference value obtained by measuring an electrical property and/or optical property of a metal member have a metal composition to be identified and information indicating a ratio of the through-hole portions to the measurement area in the test object and/or information indicating a configuration of the through-hole portion, and a comparison/identification unit that identifies the metal composition of the test object by comparing the measurement value and the threshold value. The metal identifying device of the present invention includes the threshold value determination unit, thereby enabling highly precise identification of the metal composition of a plate-shaped metal member having through-hole portions, which is the test object.

A main component of the "metal member" may be one type of metal element or an alloy. Examples of alloys include an alloy in which two or more types of metal elements have been melted and coagulated, and an alloy that includes one or more types of metal elements and nonmetal elements and/or metalloid elements.

Figure 1A:
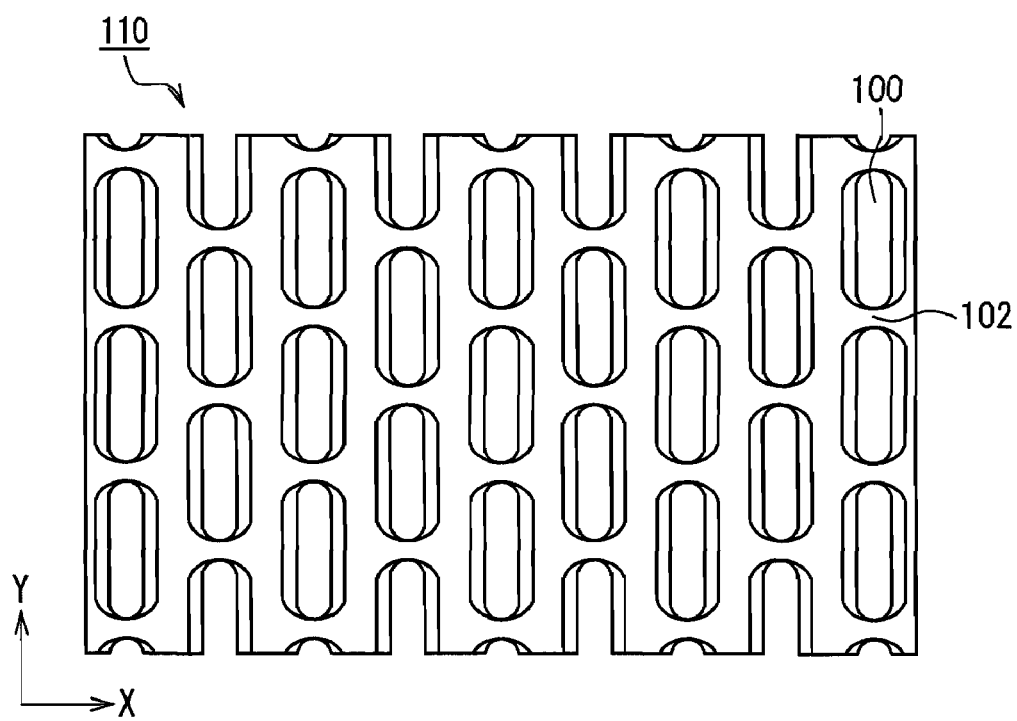
FIG. 1A is plan view showing an exemplary configuration of a press mask.
Figure 1B:
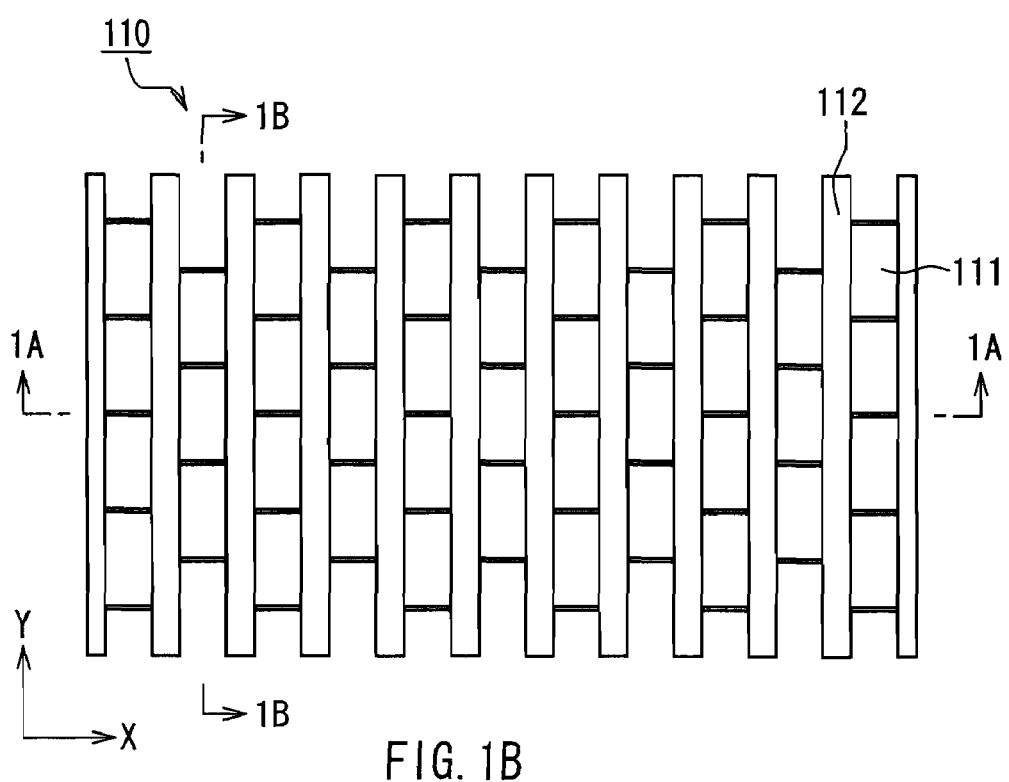
FIG. 1B is a plan view showing an exemplary configuration of a tension mask.

In the present invention, examples of the "plate-shaped metal member having a plurality of through-hole portions penetrating through the metal member" include a CRT shadow mask. Here, "CRT shadow mask" refers to a shadow mask used in a CRT display, and generally is formed by etching several hundred thousand to several million very small through-hole portions in a steel plate that is approximately 0.1 to 0.3 mm thick. As previously described, iron or an Invar alloy can be used as the metal constituting the shadow mask. Shadow masks are divided into two types, namely "tension masks" and "press masks", depending on the production method. Here, "press mask" refers to a mask in which a mask formed into a box configuration by press processing is fitted into and fixed to a support member, and "tension mask" refers to a mask in which a thin plate-shaped mask is fixed to a support member by applying tensile force to the mask, and in this condition, soldering two edges of the mask to the support member. Exemplary configurations of a press mask and a tension mask are shown in FIGS. 1A and 1B respectively. A press mask 110 and a tension mask 110 are constituted from metal portions 102 and 112 and a plurality of through-hole portions 101 and 111 formed in the metal portions 102 and 112. As shown in FIG. 1, the configuration of the through-hole portion and the ratio of the through-hole portions differs according to the production method, CRT display screen size, and the like. Due to these differences, even if the type of the metal material (metal composition) is the same, there are cases in which there are differences in the electrical property measurement values and optical property measurement values of shadow masks. Although the through-hole portions 101 and 111 generally are formed by etching as described above, the through-hole portions 101 and 111 may be formed by forming holes in the metal portions 102 and 112 by press formation or the like. As long as the configuration of the through-hole portions 101 and 111 is a configuration or pattern that enables the passage of an electron beam, there are no particular limitations thereon. Examples of the configuration of the through-hole portions 101 and 111 include an elliptical configuration, a rectangular configuration, a circular configuration, and the like.

A "threshold value" in the present invention is a value to be a reference for identifying the metal composition of a test object by comparison with a measurement value of the test object. The threshold value is determined with use of reference values obtained by measuring an electrical property and/or optical property of a metal member having a metal composition to be identified, and information indicating a ratio of the through-hole portions to the measurement area in the test object and/or information indicating the configuration of the through-hole portion. Note that here, "information" includes the later-described "information indicating the direction in which the through-hole portions in the test object are aligned". Also, there are cases in which the "information indicating the ratio of the through-hole portions", "information indicating the alignment direction of the through-hole portions", and "information indicating the configuration of the through-hole portion" are simply referred to as the "through-hole portions ratio", "through-hole portion alignment direction", and "through-hole portion configuration" respectively. Examples of the threshold value include a value selected from a plurality of reference values, and a value obtained by correcting a reference value as necessary. Examples of the "electrical property" in the present invention include an electrical resistance value. Examples of the "optical property" include emission, reflection, and luster. Specific examples of the "optical property" include an emission spectrum, an emission intensity, a reflection spectrum, a reflection rate (intensity), a luster spectrum, and a luster intensity.

In the present invention, a "reference value" is a value used for determining a threshold value, and is obtained by measuring an electrical property and/or optical property of a metal member having a metal composition to be identified. The "metal composition to be identified" is the type of metal constituting the test object, and examples thereof include a metal element, alloy, or the like that is the main component of the test object. If the test object is an alloy, the metal composition to be identified may be at least one type of metal element included in the alloy. Examples of the reference value include an electrical property value and/or optical property value measured in advance according to a ratio of the through-hole portions to the measurement area in a metal member and/or configuration of the through-hole portion, and an electrical property value and/or optical property value of a metal plate (not including through-hole portions) whose metal composition is to be identified. Accordingly, as described later, examples of the reference value include an electrical resistance value, an emission intensity, an emission spectrum, a reflection rate, a reflection spectrum, a luster intensity, and a luster spectrum. The reference value may be stored in a memory unit of the metal identifying device, or may be measured at the same time as the measurement of the test object. The number of reference values can be determined appropriately according to, for example, the types of metal compositions to be identified, and may be a single reference value or a plurality of reference values.

In the metal identifying device of the present invention, the "threshold value determination unit" determines a threshold value with use of a reference value and information indicating the ratio of the through-hole portions to the measurement area in the test object and/or information indicating the configuration of the through-hole portion. The threshold value can be determined by, for example, preparing a plurality of electrical property measurement values and/or optical property measurement values (reference values) according to information indicating the ratio of the through-hole portions to the measurement area in the metal member and/or information indicating the configuration of the through-hole portion, and selecting a threshold value from among the reference values based on the information indicating the ratio of the through-hole portions to the measurement in the test object and/or information indicating the configuration of the through-hole portion. Also, the threshold value may be determined by determining a coefficient (configuration coefficient) based on the configuration of the through-hole portion and/or a coefficient (ratio coefficient) based on the ratio of the through-hole portions, and correcting the electrical property value and/or optical property value (reference value) of the metal plate whose metal composition is to be identified, with use of the coefficients. The former case enables easily determining the threshold value, since the threshold value can be determined from among reference values measured in advance regarding split-new shadow masks having, for example, different creation methods, metal member materials (metal member metal compositions), and through-hole ratio, based on the configuration of the through-hole portion and/or ratio of the through-hole portions. In the latter case, determining the threshold value is simple since the threshold value can be determined by, for example, setting a value measured for a metal plate without through-hole portions as a reference value, and correcting the reference value with use of the configuration coefficient and/or the ratio coefficient. Note that if the test object is a shadow mask, the configuration coefficient and/or the ratio coefficient can be determined uniquely according to the shadow mask creation method and/or screen size of the CRT display in which the shadow mask is disposed. Although a case of correcting the reference values is described above, a measurement value may be corrected according to the configuration coefficient and/or the ratio coefficient, or a measurement value may be amplified and then corrected according to the above coefficients etc. Correcting the reference values is preferable from the viewpoint of eliminating the superposition of noise components due to signal amplification and the ability to perform highly precise identification.

In the metal identifying device of the present invention, the "comparison/identification unit" identifies the metal composition of a test object by comparing a measurement value and a threshold value. Here, "identifying the metal composition" refers to detecting the metal composition (type of metal) of the test object. If the test object is an alloy material, the metal composition of the test object may be identified by detecting at least one type of metal element included in the alloy, or the metal composition of the test object may be identified by detecting the metal alloy material as one metal. For example, if it is clear that the test object is constituted from either an iron material or an Invar alloy material, whether the test object is the Invar alloy material may be detected by comparing a measurement value and a threshold value that enables detecting the Invar alloy material, or the metal material may be identified as the Invar alloy material by detecting whether a nickel component is contained by comparing a measurement value and a threshold value that enables detecting nickel. Note that the present invention is not limited to the content described above.

Examples of the "measurement unit that obtains a measurement value by measuring an electrical property" in the metal identifying device of the present invention include a measurement unit that measures an electrical resistance value by two measurement probes. Preferably, the measurement probes are a resistance measurement device employing a four-terminal measurement method in which an electrical resistance value is measured by a four-terminal measurement probe provided with two measurement probes that are each constituted from a current application terminal that applies a constant current to a metal member and a voltage measurement terminal that comes into contact with the metal member and measures a potential difference, where the two measurement probes are disposed so that the voltage measurement terminals of the measurement probes are positioned at a predetermined separation distance between each other. The resistance measurement device that measures an electrical resistance value by measurement probes enables highly precise identification of the metal composition of a test object by, for example, merely pressing the probes against the metal member. According to the resistance measurement device employing the four-terminal measurement method, the current application terminals and voltage measurement terminals are separated, thereby enabling, for example, removing the influence of contact resistance that occurs between the current application terminal that applies a constant current and the contact face of the test object. This enables highly precise measurement of an electrical resistance value without the influence of contact resistance. Disposing the voltage measurement terminals at a predetermined separation distance between each other enables, for example, measuring a stable electrical resistance value and very highly precise identification of the metal composition. The lower limit of the separation distance is, for example, preferably 50 mm or greater, or more preferably 100 mm or greater, due to the fact that, even if the test object is a plate-shaped metal member having a plurality of through-hole portions penetrating through the metal member, a stable resistance value can be measured regardless of the measurement area, configuration of the through-hole portion, ratio of the through-hole, and the like. Also, it is sufficient for the upper limit of the separation distance to be less than or equal to the distance of the measurement limit of the test object.

Even if the metal composition of metal members is the same, the electrical resistance value varies depending on the direction in which the through-hole portions in the metal members are aligned, as well as the ratio of the through-hole portions to the metal member and the configurations of the through-hole portion. For example, if the test object is a shadow mask, the shadow mask blocks the electron beam that excites the phosphors as described above, and therefore the wider the surface area of the through-hole portions, the more improved the brightness of the CRT display is. Since CRT displays have a predetermined aspect ratio as is widely known, it is advantageous to provide through-hole portions that are suitable for the aspect ratio. For this reason, the configuration of the through-hole portion is generally not circular, but instead is often a rectangle or an elongated ellipse formed by cutting off the corners of a rectangle. Accordingly, in shadow masks, the rectangular or elongated ellipse-shaped through-hole portions are arranged in lines so that the long-side directions (long axis) are all the same direction and the short-side directions (short axis) are all the same direction. The direction of measuring the electrical resistance value of such a shadow mask metal member is, for example, divided into two main cases, namely a case of measuring parallel to the long axis direction of the through-hole portions and a case of measuring parallel to the short axis direction of the through-hole portions. In the method of manufacturing shadow masks, the width of the metal member between through-hole portions that are adjacent in the long axis direction of the through-hole portions is smaller than the width of the metal member between through-hole portions that are adjacent in the short-axis direction of the through-hole portions. Accordingly, in a case of measuring an electrical resistance value in the short-axis direction of the through-hole portions, measuring is performed via a thin portion of the metal member, and therefore the current path along which the current flows (the cross-sectional area of the metal member) is narrow. However, in a case of performing measuring in the long-axis direction of the through-hole portions, the current path is relatively wide. Since the difference in widths of the current path causes variations in electrical resistance values, the alignment direction in which the through-hole portions are aligned in the metal member also exerts an influence. However, since the width of the metal member between adjacent through-hole portions can also be said to be the ratio of the through-hole portions in the metal member, unless there is a special preference in the present invention, the "through-hole portion alignment direction" includes the "ratio of the through-hole portions".

Examples of the "measurement unit that obtains a measurement value by measuring an optical property" in the metal identifying device of the present invention include an emission measurement unit that measures an emission intensity, a reflection measurement unit that measures a reflection rate, and a luster intensity measurement unit that measures a luster intensity.

Examples of the emission measurement unit that measures an emission intensity include an emission/dispersion measurement device that includes a discharge electrode for causing a metal member to generate a discharge and an emitted light reception unit for collecting and receiving emitted light from the metal member that has been excited by the discharge. The metal identifying device that makes use of the emission intensity enables highly accurate and efficient identification of the metal composition of a test object even if, for example, there are shifts or the like in the through-hole portion pattern due to dirt, scratches, deformations, or the like.

Examples of the reflection measurement unit that measures a reflection rate include a reflection rate measurement device that includes a light source for irradiating a light beam on a metal member and a reflected light reception unit for receiving reflected light from the metal member. Also, examples of the luster measurement unit that measures a luster intensity include a luster intensity measurement device that includes a light source for irradiating a light beam on the metal member and a luster reception unit for receiving luster from the metal member. The metal identifying device that includes the luster measurement unit for measuring a reflection rate or a luster intensity eliminates the need for contact between the measurement unit and the test object, and enables identification of the metal composition of the test object without damaging the test object.

The measurement unit for measuring an optical property preferably includes a collimating lens that converts irradiated light from the light source into a parallel light beam, from the viewpoint of, for example, improving the identification precision by increasing the intensity of the optical property measurement value. Also, the measurement unit for measuring an optical property preferably includes an angle modification unit that modifies an angle formed between the center axis of the light beam and the surface of the metal member by moving the light source, from the viewpoint of, for example, improving the identification precision by adjusting the intensity of the optical property to be measured.

The measurement unit for measuring an optical property preferably includes a spectral analysis unit that generates a dispersion spectrum for light received by the light reception unit, due to being able to improve the identification precision by dispersing the received light into respective wavelengths and comparing the dispersion spectrums of each wavelength.

The metal identifying device of the present invention may include a mount unit on which the metal member (test object) is placed. The mount unit may include a fixing jig from the viewpoint of, for example, improving the identification precision by correcting deformations and the like in the metal member. Examples of the fixing jig include a permanent magnet. Also, an electromagnet or the like may be embedded in the surface of the mount unit to enable fixing of the metal member, correction of deformations, and the like by applying a current to a coil of the electromagnet. The mount unit may be able to have a monitor (comparison) metal member placed thereon, in addition to the test object. This structure enables measuring a reference value to be used in determining a threshold value such as a reference spectrum of a metal included in a metal member, at the same time as the test object is measured, thereby eliminating the need to, for example, store reference values in a memory or the like. Also, this structure enables a reference spectrum and the like to be measured under the same conditions as the test object, thereby enabling further improving the identification precision. Also, the metal identifying device of the present invention further may include a memory unit for storing the reference values and the like.

The metal identifying device of the present invention may include a movement control unit that moves at least one of the mount unit and the measurement unit. The movement direction is not particularly limited, and it is sufficient for the movement to enable, for example, causing the luminous flux of a light beam irradiated on the test object in a case of measuring an optical property to be irradiated on a greater amount of the metal member. The movement may be in a linear direction or a rotational direction.

The metal identifying device of the present invention further may include a measurement position detection unit that detects a measurement position on the metal member and a through-hole portion detection unit that detects a position of a through-hole portion in the metal member. The inclusion of the measurement position detection unit and/or through-hole portion detection unit enables improving the identification precision by, for example, reliably irradiating the irradiated light etc. from the light source on a metal portion of the metal member (test object). In particular, in a case of the luminous flux diameter of the irradiated light being less than or equal to the through-hole area of a through-hole portion, the irradiated light can be irradiated selectively on the metal portion surrounding the through-hole portion, by causing the measurement position detection unit and/or through-hole portion detection unit to work in cooperation with the above-described movement control unit.

As described above, the metal identifying method of the present invention includes a measuring step of obtaining a measurement value by measuring an electrical property and/or an optical property of a test object that is a plate-shaped metal member having a plurality of through-hole portions penetrating through the metal member, a threshold value determining step of determining a threshold value with use of a reference value obtained by measuring the property of a metal member having a metal composition to be identified and information indicating a ratio of the through-hole portions to the measurement area in the test object and/or information indicating a configuration of the through-hole portion, and a comparing/identifying step of identifying the metal composition of the test object by comparing the measurement value and the threshold value. The metal identifying method of the present invention can be performed with use of, for example, the metal identifying device of the present invention.

As described above, the threshold value can be determined in the threshold value determining step by, for example, preparing a plurality of electrical property values and/or optical property values (reference values) according to the ratio of the through-hole portions to the measurement area in the metal member and/or the configuration of the through-hole portion, and selecting a threshold value from among the measurement values based on the ratio of the through-hole portions to the measurement area in the test object and/or the configuration of the through-hole portion of the metal member that is the test object. Also, the threshold value can be determined by correcting a reference value obtained by measuring a metal member having a metal composition to be identified, with use of the configuration of the through-hole portion and/or the ratio of the through-hole portions. The determination of the threshold value may be, for example, executed by a computer or performed by a measuring individual. The configuration of the through-hole portions in the metal member and/or the ratio of the through-hole portions to the measurement area in the metal member may be, for example, detected visually or determined by an imaging device, an optical element, and the like.

Examples of the electrical property include an electrical resistance value. A case of identifying the metal with use of an electrical resistance value facilitates identifying the metal composition of the test object since, for example, electrical resistance values vary greatly depending on the metal composition. Examples of the optical property include an emission spectrum, emission intensity, reflection spectrum, reflection rate (intensity), luster spectrum, and luster intensity. A case of identifying the metal with use of emitted light enables identifying the metal composition of the test object highly accurately and efficiently even if, for example, there are shifts or the like in the through-hole portion pattern due to dirt, scratches, deformations, or the like. Also, a case of identifying the metal with use of reflected light or luster enables identifying the metal composition of the test object without coming into contact with the test object or damaging the test object. Furthermore, measurement can be performed using a handheld measurement device, thereby enabling easily identifying the metal member.

In the metal identifying method of the present invention, measurement values may be obtained by measuring both an electrical property and an optical property, and measurement values may be obtained by combining different optical properties and measuring them respectively. Detecting the metal composition with use of measurement values pertaining to different properties enables improving the identification accuracy. Examples of combinations include first measuring an electrical resistance value and then measuring an optical property of emitted light or the like, and measuring reflected light and/or luster before measuring emitted light.

In the metal identifying method of the present invention, if the test object is an alloy material, at least only one type of metal element included in the alloy may be identified, or the metal material may be identified as the alloy.

The metal identifying method of the present invention further may include a metal member sorting step of sorting the metal member according to an identification result obtained in the comparing/identifying step.

The metal identifying device and metal identifying method of the present invention can be used in, for example, CRT display recycle processing for metal resource recycling. Specifically, the metal identifying device and metal identifying method of the present invention can be used in a CRT display recycle line in which a CRT and a chassis are roughly disassembled from a CRT display housing, and then a shadow mask and peripheral support members and the like are disassembled from the CRT and sorted. For this reason, examples of the metal member (test object) in the present invention include a metal member obtained in recycle processing line for used electrical appliances.

The following describes preferred embodiments of the metal identifying device and metal identifying method of the present invention with reference to the drawings. Note that although the following description shows exemplary cases in which the test object (metal member) is a shadow mask used in a CRT display, applications of the present invention are not limited to such description.

First is a description of metal identifying devices and metal identifying methods that identify the metal composition of a test object with use of an electrical resistance value, as Embodiments 1-1 and 1-2 of the present invention. The present Embodiments 1-1 and 1-2 are examples of preparing reference values obtained by measuring metal members whose metal composition is to be identified, and determining a threshold value from among the reference values according to a through-hole configuration or a ratio of the through-hole portions to the measurement area in the metal member (test object).

Embodiment 1-1

Figure 2A:
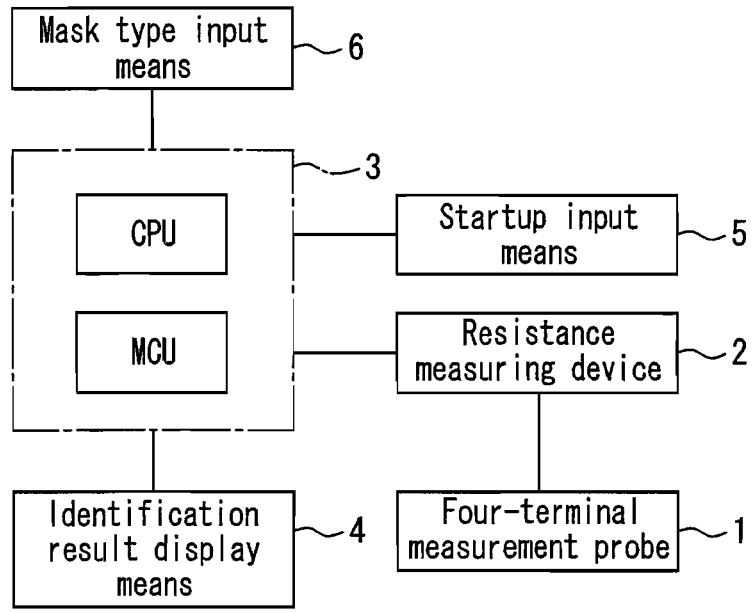
FIG. 2A is a structural diagram schematically showing an exemplary structure of a metal identifying device according to Embodiment 1-1 of the present invention.
Figure 2B:
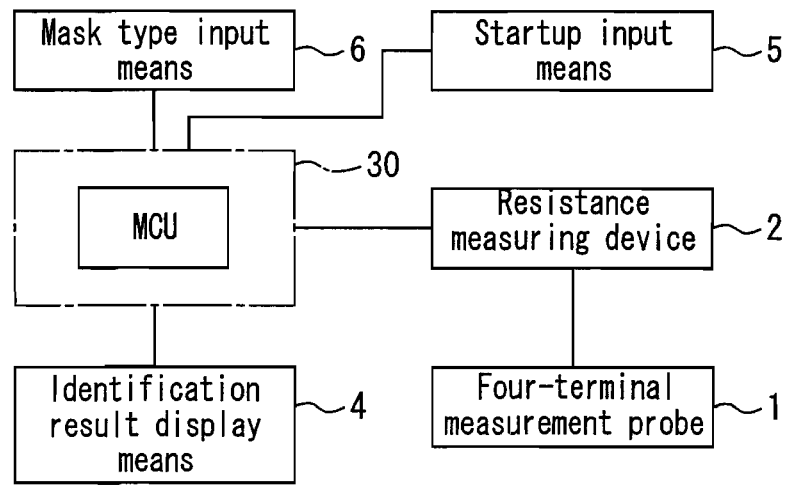
FIG. 2B is a structural diagram schematically showing another exemplary structure of the metal identifying device according to Embodiment 1-1 of the present invention.

FIGS. 2A and 2B are structural diagrams showing an example of a metal identifying device according to Embodiment 1-1 of the present invention. As shown in FIGS. 2A and 2B, the metal identifying device according to the present Embodiment 1-1 is constituted from a four-terminal measurement probe 1, a resistance measurer 2, an operation processing unit 3, an identification result display means 4, a startup input means 5, and a mask type input means 6. The four-terminal measurement probe 1 and resistance measurer 2 correspond to the above-described measurement unit, and the operation processing unit 3 corresponds to the above-described threshold value determination unit and comparison/identification unit.

The operation processing unit 3 is connected electrically by serial communication cables or the like to the resistance measurer 2, identification result display means 4, startup input means 5, and mask type input means 6. The resistance measurer 2 is connected electrically to the four-terminal measurement probe 1 that comes into contact with a CRT shadow mask and measures an electrical resistance value. The operation processing unit 3, for example, may be constituted from a CPU (personal computer) and an MCU (microcontroller) etc. as shown in FIG. 2A, or from the viewpoint of giving the operation processing unit 3 a compact and inexpensive structure, the operation processing unit 3 may be constituted from only an MCU (microcontroller) as in an operation processing unit 30 shown in FIG. 2B.

The identification result display means 4 is a means that display a metal identification result with use of output from the operation processing unit 3. Examples of the identification result display means 4 include visual display units such an LED and an LCD, and auditory display units such as a buzzer.

The startup input means 5 input means 5 is a means that receives an input of an operation start startup signal and transmits the operation start startup signal to the operation processing unit 3. The startup input means 5 is constituted from, for example, a push switch.

The mask type input means 6 is a means that receives an input of, for example, information indicating the configuration of through-hole portions included in a shadow mask and/or a ratio of the through-hole portions to the measurement area in a metal member, a configuration coefficient based on the configuration of the through-hole portion, and a ratio coefficient based on the ratio of the through-hole portions. Examples of the mask type input means 6 include a pair of push switches, a two-way toggle switch, an infrared sensor, and an ultrasound sensor. If the mask type input means 6 is a push switch, toggle switch, or the like, the measuring individual can visually detect a difference between shadow mask production methods (hereinafter, called "mask types"), and manually input the detected mask type. On the other hand, if the mask type input means 6 is an infrared sensor, ultrasound sensor, or the like, these sensors can, for example, automatically detect the mask type and automatically input the detection result. This structure eliminates the need to manually input the mask type and can reduce the number of, for example, human input errors, thereby enabling the realization of a metal identifying device that perform highly precise identification.

Figure 3:
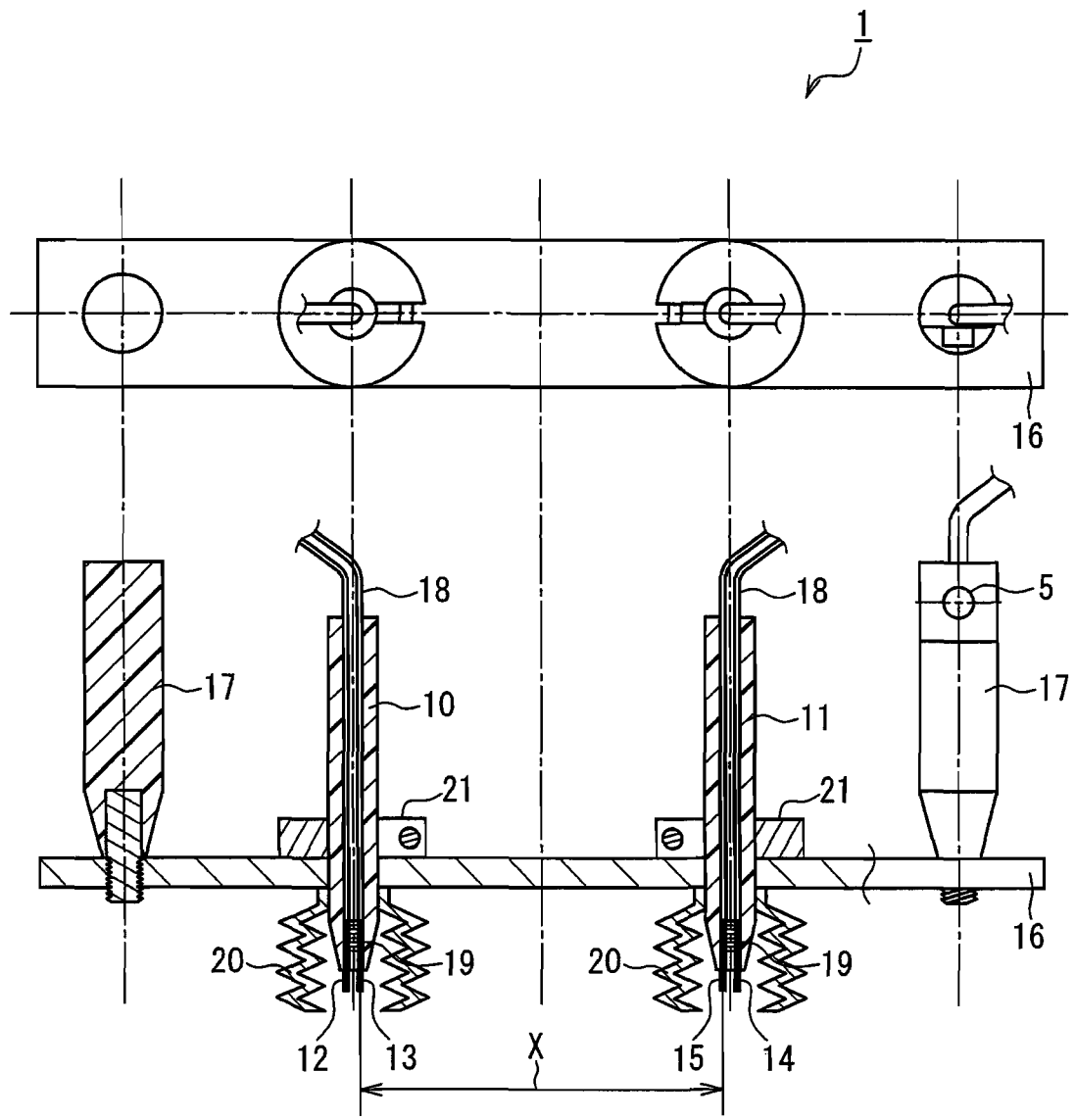
FIG. 3 is a schematic diagram showing an exemplary structure of a four-terminal measurement probe.

FIG. 3 shows an exemplary structure of the four-terminal measurement probe 1. As shown in FIG. 3, the four-terminal measurement probe 1 includes a pair of measurement probes, namely a measurement probe A 10 and a measurement probe B 11, a substrate 16, protection members 20, and two grip holders 17. The measurement probe A 10 and measurement probe B 11 are positioned in a center portion of the substrate 16, and the grip holders 17 are positioned more outward on the substrate 16. The measurement probe A 10 and measurement probe B 11 are fastened by grip collars 21 so that tips of the measurement probes A 10 and B 11 pierce through the substrate 16, and the protection members 20 are fitted around and fixed to the tip portions piercing through the substrate 16. The protection members 20 can expand and contract in the vertical direction. The grip collars 21 and grip holders 17 are each fixed by a screw. The startup input means 5 is disposed in one of the grip holders 17.

The measurement probe A 10 is constituted from a current application terminal A 12, a voltage measurement terminal A 13, a spring 19, and a cable 18. The current application terminal A 12 and voltage measurement terminal A 13 are supported slidably by the spring 19 so as to apply pressure in an outward direction of the measurement probe, and these terminals are each electrically connected to the cable 18. Similarly to the measurement probe A 10, the measurement probe B 11 is constituted from a current application terminal B 14, a voltage measurement terminal B 15, a spring 19, and a cable 18. The current application terminal B 14 and voltage measurement terminal B 15 are supported slidably by the spring 19 so as to apply pressure in an outward direction of the measurement probe, and these terminals are each connected electrically to the cable 18. The other end of each cable 18 is electrically connected to the resistance measurer 2 (FIG. 2). The voltage measurement terminal A 13 and voltage measurement terminal B 15 are disposed on the substrate 16 adjacent to each other at a predetermined separation distance (X), and the current application terminal A 12 and current application terminal B 14 are disposed on the substrate 16 so as to be positioned more outward than the voltage measurement terminals A 13 and B 15. Although two grip holders 17 are provided in the configuration of the four-terminal measurement probe 1 in FIG. 3, the present invention is not limited to this configuration. For example, one grip holder may be disposed between the measurement probe A10 and measurement probe B 11, so that operation by one hand is possible. Also, the disposition of the measurement probes A 10 and B 10 and the grip holders 17 of the four-terminal measurement probe 1 is not limited to the disposition shown in FIG. 3. It is sufficient to have a disposition in which the interval etc. between the measurement probe A 10 and measurement probe B 10 is kept constant. For example, a disposition in which the measurement probe A 10 and the grip holder 17 on the measurement probe A 10 side (the left side of FIG. 3) have been switched is possible. Also, an arrangement in which the measurement probe A 10 and the grip holder 17 on the measurement probe A 10 side, and the measurement probe B and grip holder 17 on the measurement probe B 10 side are in opposition is possible.

A method of measuring an electrical resistance value of a shadow mask using the four-terminal measurement probe 1 shown in FIG. 3 is, for example, as described below. The pair of grip holders 17 is grabbed with both hands, and the current application terminals A and B (12, 14) and voltage measurement terminals A and B (13, 15) are brought into contact with and pressed against the surface of the shadow mask. At this time, the current application terminals A and B (12, 14) and voltage measurement terminals A and B (13, 15) are exposed due to the protection members 20 contracting, and come into contact with the shadow mask due to a constant pressure applied by the springs 19. Then, when a constant current is applied to the shadow mask through the current application terminal A 12 and current application terminal B 14, a potential difference is generated between the voltage measurement terminal A 13 and voltage measurement terminal B 15 due to the electrical resistance of the shadow mask. Measuring the value of the applied constant current and the potential difference between the voltage measurement terminal A 13 and voltage measurement terminal B 15 enables measuring the electrical resistance value of the shadow mask.

According to the four-terminal measurement method, the current application terminals and voltage measurement terminals are separated from each other, thereby enabling removing the influence of contact resistance generated between the current application terminals that apply the constant current and the contact face of the shadow mask. This enables, for example, highly precise measurement of the electrical resistance value without being influenced by contact resistance. Also, since the voltage measurement terminals are brought into contact with the shadow mask under a constant pressure, the shadow mask and terminals can be caused more to reliably be in contact with each other even if the shadow mask has scratches or deformations such as corrugations. This enables highly precise measurement of the electrical resistance value.

Figure 4:
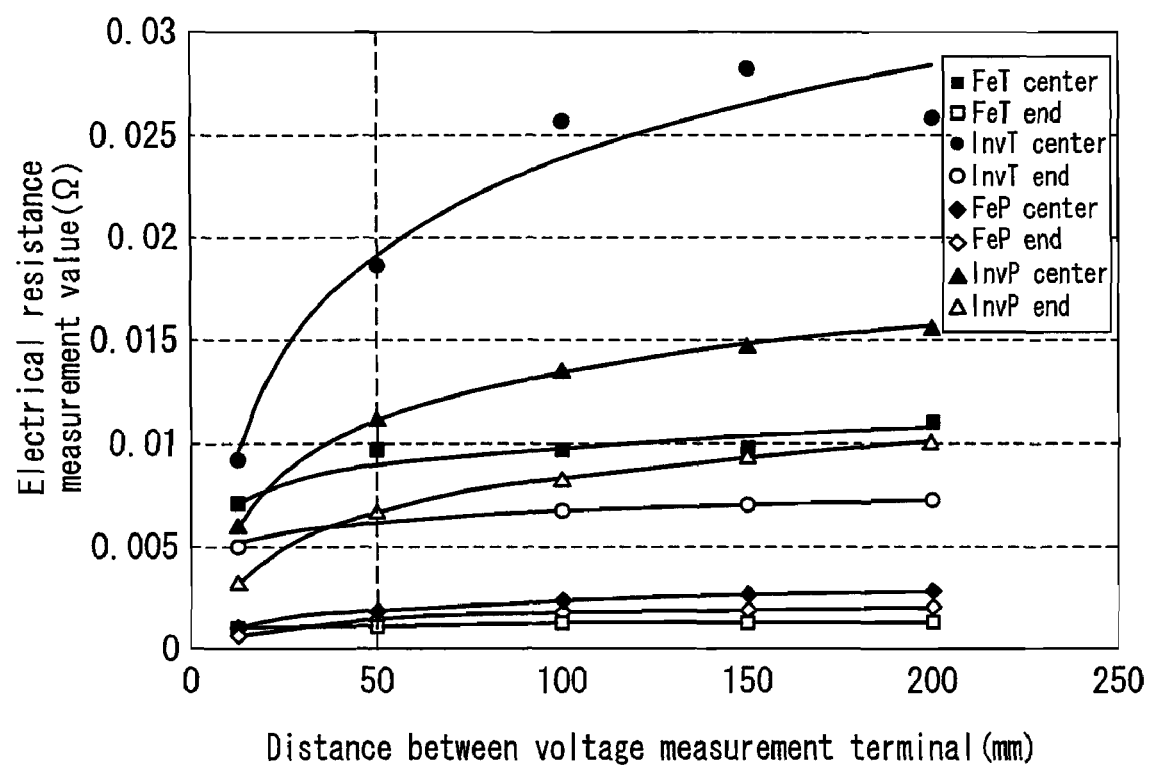
FIG. 4 is a graph showing an exemplary relationship between separation distances (X) between voltage measurement terminals and electrical resistance values of shadow masks.

The graph of FIG. 4 shows the relationship between separation distances (X) and electrical resistance values (measurement values). In FIG. 4, the horizontal axis indicates separation distances (X) between the voltage measurement terminals, and the vertical axis indicates electrical resistance measurement values. This graph shows the results of measuring the electrical resistance values of shadow masks in the same way as described above, while varying the separation distance (X) between the voltage measurement terminals in a range of 15 mm to 200 mm. Two types of shadow masks (a tension mask and a press mask) were prepared for each of an iron material and an Invar alloy material. Two measurement locations (measurement areas) were used, namely a substantially center portion and an end portion of the shadow masks. Note that in FIG. 4, "Fe" indicates the iron material, "Inv" indicates the Invar alloy material, "T" indicates the tension mask, "P" indicates the press mask, "center" indicates that the measurement location is the center portion, and "end" indicates that the measurement location is the end portion.

As shown in the graph of FIG. 4, the obtained measurement results indicate that the electrical resistance value is dependent on the distance between the voltage measurement terminals (separation distance). If the separation distance (X) is 50 mm or greater, the rate of change in the electrical resistance value accompanying a change in the separation distance is relatively moderate, and therefore it can be said that stably measuring the electrical resistance value is possible. Also, if the separation distance (X) is 50 mm or greater, the threshold value for specifying the metal composition using the mask type and/or measurement location can be determined easily. In other words, since the configuration of the through-hole portion and/or the ratio of the through-hole portions to the measurement area in the metal member can be specified according to the mask type and/or measurement location, if for example, a plurality of reference values are set in advance according to the configuration of the through-hole portion and/or the above-described ratio, a threshold value can be selected and determined from among the reference values using the configuration of the through-hole portion and/or ratio of the through-hole portion. Then, the metal composition of the test object can be identified with high precision by comparing the threshold value and the measurement value.

Figure 5A:
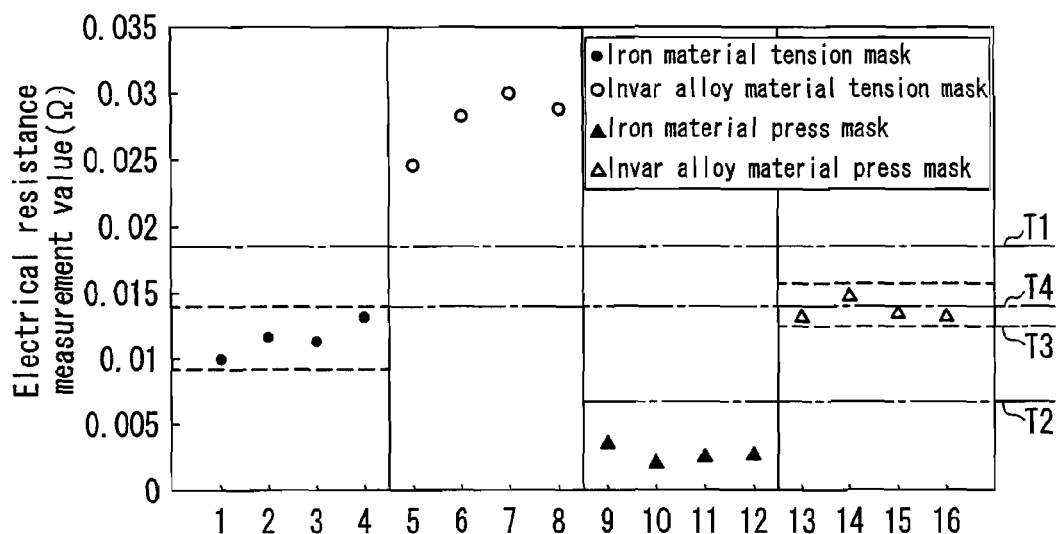
FIG. 5A is a graph showing exemplary electrical resistance measurement values of shadow masks.
Figure 5B:
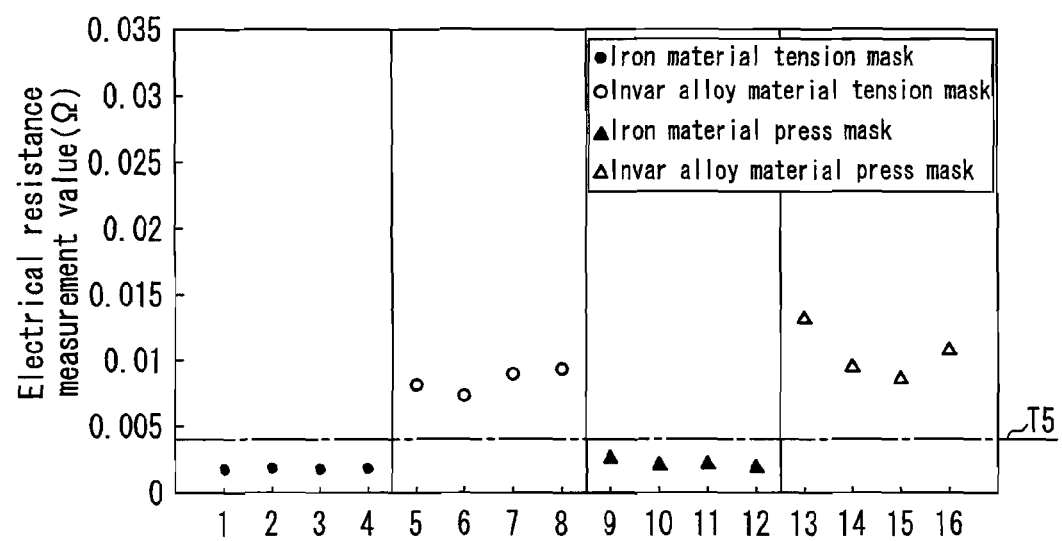
FIG. 5B is a graph showing other exemplary electrical resistance measurement values of shadow masks.

FIGS. 5A and 5B are graphs showing a relationship between shadow mask screen sizes and electrical resistance values. FIG. 5A shows electrical resistance values when the measurement location is the center portion, and FIG. 5B shows electrical resistance values when the measurement location is the end portion. The graphs of FIGS. 5A and 5B shows the results of setting the separation distance (X) between the voltage measurement terminals to 150 mm and measuring the electrical resistance value of shadow masks having screen sizes from 19 inches to 32 inches (16 types) as shown in Table 1 below.

cases in which the electrical resistance values obtained for the iron material tension masks (No. 1 to 4) and the Invar alloy material press masks (No. 13 to 16) are substantially the same even though the metal compositions are different. This is inferred to be the result of the difference in the configuration of through-hole portions of shadow mask between tension masks and press masks. In other words, in tension masks, in order to improve the strength in the direction in which tension is generated (the Y axis direction in FIG. 1B), the cross-sectional area (current path) of the metal member is greater in the lattice cross section in the Y axis direction (the cross section taken along line 1A-1A in FIG. 1B) than in the lattice cross section (the cross section taken along line 1B-1B in FIG. 1B) in the direction orthogonal to the Y axis direction (the X axis direction in FIG. 1B). For this reason, when the electrical resistance value is measured by applying a current in the direction (the X axis direction in FIG. 1B) orthogonal to the direction in which tension is generated, the obtained electrical resistance value is greater than when the electrical resistance value is measured by applying a current in the Y axis direction of FIG. 1B. On the other hand, since press masks are formed by press processing, the electrical resistance value obtained for both the X axis direction and Y axis direction (the short-side (short axis) direction of the through-hole portions and the long-side (long axis) direction of the through-hole portions) is less than when the electrical resistance value is measured in the X axis direction of tension masks. It is thought that due to the above, there are cases in which the obtained electrical resistance values are different even when the metal compositions of the shadow masks are the same, and cases in which the obtained electrical resistance values are substantially the same even though the metal compositions are different.

On the other hand, as shown in FIG. 5B, the electrical resistance values of the iron material tension mask and Invar alloy material press mask are smaller when the measurement location is the end portion than when the measurement location is the center portion. Also, iron material tension masks and Invar alloy material press masks can be identified accurately using a threshold value (reference value) T5. This is thought to be due to the structure of tension masks. The support member that generates tension in the mask is made from the same material as other portions of the mask. The

TABLE 1

| Sample No. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Mask type | Tension mask | | | | | | | | Press mask | | | | | | | |
| Metal type | Iron material | | | | Invar alloy material | | | | Iron material | | | | Invar alloy material | | | |
| Size | 24" W | 25" | 28" W | 29" | 25" | 28" W | 29" | 29" | 19" | 25" | 26" | 28" W | 24" W | 29" | 32" W | 32" W |

As shown in FIG. 5A, when the measurement location is the center portion, the electrical resistance measurement value of the iron material press mask, the iron material tension mask, the Invar alloy material press mask, and the Invar alloy material tension mask rose in the stated order. For this reason, the metal composition of a shadow mask can be identified by, for example, setting two reference values T1 and T2 based on the configuration of the through-hole portion (tension mask/press mask), the ratio of the through-hole portion (measurement location:center portion), and alignment direction of the through-hole portions, detecting the mask type by sight or the like and selecting and determining a threshold value from among the reference values based on the detected mask type, and comparing the threshold value and measurement value.

Also, it can be understood from the graph of FIG. 5A that when the measurement location is the center portion, there are cross-sectional area of the metal member is much larger than the other portions, and the current path along which the current flows is wider. It is thought that for this reason, when the support member (end portion) is measured, the current flows much more easily than in the other portions, and the obtained electrical resistance value is smaller.

Based on the above, it is preferable to prepare at least two or more reference values that can be selected according to the mask type, and for the operation processing unit 3 to select a threshold value from among the reference values with use of the configuration of the through-hole portion and/or the ratio of the through-hole portions to the measurement area in the metal member, and determine the metal composition of the test object by comparing the threshold value and measurement value. Also, the threshold value may be determined by correcting the reference values with the use of the configuration of the through-hole portion and/or the ratio of the through-hole portions to the measurement area in the metal member, and the determined threshold value and measurement value may be compared.

Figure 6:
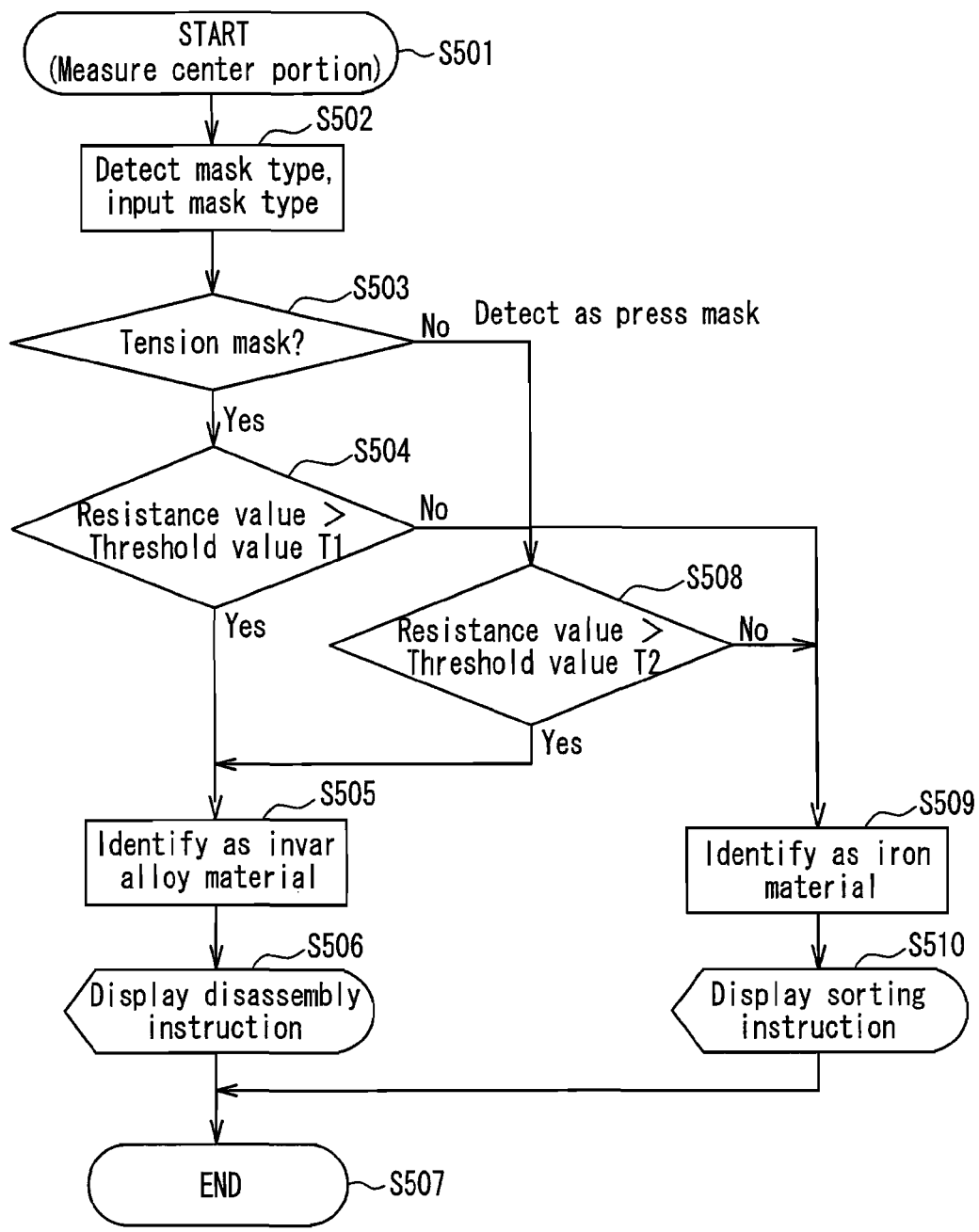
FIG. 6 is a flowchart showing an exemplary comparison operation algorithm according to Embodiment 1-1 of the present invention.

The following describes a metal identifying method according to the present Embodiment 1-1 with reference to FIG. 2 and FIG. 6. FIG. 6 is a flowchart showing an example of a comparison operation algorithm that identifies a metal composition by comparing a threshold value and a measured electrical resistance value.

First, the measuring individual starts the measurement of the shadow mask by operating the startup input means 5 of the four-terminal measurement probe 1 (S501). Next, the measuring individual inputs, to the mask type input means 6, information (e.g., the mask type) that has been obtained by detecting by sight or the like the ratio of the through-hole portions to the measurement area and/or the configuration of the through-hole portion (S502). The input detection signal is transmitted to the operation processing unit 3, and the operation processing unit 3 determines threshold values (T1, T2) with use of the received detection signal and two or more reference values stored in a memory or the like (S503). The mask type detection and input is not limited to being performed by sight. As previously described, the mask type may be detected with use of a sensor such as an infrared sensor or ultrasound sensor and automatically input. Also, in a case of detecting the mask type by sight or the like, instead of inputting the mask type, the measuring individual himself/herself may determine a threshold value based on the mask type and input the determined threshold value.

Next, an electrical resistance value is measured based on the four-terminal measurement method in the resistance measurer 2 by bringing the four-terminal measurement probe 1 into contact with substantially a center portion of the shadow mask that is the test object, so that the voltage measurement terminals are positioned in a direction (the X axis direction in FIGS. 1A and 1B) that is orthogonal to the long-side (long axis) direction of the through-hole portions. The direction in which the measurement probe is brought into contact with the test object is preferably, from the viewpoint of providing a sufficient separation distance between the voltage measurement terminals, a direction that is orthogonal to the long-side (long axis) direction of the through-hole portions. Note that the direction in which the measurement probe is brought into contact with the test object is not limited to this direction. The direction may be a direction parallel to the long-side direction of the through-hole portions, or may be another direction. The measured electrical resistance value is transmitted to the operation processing unit 3 as a serial signal. The operation processing unit 3 performs a comparison operation using the received electrical resistance value and the determined threshold value, and identifies the metal composition of the shadow mask (S504, S508). The metal identification result is transmitted to the identification result display means 4, and the identification result display means 4 informs the measuring individual by displaying the received identification result according to a display method set in advance.

Specifically, if the mask type is a tension mask, the threshold value T1 is determined, and the measured electrical resistance value is compared with the threshold value T1 (S504). If the electrical resistance value is greater than the threshold value T1, the metal composition is identified as the Invar alloy material (S505), an instruction to perform disassembly is displayed on the identification result display means 4 (S506), and thereafter, processing ends (S507). If the electrical resistance value is less than the threshold value T1, the metal composition is identified as the iron material (S509), an instruction to perform sorting is displayed on the identification result display means 4 (S510), and thereafter, processing ends (S507). On the other hand, if the mask type is a press mask, the threshold value T2 is determined, and the measured electrical resistance value is compared with the threshold value T2 (S508). If the electrical resistance value is greater than the threshold value T2, the metal composition is identified as the Invar alloy material (S505), an instruction to perform disassembly is displayed on the identification result display means 4 (S506), and thereafter, processing ends (S507). If the electrical resistance value is less than the threshold value T2, the metal composition is identified as the iron material (S509), an instruction to perform sorting is displayed on the identification result display means 4 (S510), and thereafter, processing ends (S507). Note that if the measurement value matches the threshold value (T1, T2), the electrical resistance value can be measured again, the threshold value can be determined again, or the like.

In this way, a threshold value is selected and determined from among reference values prepared using mask types (configurations of the through-hole portion and the like) that have been detected in advance, and whether the metal composition of the shadow mask is the iron material or Invar alloy material can be detected by comparing the threshold value and the measurement value.

Note that as previously described, there are cases in which measurement values of the electrical resistance value are substantially the same even though the metal composition is different. Specifically, in FIG. 5, if the measured electrical resistance value is between the threshold value T3 and threshold value T4, there are cases in which the metal cannot be identified unless the mask type (configuration of the through-hole portion and the like) has been detected by sight, a sensor, or the like. In such cases, the metal can be identified, for example, as described in the following Embodiment 1-2.

Embodiment 1-2

Figure 7:
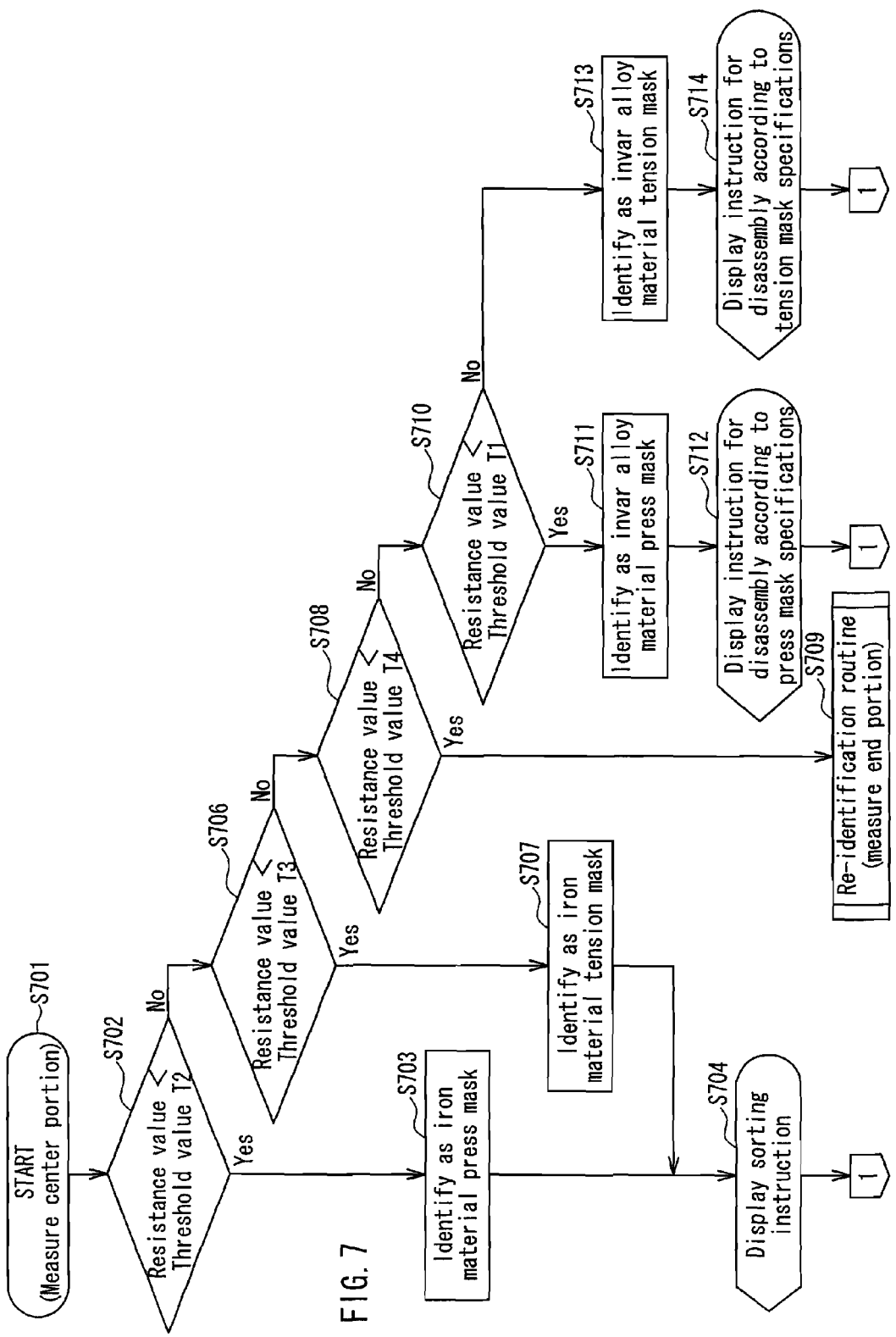
FIG. 7 is a flowchart showing an exemplary comparison operation algorithm according to Embodiment 1-2 of the present invention.
Figure 8:
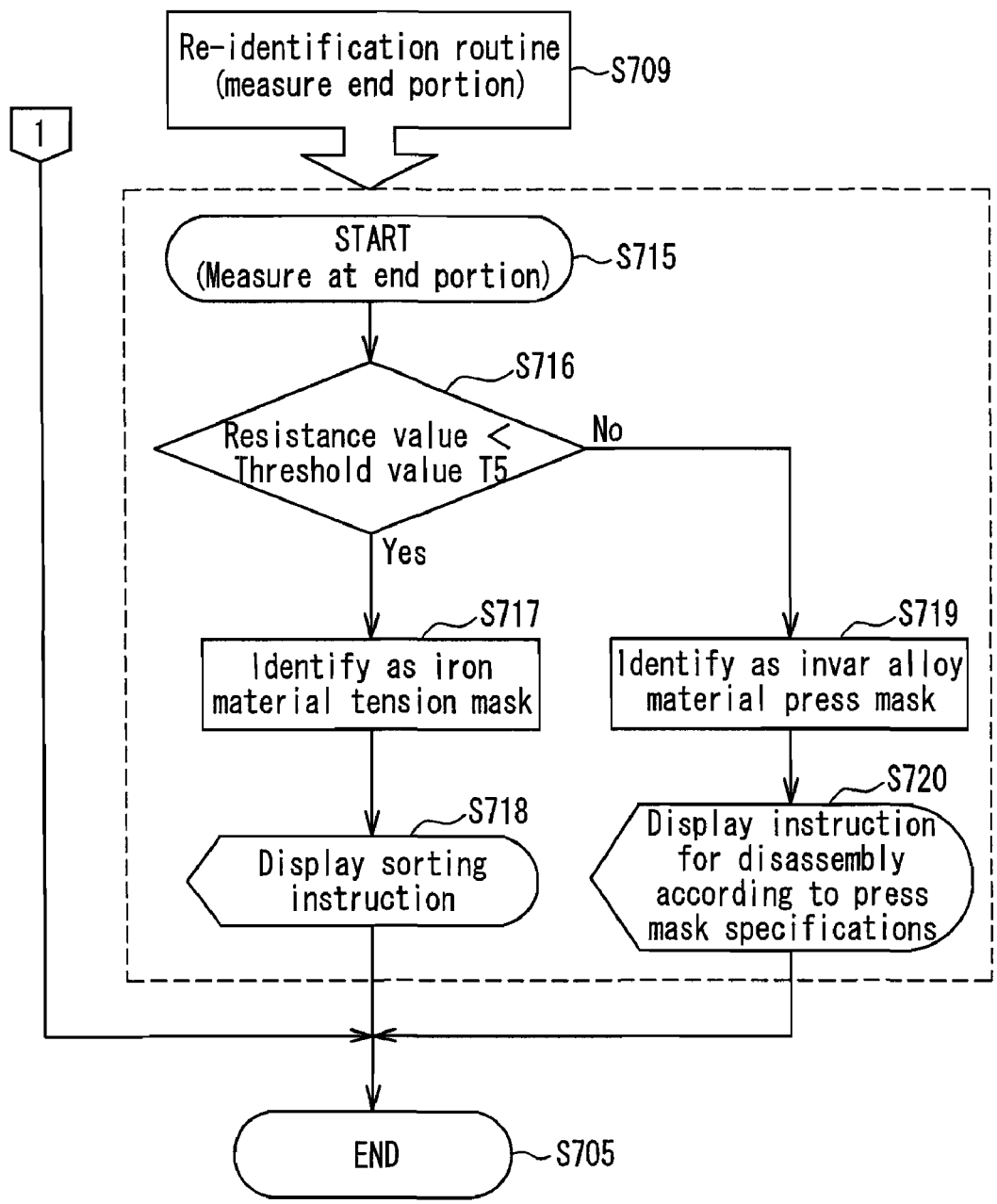
FIG. 8 is a flowchart showing another exemplary comparison operation algorithm according to Embodiment 1-2 of the present invention.

Embodiment 1-2 of the present invention is a method of identifying the metal composition of a shadow mask by measuring an electrical resistance value in both a center portion and an end portion, based on the fact that measurement values of electrical resistance values differ between the center portion and end portion of a shadow mask since the ratio of the through-hole portions is different in these two portions. This method eliminates the need to input a mask type, thereby enabling, for example, reducing erroneous identification due to erroneous input of a mask type. The following describes the metal identifying method of the present Embodiment 1-2 with reference to FIGS. 7 and 8. FIGS. 7 and 8 are flowcharts showing an example of a comparison operation algorithm for identifying a metal composition by comparing a threshold value and a measured electrical resistance value according to the present Embodiment 1-2. FIG. 7 is a flowchart showing an example of the former half of the comparison operation algorithm, and FIG. 8 is a flowchart showing an example of the latter half of the comparison operation algorithm.

First, the measuring individual starts the measurement of the shadow mask by operating the startup input means 5 of the four-terminal measurement probe 1 (S701). Next, an electrical resistance value in the center portion of the shadow mask is measured using the four-terminal measurement probe 1, the threshold value T2 is determined from among reference values using the ratio of the through-hole portions (measurement location:center portion), and the threshold value T2 and obtained electrical resistance value are compared (S702). If the electrical resistance value is less than the threshold value T2, the shadow mask is identified as an iron material press mask (S703), an instruction to perform sorting is displayed on the identification result display means 4 (S704), and thereafter, processing ends (S705 in FIG. 8). If the electrical resistance value is greater than the threshold value T2, the electrical resistance value further is compared with the threshold value T3 (S706). If the electrical resistance value is less than the threshold value T3, the shadow mask is identified as an iron material tension mask (S707), an instruction to perform sorting is displayed on the identification result display means 4 (S704), and thereafter, processing ends (S705 in FIG. 8). If the electrical resistance value is greater than the threshold value T3, the electrical resistance value further is compared with the threshold value T4 (S708). If the electrical resistance value is less than the threshold value T4, processing moves to a re-identification routine (S709). As described above, if the electrical resistance value is between the threshold value T3 and threshold value T4, it is difficult to identify the metal composition unless the mask type etc. has been detected, and therefore it is necessary for processing to move to the re-identification routine.

In the case of moving to the re-identification routine (S709), as shown in FIG. 8, first an electrical resistance value is measured in the end portion of the shadow mask using the four-terminal measurement probe 1 according to the four-terminal measurement method (S715). Then, the obtained electrical resistance value is compared with the threshold value T5 determined from among reference values based on the fact that the measurement location is the end portion (S716). If the electrical resistance value is lower than the threshold value T5, the shadow mask is identified as an iron material tension mask (S717), an instruction to perform sorting is displayed (S718), and thereafter, processing ends (S705). If the electrical resistance value is greater than the threshold value T5, the shadow mask is identified as an Invar alloy press mask (S719), an instruction to perform disassembly according to press mask specifications is displayed (S720), and thereafter, processing ends (S705).

On the other hand, upon comparing the electrical resistance value with the threshold value T4 (S708), if the electrical resistance value is greater than the threshold value T4, the electrical resistance value further is compared with the threshold value T1 (S710). If the electrical resistance value is less than the threshold value T1, the shadow mask is identified as an Invar alloy press mask (S711), an instruction to perform disassembly according to press mask specifications is displayed (S712), and thereafter, processing ends (S705 in FIG. 8). If the electrical resistance value is greater than the threshold value T1, the shadow mask is identified as an Invar alloy tension mask (S713), an instruction to perform disassembly according to tension mask specifications is displayed (S714), and thereafter, processing ends (S705 in FIG. 8).

In this way, according to the metal identifying method shown in the flowcharts of FIGS. 7 and 8, the material of four types of shadow masks (an iron material tension mask, an Invar alloy material tension mask, a iron material press mask, and an Invar alloy material press mask) can be identified by determining five threshold values using two measurement locations (center portion and end portion) that have different ratios of the through-hole portions and prepared reference values (T1, T2, T3, T4, and T5), and comparing a measurement value and a threshold value.

The following describes metal identifying devices and metal identifying methods that identify the metal composition of a test object with use of emitted light, as Embodiments 2-1 to 2-3 of the present invention.

Embodiment 2-1

Figure 9A:
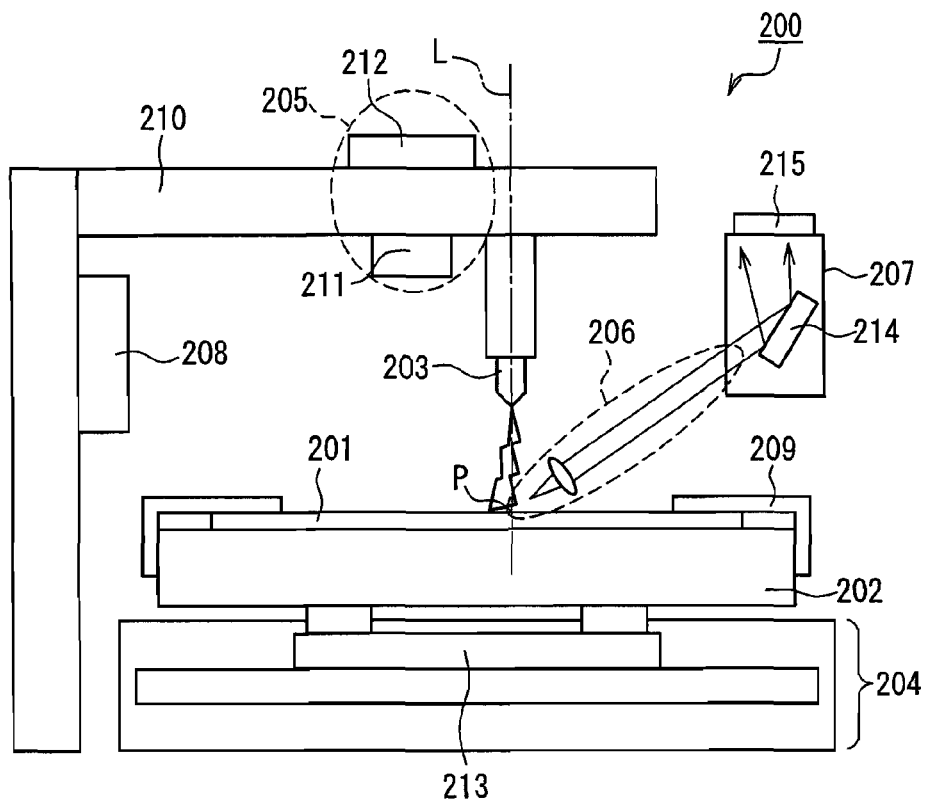
FIG. 9A is a schematic diagram showing an exemplary structure of a metal identifying device according to Embodiment 2-1 of the present invention.
Figure 9B:
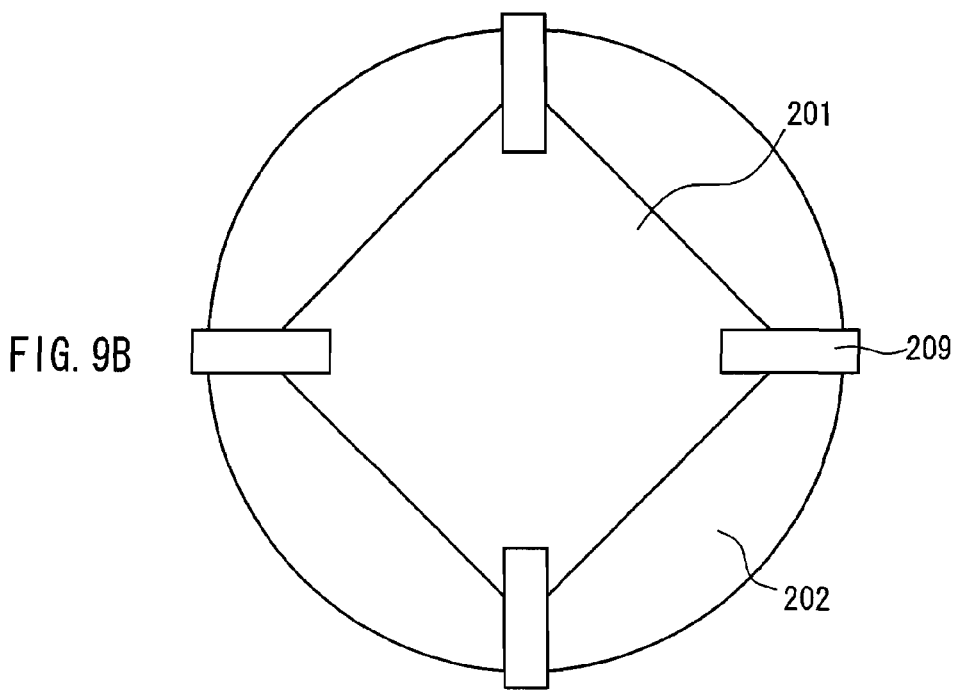
FIG. 9B is a top view showing an exemplary structure of a mount unit of the metal identifying device.

FIG. 9A is a schematic diagram showing a metal identifying device according to Embodiment 2-1 of the present invention, and FIG. 9B is a top view showing an exemplary mount unit (a sample placement table) of the metal identifying device.

The main constituent elements of a metal identifying device 200 shown in FIG. 9A are a mount unit 202, a discharge electrode 203, a movement mechanism unit 204, a position detection unit 205, a light collection/guide unit 206, a light reception/analysis unit 207, and an identification operation unit 208. In this embodiment, the mount unit 202, discharge electrode 203, light collection/guide unit 206, and light reception/analysis unit 207 correspond to a measurement unit, the identification operation unit 208 corresponds to a threshold value determination unit and a comparison/identification unit, the movement mechanism unit 204 corresponds to a movement control unit, and the position detection unit 205 corresponds to a measurement position detection unit and a through-hole portion detection unit. Note that electrical wiring that connects members and functional units has been omitted from FIG. 9A.

Figure 10A:
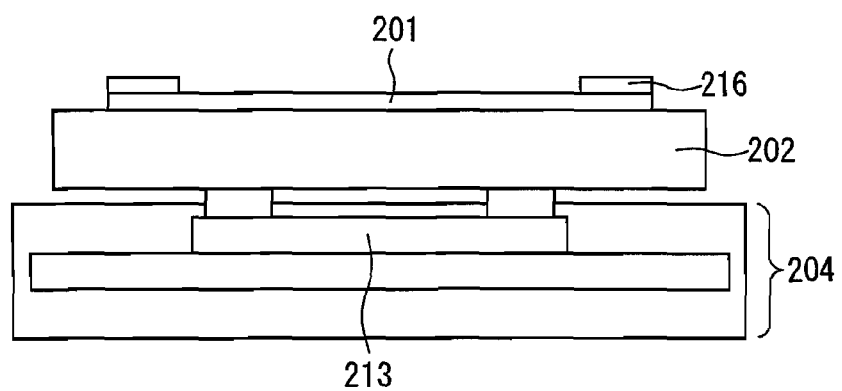
FIGS. 10A and 10B are schematic diagrams showing other exemplary mount units of the metal identifying device according to Embodiment 2-1 of the present invention.
Figure 10B:
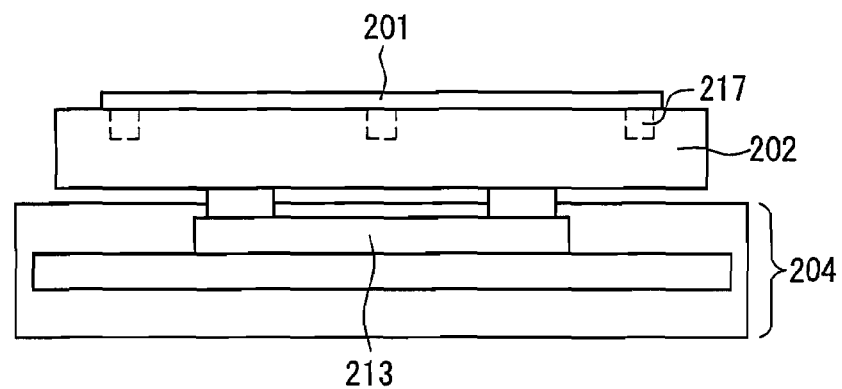

As shown in FIG. 9A, the mount unit 202 is disposed above the movement mechanism unit 204, and the discharge electrode 203 is attached to an arm 210 so as to be disposed above the mount unit 202. A metal member (test object) 201 can be placed on the mount unit 202, and the metal member (test object) can be fixed to the mount unit 202 by a fixing jig 209 or the like (FIG. 9B). The mount unit 202 is disposed so as to be connected to the movement mechanism unit 204, and can move in a planar direction (for example, left and right, and a 360-degree direction) by a linear motor 213. From the viewpoint of eliminating noise components to improve identification precision, the mount unit 202 preferably is formed from a material that does not emit light when excited by a discharge. The structure of the mount unit 202 is not limited to the structure shown in FIG. 9A. For example, as shown in FIG. 10A, the mount unit 202 may be formed from a magnetic body such as iron, the fixing jig 209 may be formed from a permanent magnet 216, and the metal member 201 may be fixed to the mount unit 202 by the attractive force of the magnet. Also, as shown in FIG. 10B, an electromagnet 217 may be embedded in the surface of the mount unit 202, and the metal member 201 may be fixed to the mount unit 202 by applying a current to a coil of the electromagnet 217. In the case of performing fixing using the electromagnet 217, corrugation deformations etc. in a thin plate-shaped shadow mask may be corrected by, for example, increasing the attractive force of the electromagnet 217. The correction of deformations enables accurately maintaining the separation between the shadow mask and the discharge electrode 203, as a result of which, discharge and/or emission intensity measurement can be performed stably in all areas of the shadow mask. Also, stopping the coil current enables easily removing the metal member 201 from the mount unit 202.

The position detection unit 205 includes an imaging device 211 and an image recognition device 212, and is attached to the arm 210 so as to be positioned above the mount unit 202. An image of the surface of the metal member 201 is captured by the imaging device 211, and image recognition is performed on the image by the image recognition device 212, thereby enabling detecting, for example, positional coordinates of through-hole portions of the metal member 201. By detecting, with use of the position detection unit 205, the positional coordinates of the through-hole portions or discharge damage portions such as through-bores formed due to heat generated along with the discharge, it is easy to cause a discharge in a manner such that an intersection P between the metal member 201 and a line L extending through the discharge electrode 203 is located at a place other than the through-hole portions and the discharge damage portions.

The light collection/guide unit 206 collects light emitted by the application of a discharge voltage between the discharge electrode 203 and the metal member 201, and guides the collected light to the light reception/analysis unit 207. The light reception/analysis unit 207 includes a grating 214 and a photoelectric conversion element 215. The grating 214 spectrally decomposes light that has passed through the light collection/guide unit 206, and diffracted light resulting from the spectral decomposition is received and converted to an electrical signal in the photoelectric conversion element 215. A photomultiplier tube, linear image sensor, or the like can be used as the photoelectric conversion element 215.

The identification operation unit 208 is a digital signal processing device constituted from a CPU, a memory, and the like. Based on the configuration of the through-hole portion and/or ratio of the through-hole portions in the metal member 201, the identification operation unit 208 determines a threshold value for a spectral intensity in a wavelength specific to the metal to be identified, and can identify the material of the metal member 201 by comparing the threshold value and an obtained spectral intensity. The threshold value preferably is determined using the configuration of the through-hole portion and/or ratio of the through-hole portions in the metal member 201 and the spectral intensity in the wavelength specific to the metal composition to be identified. If the metal member is a shadow mask, the identification operation unit 208 can identify whether the metal is an iron material or an Invar alloy material.

Figure 11:
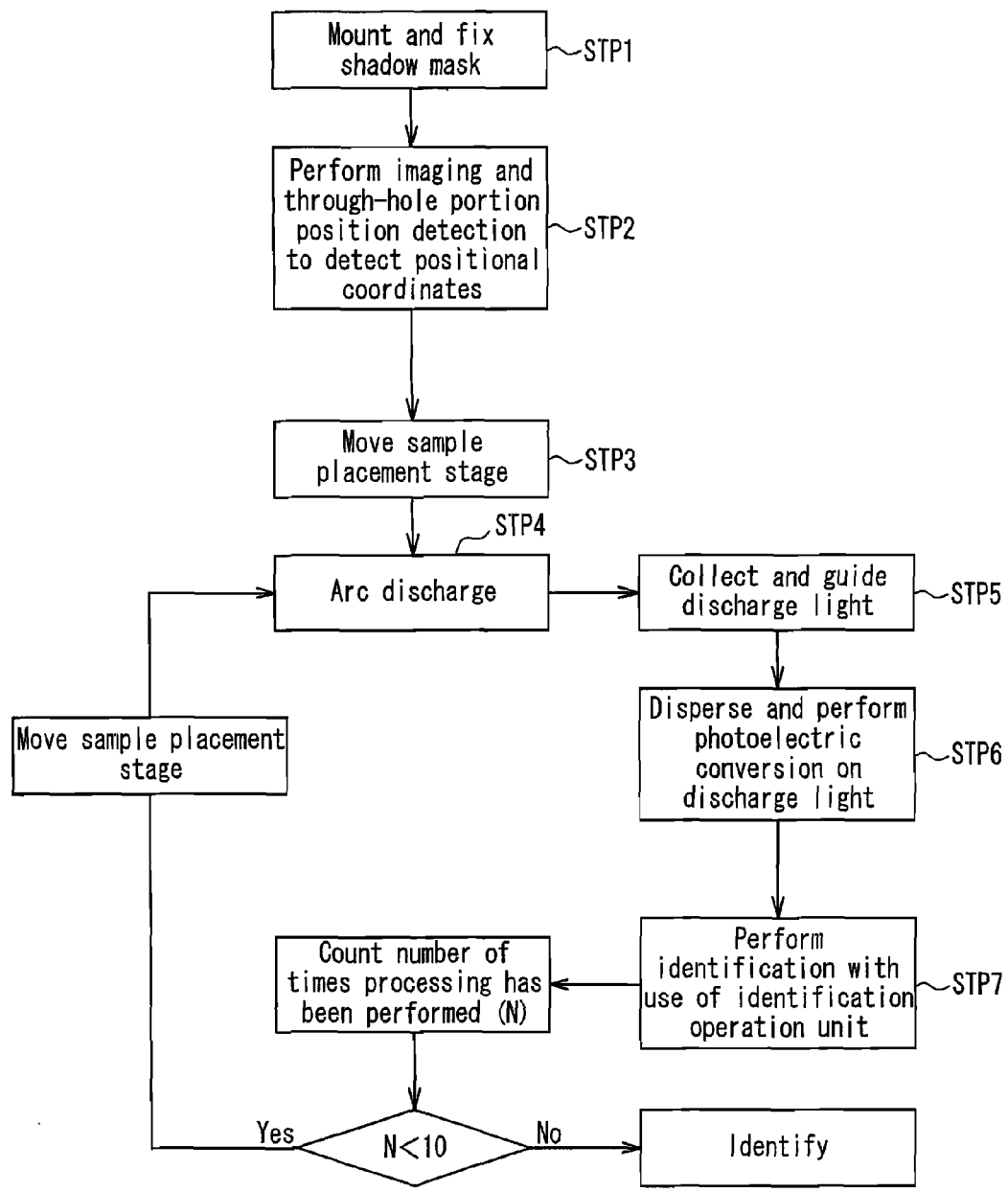
FIG. 11 is a flowchart showing an exemplary metal identifying method according to Embodiment 2-1 of the present invention.

The following describes the metal identifying method of the present Embodiment 2-1 with reference to FIGS. 9 and 11. FIG. 11 is a flowchart showing an exemplary shadow mask metal identifying method according to the present Embodiment 2-1.

First, a shadow mask 201 is placed on the mount unit 202, and the peripheral portion of the shadow mask 201 is fixed by the fixing jig 209 (STP1). Then, an image of the surface of the shadow mask 201 is captured by the imaging device 211, and the positional coordinates of through-hole portions are detected by the image recognition device 212 (STP2). Based on the detected positional coordinate data pertaining to the through-hole portions, the mount unit 202 is moved using the movement mechanism unit 204 so that the intersection P between the shadow mask 201 and the line L extending through the discharge electrode 203 is located at a place other than a through-hole portion, that is to say, at a metal portion (STP3). Next, a discharge voltage is applied between the discharge electrode 203 and the shadow mask 201 to generate an arc discharge (STP4). As a result, light that is specific to the material of the shadow mask 201 is emitted. Then, the light emitted due to the discharge is collected and guided to the light reception/analysis unit 207 by the light collection/guide unit 206 (STP5).

The light that passed through the light collection/guide unit 206 and was incident on the light reception/analysis unit 207 is spectrally decomposed (dispersed) by the grating 214, thereby obtaining a dispersion spectrum specific to the metal constituting the shadow mask (STP6). The obtained dispersion spectrum is converted into electrical signals for each wavelength range by the photoelectric conversion element 215 included in the light reception/analysis unit 207. In this way, electrical signals proportional to the spectral intensity specific to the metal are obtained. The threshold value is obtained as an electrical signal proportional to a reference dispersion spectrum intensity pertaining to the spectral intensity of the iron material constituting the shadow mask and pertaining to the spectral intensity of the Invar alloy material constituting the shadow mask, or as a value obtained by later-described correction or the like. The material of the metal member 201 can be identified by comparing this threshold value and the electrical signals obtained by the photoelectric conversion element 215 (STP7). Here, a plurality of reference dispersion spectrum intensities may be prepared according to the ratio of the through-hole portions to the measurement area in the metal member and/or the configuration of the through-hole portion, and the threshold value that is used may be selected from among the prepared reference dispersion spectrum intensities using the ratio of the through-hole portions in the metal member and/or the configuration of the through-hole portion. Also, the threshold value may be obtained by performing correction on the metal-specific reference dispersion spectrums using the ratio of the through-hole portions in the metal member and/or the configuration of the through-hole portion.

Figure 12A:
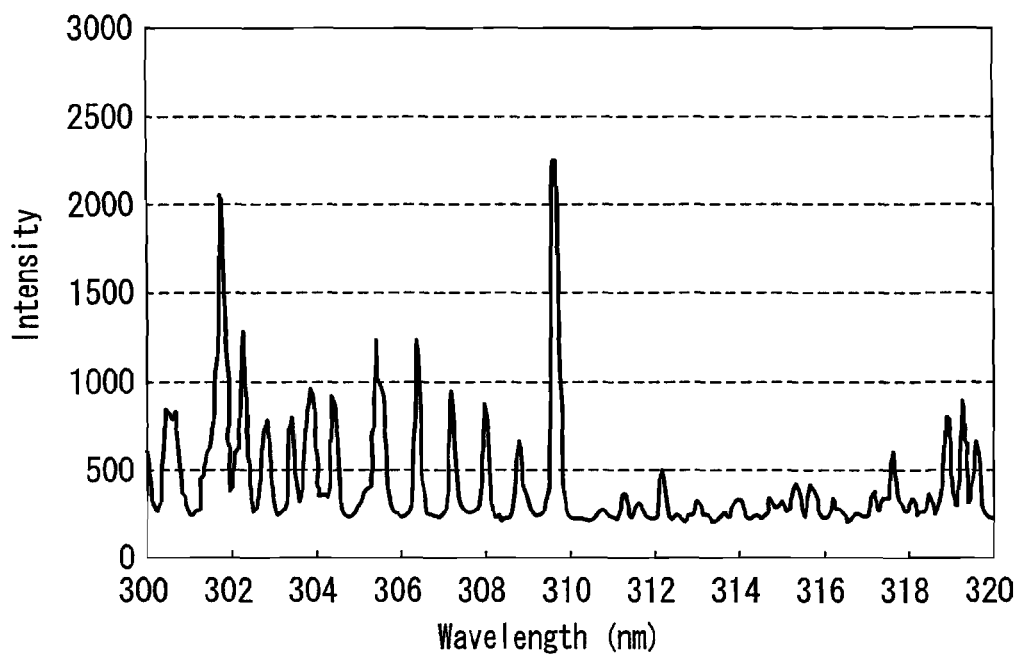
FIGS. 12A and 12B are graphs showing exemplary emission intensity spectrums obtained in Embodiment 2-1 of the present invention.
Figure 12B:
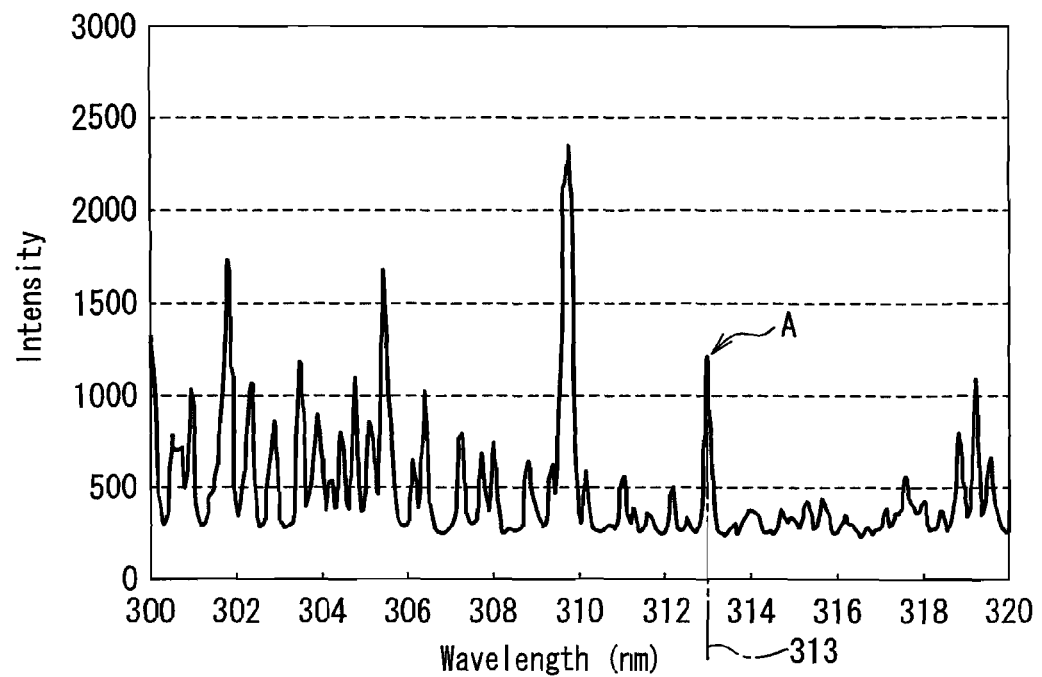

FIGS. 12A and 12B are graphs showing emission intensities when the metal member is a shadow mask. FIG. 12A is a graph showing the emission intensities of an iron material shadow mask, and FIG. 12B is a graph showing the emission intensities of an Invar alloy material shadow mask. It can be understood from FIGS. 12A and 12B that when the shadow mask is constituted from the Invar alloy material, a unique peak A exists in the vicinity of a wavelength of 313 nm. This is a peak originating from nickel. Shadow masks generally are constituted from an iron material or an Invar alloy material. Since the Invar alloy material is an alloy of iron and nickel, whether the shadow mask is constituted from the Invar alloy or the iron material can be identified by, for example, investigating the emission intensity in the wavelength specific to nickel. For example, whether the shadow mask is constituted from the iron material or the Invar alloy material can be identified and detected by performing spectral analysis in the wavelength range of 300 nm to 320 nm and focusing on the magnitude of the emission intensity in the vicinity of the wavelength of 313 nm.

Also, the metal can be identified with even higher accuracy by generating a discharge at a plurality of locations (e.g., approximately ten points) on a single shadow mask, obtaining the emission spectrums, and comparing each of the obtained emission intensities with a threshold value. For this reason, the number of times that measurement has been performed may be counted after the identification operation unit 208 has identified the metal composition, and if the count is less than ten, the mount unit 202 may be moved to change the discharge position, and measurement of the emission intensity may be performed again. On the other hand, if the count is ten or more, detecting may be performed based on the identification results. In this case, it is preferable to obtain spectrums by generating arc discharges at various places while moving the shadow mask by causing the movement mechanism unit 204 to operate, based on the through-hole portion positional coordinate data detected by the position detection unit 205. This enables further improving the identification accuracy.

Embodiment 2-2

Figure 13:
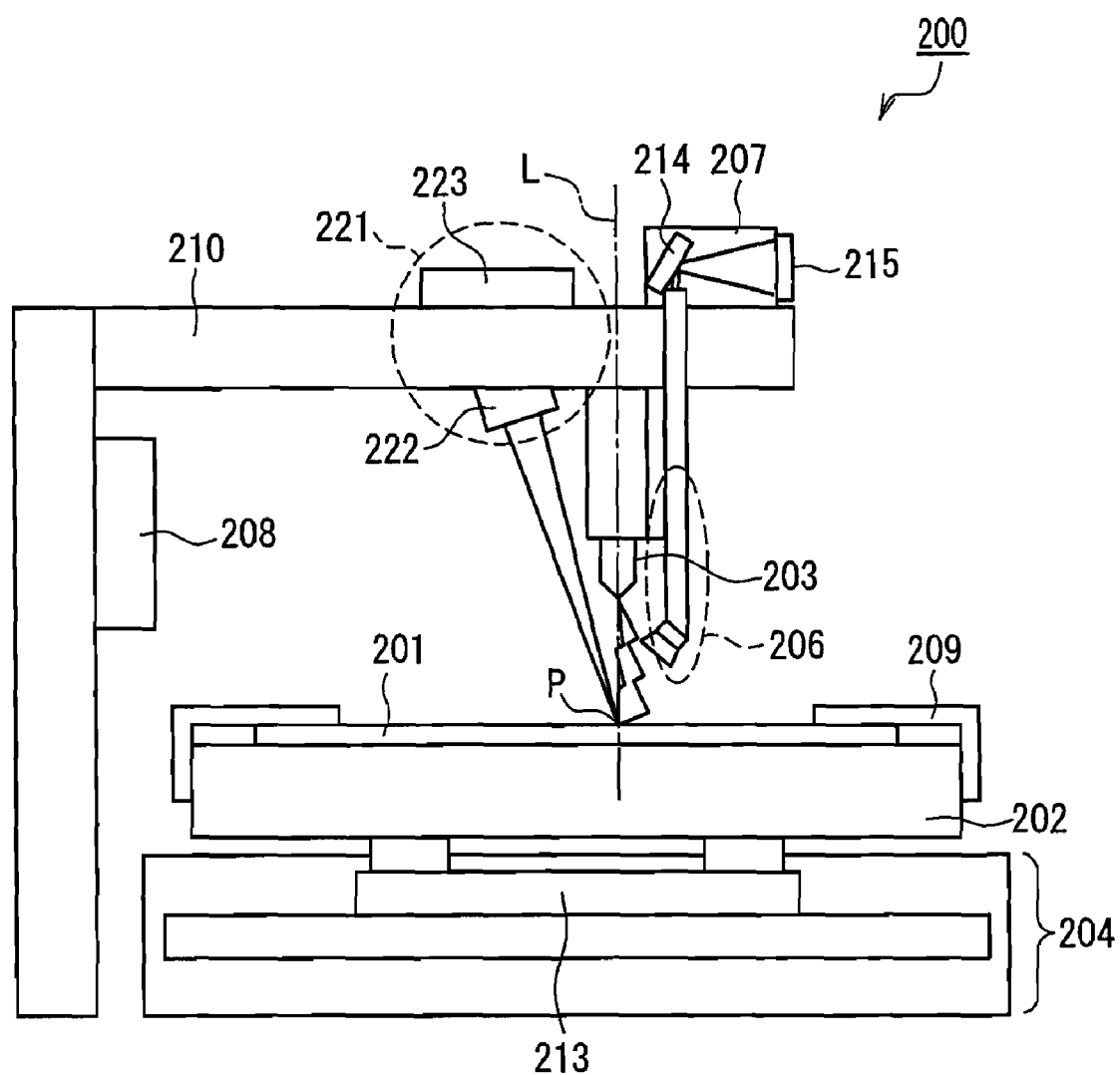
FIG. 13 is a schematic diagram showing an exemplary structure of a metal identifying device according to Embodiment 2-2 of the present invention.

FIG. 13 is a schematic diagram showing an exemplary structure of a metal identifying device according to the present Embodiment 2-2. Note that the same reference signs have been given to portions that are the same as in FIG. 9A.

The main constituent elements of the metal identifying device 200 shown in FIG. 13 are the mount unit 202, the discharge electrode 203, the movement mechanism unit 204, the light collection/guide unit 206, the light reception/analysis unit 207, the identification operation unit 208, and a discharge position detection unit 221. The mount unit 202, movement mechanism unit 204, light reception/analysis unit 207, and identification operation unit 208 are the same as in Embodiment 2-1. The discharge position detection unit 221 corresponds to a measurement position detection unit and a through-hole portion detection unit.

The discharge position detection unit 221 includes a magnifying lens-attached imaging device 222 and an image recognition device 223, and is attached to the arm 210 so as to be positioned above the mount unit 202. The imaging device 222 focuses on the intersection P between the metal member 201 and the line L extending through the discharge electrode 203 and captures an image of this area, and the image recognition device 223 judges whether the image pattern of the image is a through-hole portion. In the case of the present Embodiment 2-2, it is sufficient for the imaging device 222 to capture an image of only a periphery of the discharge position P on the metal sample 201, and therefore it is sufficient for the imaging device 222, for example, to have a narrow field of view.

The light collection/guide unit 206 includes a collecting lens and a quartz rod or optical fiber for light guiding, and is attached to the arm 210 so as to be positioned beside the discharge electrode 203. The light collection/guide unit 206 collects light emitted along with a discharge generated between the discharge electrode 203 and the metal member 201, and guides the collected light to the light reception/analysis unit 207. If the light collection/guide unit 206 includes an optical fiber or quartz rod for light guiding, there is a large degree of freedom in the position of collecting emitted light and the disposition of the light reception/analysis unit 207, which is preferable. Optical fiber can bend the path of light, and therefore provides a large degree of freedom in, for example, the disposition location of the light reception/analysis unit 207. On the other hand, a quartz rod has a high melting point and is superior in terms of heat resistance, and therefore can be positioned close to the discharge site and, for example, can collect high-intensity emitted light.

The following describes an exemplary method for identifying the material of a shadow mask using the metal identifying device of the present Embodiment 2-2. First, the shadow mask 201 is placed on the mount unit 202, and fixed thereto. The fixing can be performed in the same way as in Embodiment 2-1. Then, the imaging device 222 captures an image of the shadow mask 201, and the obtained image signal is input to the image recognition device 223. The image recognition device 223 judges whether a through-hole portion is directly below the discharge electrode 203 by comparing the obtained image signal and pre-stored through-hole pattern data. If a through-hole portion is not directly below the discharge electrode 203, the position of the shadow mask 201 is maintained, and a discharge voltage is applied between the discharge electrode 203 and the shadow mask 201 to generate an arc discharge. On the other hand, if a through-hole portion is directly below the discharge electrode 203, the mount unit 202 is moved using the movement mechanism 204 so that a through-hole is not directly below the discharge electrode 203, and thereafter an arc discharge is generated. The light reception/analysis unit 207 receives light that has been emitted along with the discharge and passed through the light collection/guide unit 206, spectrally decomposes the emitted light, and ultimately converts the resulting light into electrical signals that are proportional to a spectral intensity. The material of the shadow mask 201 can be identified by comparing the electrical signals and a threshold value obtained as described in Embodiment 2-1.

Note that similarly to Embodiment 2-1, it is preferable in the present Embodiment 2-2 as well to generate the arc discharge a plurality of times at different discharge positions in order to improve the identification accuracy. Here, there are cases in which discharge damage such as through-bores exist at locations where the discharge has previously been generated. Furthermore, if the discharge damage is a through-hole, there are cases in which the hole diameter of the through-bore is much larger than a through-hole portion of the shadow mask, and burr-shaped projections formed by random solidification after melting appear at the outer circumferential edge of through-hole portions. If a discharge is generated in the vicinity of a burr-shaped projection, the generated arc discharge becomes focused on the projection, and therefore there are assumed to be cases in which the identification accuracy declines due to generating an arc discharge a plurality of times. However, according to the metal identifying device of the present Embodiment 2-2, arc discharges can be generated while avoiding discharge damage portions with use of the discharge position detection unit 221, thereby enabling highly accurate identification of the metal composition even if arc discharges are generated a plurality of times.

Embodiment 2-3

Figure 14:
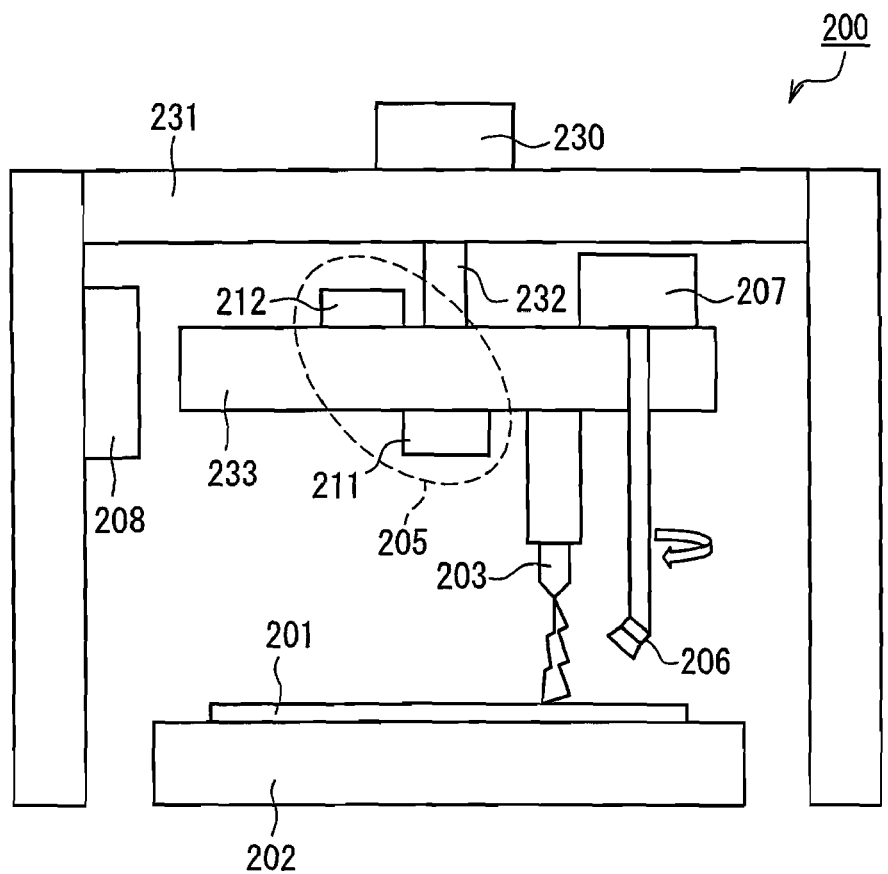
FIG. 14 is a schematic diagram showing an exemplary structure of a metal identifying device according to Embodiment 2-3 of the present invention.

FIG. 14 is a schematic diagram showing an exemplary structure of a metal identifying device according to the present Embodiment 2-3. Note that the same reference signs have been given to portions that are the same as in FIG. 9A and FIG. 13.

The main constituent elements of the metal identifying device 200 shown in FIG. 14 are the mount unit 202, the discharge electrode 203, a rotational movement mechanism unit 230, the position detection unit 205, the light collection/guide unit 206, the light reception/analysis unit 207, the identification operation unit 208, and a housing 231. The mount unit 202, position detection unit 205, and identification operation unit 208 are the same as in Embodiment 2-1, and the light collection/guide unit 206 and light reception/analysis unit 207 are the same as in Embodiment 2-2.

The housing 231 includes a rotation shaft 232 and the rotational movement mechanism 230 that is driven by a motor, and is joined to an arm 233 via the rotation shaft 232. The discharge electrode 203, position detection unit 205, light collection/guide unit 206, and light reception/analysis unit 207 are disposed on the arm 233, and the identification operation unit 208 is disposed on a lateral face of the housing 231. The discharge electrode 203 can be moved in a planar direction (e.g., arc direction) with respect to the mount unit 202 by the rotational movement mechanism 230. For this reason, the discharge position can be determined by, for example, rotating/moving the discharge electrode 203 over the shadow mask 201 based on through-hole portion positional coordinate data.

The light collection/guide unit 206 is attached to an end of the arm 233 so as to be able to follow the discharge position. From the viewpoint of increasing the degree of freedom in the light collecting position and the position of the light reception/analysis unit 207, similarly to Embodiment 2-2, the light collection/guide unit 206 may include a collecting lens and an optical fiber or quartz rod for light guiding. Also, similarly to Embodiment 2-2, it is sufficient to capture an image of at least only a periphery of the discharge position in the present Embodiment 2-3 as well, and therefore the discharge position detection unit 221 of Embodiment 2-2 may be attached to the arm 233 instead of the position detection unit 205.

With the exception of moving the discharge electrode 203 instead of the mount unit 202, the metal identifying device of the present Embodiment 2-3 can identify the metal composition of a test object in the same way as Embodiments 2-1 and 2-2. Also, the metal identifying device of the present invention is not limited to the above-described embodiments. For example, an embodiment in which both the mount unit 202 and discharge electrode 203 are movable is possible.

The following describes metal identifying devices and metal identifying methods that identify the metal composition of a test object by reflection, as Embodiments 3-1 to 3-4 of the present invention.

Embodiment 3-1

Figure 15A:
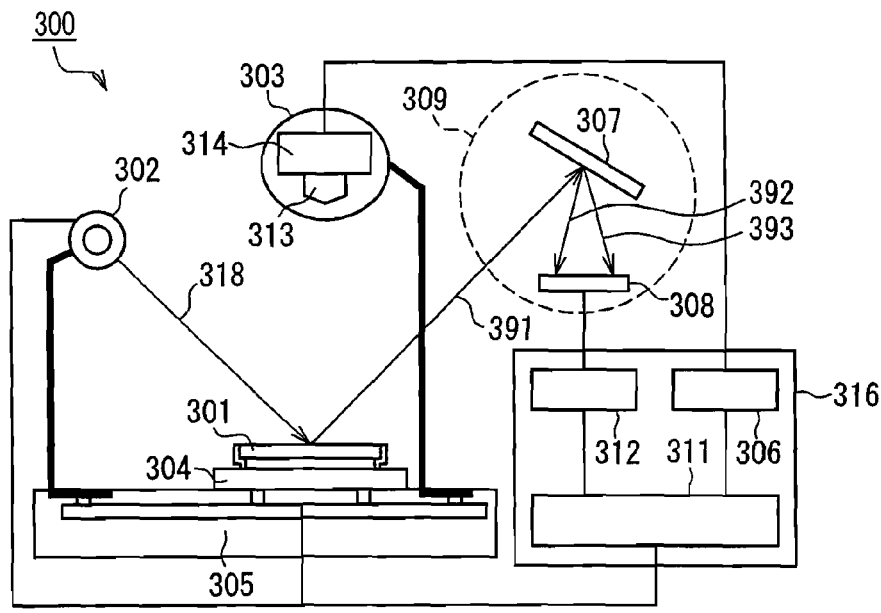
FIG. 15A is a schematic diagram showing an exemplary structure of a metal identifying device according to Embodiment 3-1 of the present invention.

FIG. 15A is a schematic diagram showing an exemplary structure of a metal identifying device according to Embodiment 3-1 of the present invention. The main constituent elements of a metal identifying device 300 shown in FIG. 15A are a light source 302, a position detection unit 303, a mount unit (sample placement unit) 304, a movement mechanism unit 305, a light reception unit 309, and a controller 316. The controller 316 includes a detected position storage unit 306, a movement mechanism control unit 311, and a spectrum comparison unit 312. In this embodiment, the light source 302 and light reception unit 309 correspond to a measurement unit, the controller 316 corresponds to a threshold value determination unit and a comparison/identification unit, the position detection unit 303 corresponds to a measurement position detection unit and a through-hole portion detection unit, and the movement mechanism unit 305 corresponds to a movement control unit.

The mount unit 304 is disposed above the movement mechanism unit 305, and can be moved in a planar direction by control of the movement mechanism unit 305. The mount unit 304 grips a metal member (test object) 301 that has a plurality of through-hole portions penetrating through the metal member. The light source 302 can irradiate a light beam 318 on the metal member 301. The light source 302 is preferably a light source that emits a white-light beam due to being able to cover all wavelength ranges of visible light. A xenon discharge light or the like can be used as the white light source due to having a property of emitting light that has relatively little wavelength dependency in the visible light range and due to emitting high-intensity light. The position detection unit 303 includes an image recognition device 314 and an imaging device 313, and is disposed above the mount unit 304. The imaging device 313 captures an image of the metal member 301, and the image recognition device 314 processes the captured image to detect positional coordinates etc. of through-hole portions in the metal member 301. The positional coordinates can be stored in the detected position storage unit 306 as two-dimensional position information. The movement mechanism control unit 311 controls the position of the light source 302 and/or mount unit 304 based on the position information stored in the detected storage unit 306 so that the light beam 318 is irradiated selectively on a portion of the metal member 301 other than the through-hole portions. Also, if the luminous flux area of the light beam 318 is larger than the area of a through-hole portion, the ratio of the through-hole portions to the measurement area in the metal member and/or the configuration of the through-hole portion is obtained based on, for example, the position information, and a threshold value can be determined by correcting and/or selecting a reference value (reference dispersion spectrum intensity) with use of the obtained ratio and/or configuration. Also, by causing the position information and movement mechanism unit 305 to work in cooperation, selection can be performed so that the presence of the through-hole portions 351 is minimized (the presence of the metal member 301 is maximized) in the luminous flux area of the light beam 318 that is irradiated on the metal member 301.

The light reception unit 309 includes a dispersion generation unit 307 and a linear image sensor 308, and can receive reflected light 391 that has reflected off the metal member 301. If the dispersion generation unit 307 of the light reception unit 309 includes a reflective diffraction grating that disperses the reflected light 391 by changing the angle of each wavelength component in the visible light range, the reflected light 391 is reflected by the diffraction grating and dispersed into reflected light 392 and 393 for respective wavelength components, and the reflected light 392 and 393 is received by the linear image sensor 308. For example, the ultraviolet light 393 that has a wavelength less than 400 nm and was obtained by the dispersion of the reflected light 391 is received on the right side of the linear image sensor 308, the infrared light 392 that has a wavelength of 800 nm or greater is received on the left side of the linear image sensor 308, and visible range light having a wavelength greater than or equal to 400 nm and less than 800 nm is received in the center portion of the linear image sensor 308. The metal composition of the metal member 301 can be identified by comparing the dispersion spectrum generated by the dispersion generation unit 307 and a reference dispersion spectrum stored in the spectrum comparison unit 312. Examples of the reference dispersion spectrum include metal-specific dispersion spectrums obtained based on the reflected light 391 generated by irradiating the light beam 318 on metal members whose metal composition is known in advance; spectrums selected, from among a plurality of spectrums prepared according to the ratio of the through-hole portions to the measurement area in the metal member and/or the configuration of the through-hole portion, based on the ratio of the through-hole portions in the metal member and/or the configuration of the through-hole portion; and spectrums obtained by correcting the metal-specific dispersion spectrums based on the ratio of the through-hole portions in the metal member and/or the configuration of the through-hole portion. The spectrum comparison unit 312 can obtain a reflection rate for each wavelength component with use of light quantity data for the light beam 318 and light quantity data for each wavelength component received by the linear image sensor 308. Also, the spectrum comparison unit 312 can compare the measurement values (reflection rates) of a plurality of test objects, and the metal composition of each test object may be identified. The spectrum comparison unit 312 may store, for example, light quantity data for each wavelength component when the light beam 318 is irradiated on a metal member 353.

The mount unit 304 and movement mechanism unit 305 may, for example, have the structures shown in FIGS. 10A and 10B, similarly to Embodiment 2-1. Also, when the light beam 318 irradiated on the shadow mask 201 passes through a through-hole portion, is reflected off the surface of the mount unit, and is received by the light reception unit 309 as reflected light, such reflected light from the mount unit becomes noise light. For this reason, from the viewpoint of eliminating noise light to improve the identification precision, it is preferable to, for example, grip the periphery of the metal member while applying tensile force to the metal member, and furthermore form a space between the metal member and the mount unit, perform antireflective coat processing on the surface of the mount unit, or the like. In order to identify the metal member 301 lacking projections on its surface, disposing the metal member 301 on the mount unit 304 in a condition of being gripped while tensile force is applied to the metal member 301 enables, for example, measuring the reflection rate of the metal member in a condition in which stray light has been reduced.

Instead of having a structure including the imaging device 313 and image recognition device 314, the position detection unit 303 may be an optical unit including a simple light emitting element and a light receiving element. In the case of having such as structure, the through-hole portions and metal portion of the metal member can be recognized by, for example, irradiating light from the light emitting element in a direction perpendicular to the metal member, and detecting changes in the quantity of reflected light with use of the light receiving element.

Figure 15B:
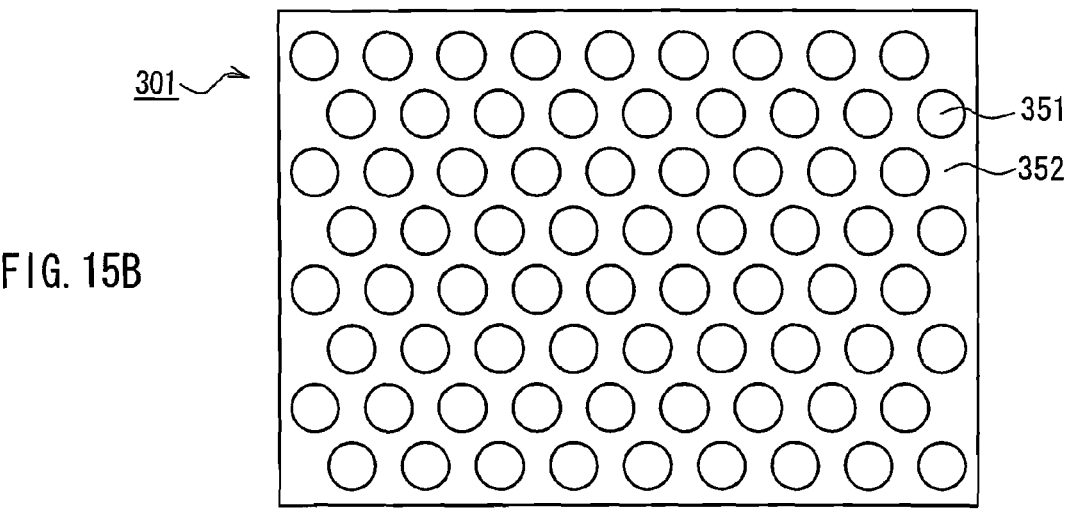
FIGS. 15B and 15C are plan views showing exemplary metal members.
Figure 15C:
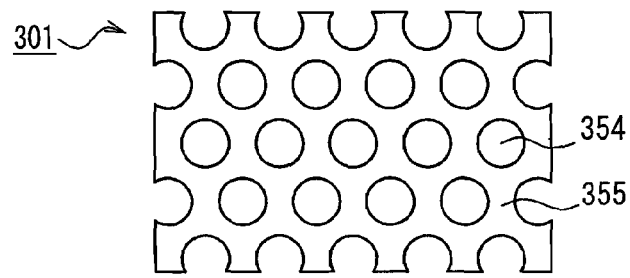

The metal identifying device 300 of the present Embodiment 3-1 can identify, for example, the type of the metal member 301 having a structure as shown in FIGS. 15B and 15C. FIGS. 15B and 15C are schematic diagrams showing exemplary configurations of the metal member 301. The metal member 301 of FIG. 15B has a structure in which all through-hole portions 351 are surrounded by a metal portion 352, and all of the through-hole portions 351 have substantially the same configuration. However, the metal member 301 of FIG. 15C has a structure in which part of through-hole portions 354 that are positioned in the outer periphery portion of the metal member are not surrounded by the metal portion 352, and through-hole portions 354 positioned in the outer periphery portion are different from through-hole portions 354 positioned toward the interior.

Figure 16:
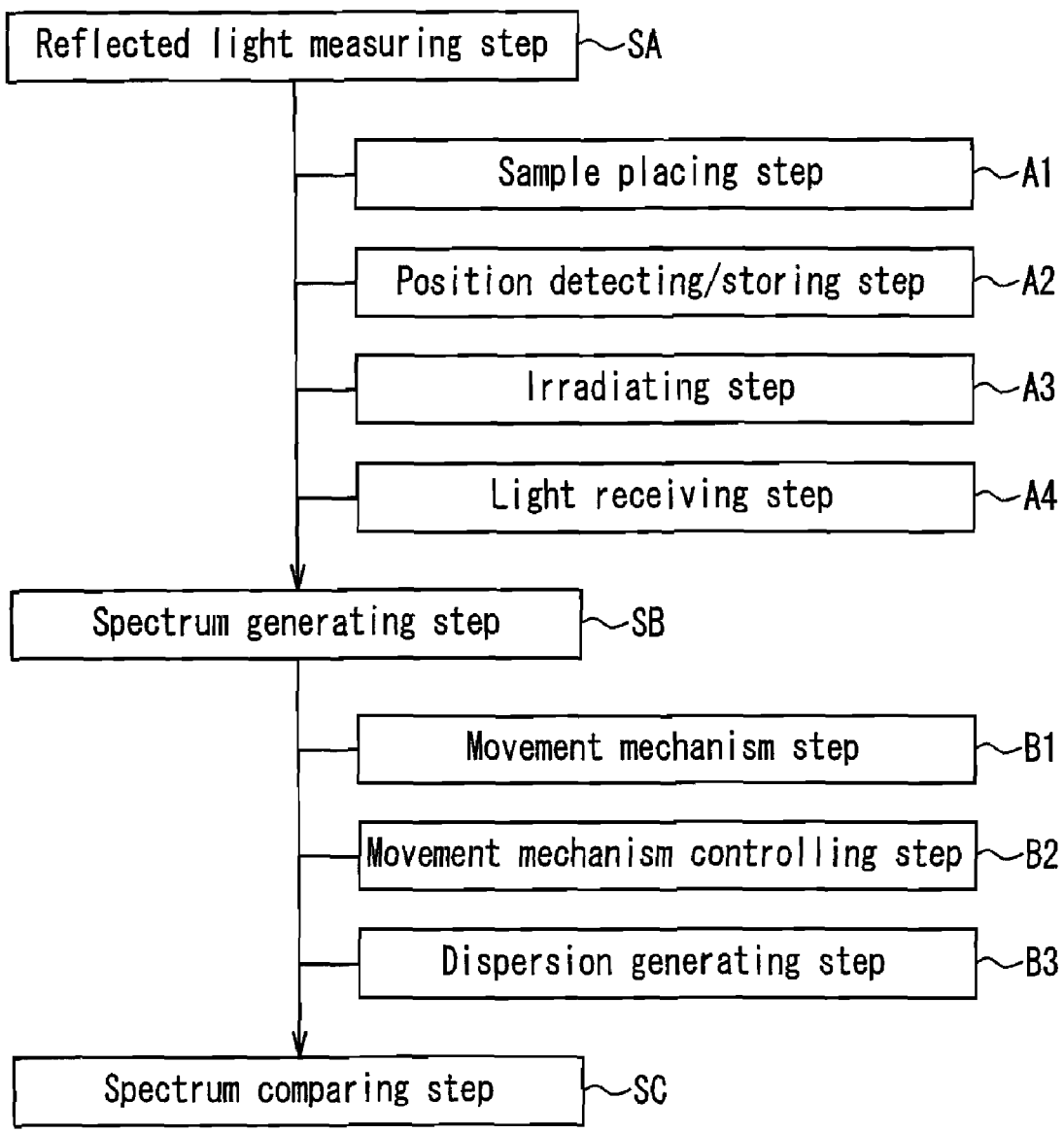
FIG. 16 is a flowchart showing an exemplary metal identifying method according to Embodiment 3-1 of the present invention.

The following describes the metal identifying method of the present Embodiment 3-1 with reference to FIG. 15 and FIG. 16. FIG. 16 is a flowchart showing an exemplary metal identifying method according to the present Embodiment 3-1. The identifying method of the present Embodiment 3-1 includes a reflected light measuring step (SA), a spectrum generating step (SB), and a spectrum comparing step (SC). The reflected light measuring step (SA) includes a sample placing step (A1), a position detecting/storing step (A2), an irradiating step (A3), and a light receiving step (A4), and the spectrum generating step (SB) includes a movement mechanism step (B1), a movement mechanism controlling step (B2), and a dispersion generating step (B3).

First, the metal member (test object) 301 is disposed on the mount unit 304 (A1). Next, the positions of the through-hole portions 351 and 354 and the metal portion 352 and a metal portion 355 in the metal member 301 are detected with the use of the imaging device 313 and image recognition device 314, and position information indicating the detected positions is stored in the position detection unit 306 (A2). Based on the position information, the movement mechanism control unit 311 moves at least one of the light source 302 and the movement mechanism unit 305 in order to perform adjustment so that the light beam 318 is irradiated on the metal portions 352 and 355 of the metal member 301. Then, the light beam 318 having a diameter of, for example, approximately 1 mm is irradiated toward the metal member 301 (A3). The reflected light 391 that has reflected off the metal member 301 is received by the light reception unit 309 (A4).

Next, processing moves to the spectrum generating step (SB). In the movement mechanism step (B1), either the light reception unit 309 and light source 302, or the mount unit 304 is moved, and in the movement mechanism controlling step (B2), control is performed so that the light beam 318 is selectively irradiated on the metal portions 352 and 355 of the metal member 301. In the dispersion generating step (B3), a dispersion spectrum is generated for the reflected light 391 received by the light reception unit 309. According to the position detecting/storing step (A2), movement mechanism step (B1), and movement mechanism controlling step (B2), even if the luminous flux area of the irradiated light is smaller than the area of a through-hole portion, moving the light source 302 and/or the mount unit 304 etc. based on the position information enables irradiating the irradiated light so that as much metal portion as possible is included in the spot of the irradiated light. This enables further increasing the intensity of the reflected light, thereby improving the identification precision.

Processing then moves to the spectrum comparing step (SC). The metal composition of the metal member 301 can be identified by comparing a dispersion spectrum obtained by measurement and, for example, a reference dispersion spectrum. Here, a plurality of reference dispersion spectrums may be prepared according to the ratio of the through-hole portions to the measurement area in the metal member and/or the configuration of the through-hole portion, and the reference dispersion spectrum that is used may be selected from among the prepared reference dispersion spectrums using the ratio of the through-hole portions and/or the configuration of the through-hole portion. Also, the reference dispersion spectrum may be obtained by performing correction on metal-specific reference dispersion spectrums using the ratio of the through-hole portions and/or the configuration of the through-hole portion. In other words, if the test object is a metal member having a plurality of through-hole portions penetrating through the metal member, the obtained reflection rate differs depending on the ratio of the through-hole portions to the measurement area in the metal member. For this reason, a threshold value is determined by, for example, determining a coefficient (ratio coefficient) based on the ratio of the through-hole portions, and applying the ratio coefficient to metal-specific reference reflection rates (reference values). Correcting the reference values in this way, is preferable since noise components are not superimposed due to signal amplification, and the identification precision can be improved. Also, the reflection rate (measurement value) of the test object may be corrected using the above-described coefficient or the like. In the case of correcting the measurement value in this way, for example, amplifying the numerical value of the measurement value enables direct comparison with the reference reflection rates. Also, the method of correcting the measurement value is useful in, for example, a case in which the ratio of the through-hole portions in the metal member is high, that is to say, the ratio of the metal portion in the metal member is low.

Figure 17:
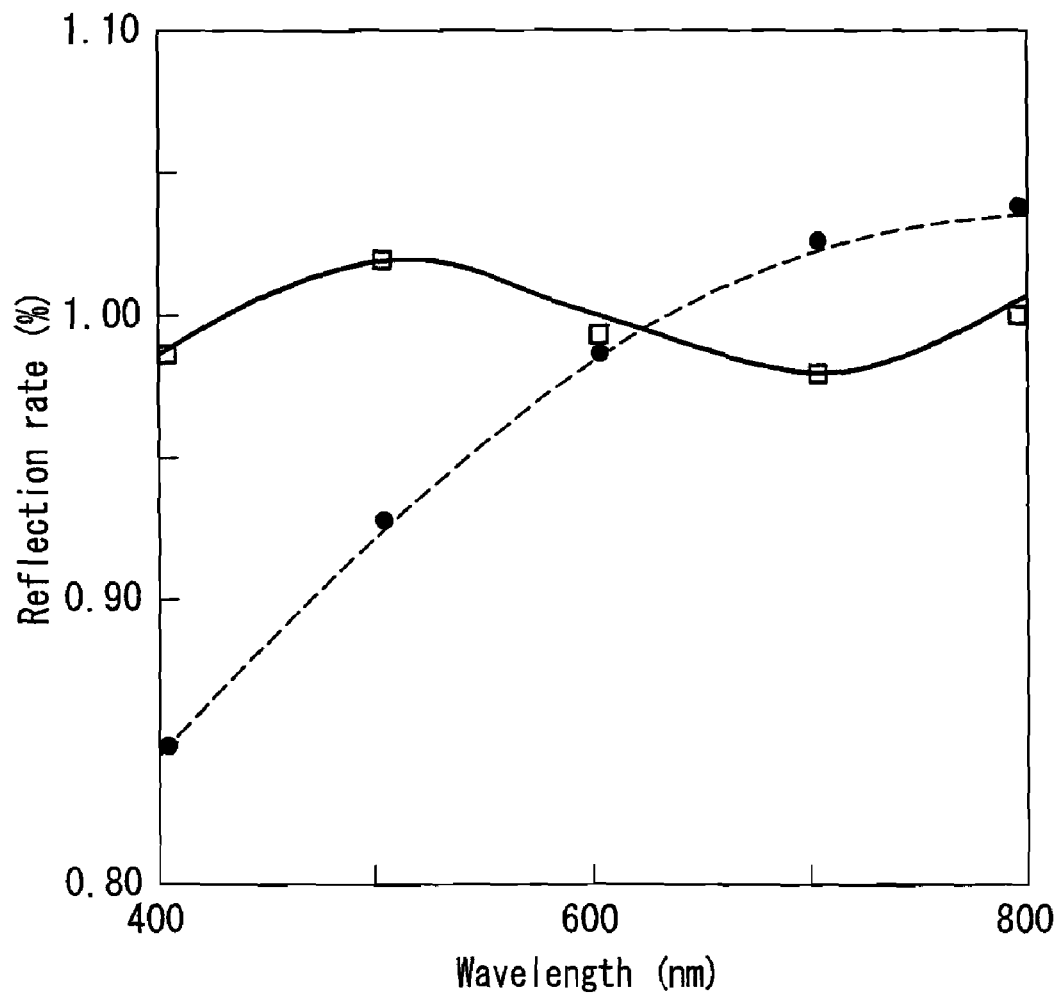
FIG. 17 is a graph showing exemplary dispersion spectrums of reflection rates obtained in Embodiment 3-1 of the present invention.

FIG. 17 shows a dispersion spectrum of reflection rates of a CRT shadow mask obtained using the metal identifying device of the present Embodiment 3-1. In FIG. 17, the spectrum indicated by a solid line is an iron material dispersion spectrum, and the spectrum indicated by a broken line is an Invar alloy material dispersion spectrum. It can be seen that although the surface reflection rate is extremely small at around 1% in both spectrums, the reflection rate dispersion spectrum differs greatly between the iron material and Invar alloy material. A comparison of the reflection rates in the wavelength range of 400 nm to 800 nm shows that although the reflection rate of the iron material is substantially constant at around 1%, the reflection rate of the Invar alloy material persistently rises from 400 nm toward the long-wavelength side. For this reason, if the test object is either the iron material or the Invar alloy material, for example, measurement is performed using measurement wavelengths in a wavelength range of 400 nm to 800 nm that substantially covers the visible light range, and the range is compared, thereby enabling identifying the metal composition of the test object based on differences in the above-described spectrums.

Note that although the above example describes a case of measuring reflection rates, it is possible to, for example, measure a light intensity dispersion spectrum by disposing a reference plate (not shown) having a reflection rate close to 100% and little wavelength dependency at the position of the metal member 301.

Embodiment 3-2

Figure 18A:
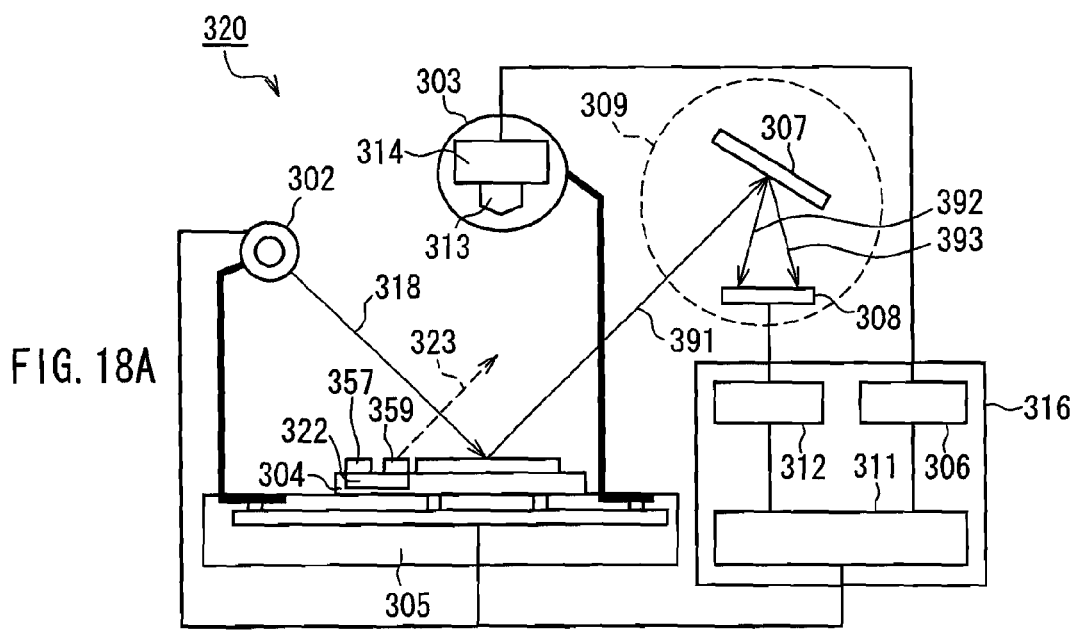
FIG. 18A is a schematic diagram showing an exemplary structure of a metal identifying device according to Embodiment 3-2 of the present invention.

FIG. 18A is a schematic diagram showing an exemplary structure of a metal identifying device according to Embodiment 3-2 of the present invention. A metal identifying device 320 of FIG. 18A has the same structure as the metal identifying device 300 of Embodiment 3-1, with the exception that the mount unit 304 includes a monitor metal member placing unit 322, and monitor metal members 357 and 359 can be disposed in addition to the metal member (test object) 301. The monitor metal members 357 and 359 are constituted from, for example, a metal assumed to be possible metals constituting the metal member 301 that is the test object. According to the metal identifying device of the present Embodiment 3-2, since the monitor metal members 357 and 359 can be disposed beside the metal member 301, irradiating both the metal member 301 that is the test object and the monitor metal members 357 and 359 with a light beam enables measuring metal-specific dispersion spectrums of the monitor metal members 357 and 359 under the same conditions as the metal member 301 that is the test object. Given that all the obtained dispersion spectrums are dispersion spectrums measured under the same conditions, the metal identification precision can be improved by performing comparison analysis on the reflection dispersion spectrums. Also, since the measurement of the test object and the measurement of the dispersion spectrums that are to be references (hereinafter, also called the "metal-specific dispersion spectrums") can be performed at the same time, there is no need to measure the dispersion spectrums to be used as the reference values in advance, and the metal composition of the test object can be identified simply and speedily. Note that although the present embodiment describes a case of using two types of metal members as the monitor metal members, it is sufficient to determine the number of the monitor metal members appropriately according to the types of metal compositions that are to be identified.

In the metal identifying device 320 of the present Embodiment 3-2, first the mount unit 304 is moved using the movement mechanism unit 305, and the light beam 318 from the light source 302 is irradiated on the surfaces of the monitor metal members 357 and 359. Reflected light 323 is received by the light reception unit 309, and the dispersion generation unit 307 generates a metal composition dispersion spectrum for each of the monitor metal members 357 and 359. Next, the mount unit 304 is moved using the movement mechanism unit 305, the light beam 318 from the light source 302 is irradiated toward the metal member 301, and the dispersion generation unit 307 generates a dispersion spectrum based on the reflected light 391 from the metal member 301. The spectrum comparison unit 312 compares the dispersion spectrum based on the reflected light 391 from the metal member 301 and the reference dispersion spectrums, thereby enabling identifying the metal composition of the metal member 301. Examples of the reference dispersion spectrum include dispersion spectrums obtained from the monitor metal members 357 and 359; spectrums selected, from among a plurality of spectrums prepared according to the ratio of the through-hole portions to the measurement area in the metal member and/or the configuration of the through-hole portion, based on the ratio of the through-hole portions in the metal member and/or the configuration of the through-hole portion; and spectrums obtained by correcting the dispersion spectrums obtained from the monitor metal members, based on the ratio of the through-hole portions in the metal member and/or the configuration of the through-hole portion. Also, similarly to Embodiment 3-1, the movement mechanism control unit 311 performs overall control of the metal identifying device 320 by causing the function units etc. to operate in conjunction and cooperation with each other.

Figure 18B:
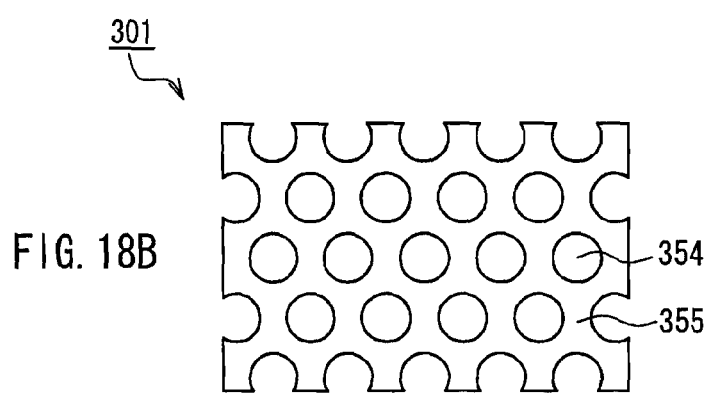
FIG. 18B is a plan view showing an exemplary metal member.
Figures 18C, 18D:
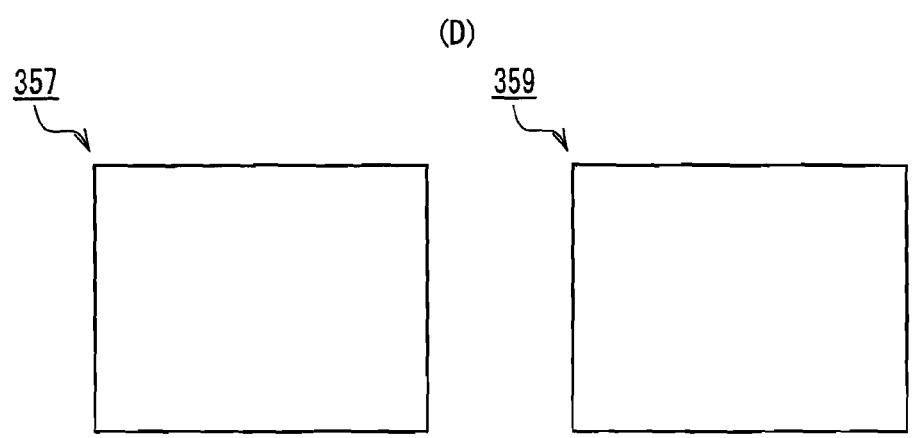
FIGS. 18C and 18D are plan views showing exemplary monitor metal members.
Figure 19:
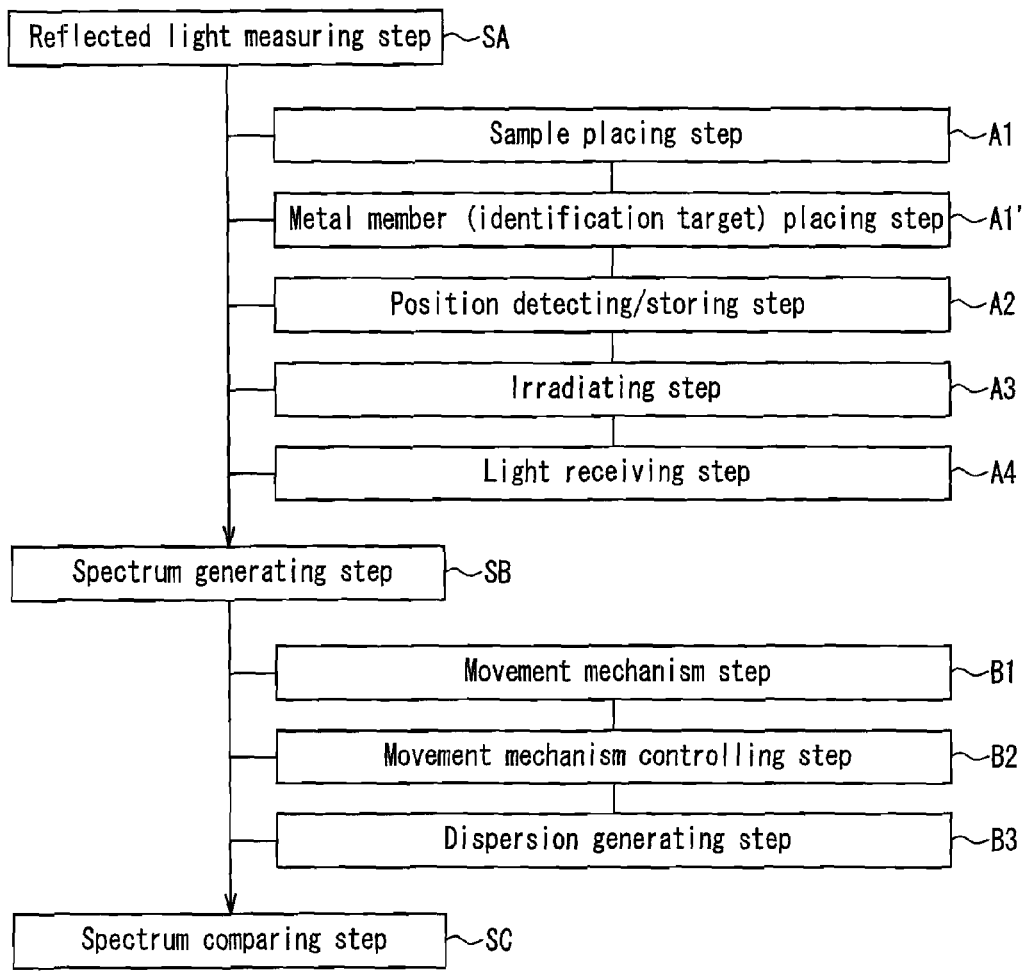
FIG. 19 is a flowchart showing an exemplary metal identifying method according to Embodiment 3-2 of the present invention.

The following describes a metal identifying method using the metal identifying device 320 of the present Embodiment 3-2 with reference to FIGS. 18 and 19. FIG. 19 is a flowchart showing an exemplary metal identifying method using the metal identifying device 320 according to the present Embodiment 3-2. This identifying method is the same as the identifying method using the metal identifying device 300 of Embodiment 3-1, with the exception that the reflected light measuring step (SA) includes a test object (identification target) or monitor metal member placing step (A1'), and the spectrum comparing step (SC) involves identifying a metal composition using the metal-specific dispersion spectrums (intensities) of the monitor metal members as reference values.

In other words, first the metal member 301 and monitor metal members 357 and 359 are disposed on the mount unit 304 (A1, A1'). The position detecting/storing step (A2), irradiating step (A3), light receiving step (A4), and spectrum generating step (SB) are performed in the same way as in Embodiment 3-1, with the exception that measuring is performed for the monitor metal members 357 and 359 in addition to the metal member 301. Processing then moves to the spectrum comparing step (SC) in which the obtained dispersion spectrum (intensity) and monitor metal member dispersion spectrums (intensities) are compared, thereby enabling identifying the metal composition of the metal member 301.

For example, if the metal member 301 that is the test object is a CRT shadow mask, an iron material metal member and an Invar alloy material metal member are prepared as the monitor metal members 357 and 359. The dispersion spectrums of the monitor metal members are, for example, similar to the graph of FIG. 17. The dispersion spectrum of the metal member 301 that is the test object is measured as described above, the obtained dispersion spectrum and the dispersion spectrums of the monitor metal members are compared, and if the obtained dispersion spectrum is close in shape to the Invar alloy material dispersion spectrum, the metal composition of the metal member 301 (test object) can be identified as the Invar alloy material. However, if the obtained dispersion spectrum is close in shape to iron material dispersion spectrum, the metal composition of the metal member 301 (test object) can be identified as the iron material. Note that the metal composition of the metal member (test object) is not limited to iron or Invar alloy. Any metals having different dispersion spectrums based on reflection rates can be identified.

The range of wavelengths measured in the light reception unit 307 and dispersion spectrum 308 and the range of wavelengths in the dispersion spectrums compared in the spectrum comparison unit 312 may be a specified wavelength range. Also, two or more types of specified wavelength ranges may be combined. If the metal constituting the test object has a range of wavelengths showing a unique spectrum shape or reflection rates, a metal composition can be identified speedily and highly precisely by only performing a comparison with respect to this range. For example, in the case of the iron material and Invar alloy material, as shown in the graph of FIG. 17, using the wavelength of 600 nm as the boundary, the difference in reflection rates is small on the long-wavelength side, whereas on the short-wavelength side, the difference becomes significantly larger as the wavelength becomes shorter. In other words, the difference between the reflection rate of the iron material and the reflection rate of the Invar alloy material is clearer in the wavelength range of 400 nm to 580 nm inclusive. For this reason, for example, if the metal composition is the iron material or the Invar alloy material, as in a CRT shadow mask, the metal composition can be identified by comparing reflection rates for this wavelength range. Also, it is preferable to perform correction based on the ratio of the through-hole portions to the measurement area in the metal member.

Embodiment 3-3

Figure 20A:
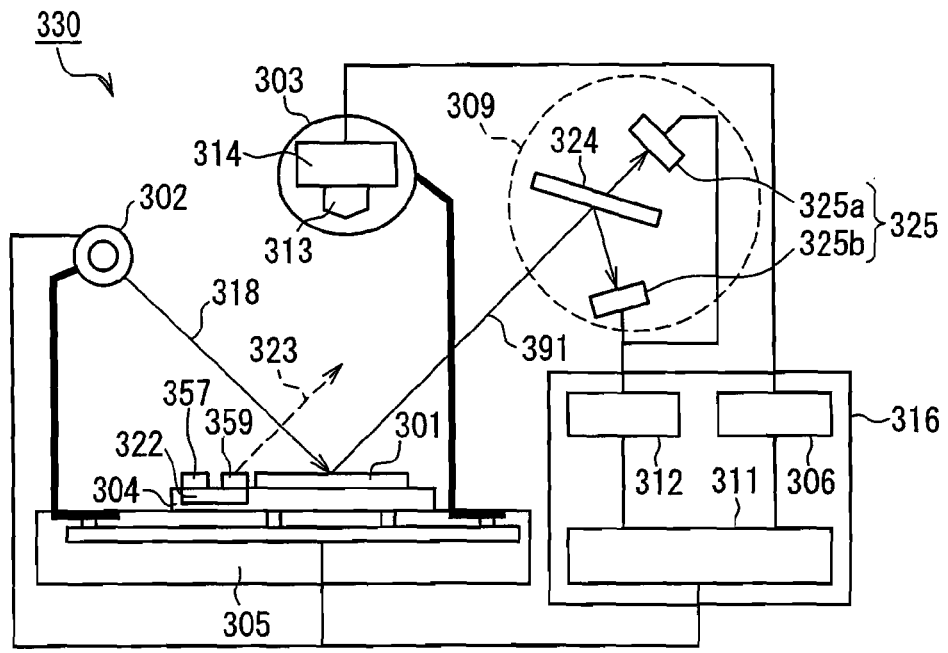
FIG. 20A is a schematic diagram showing an exemplary structure of a metal identifying device according to Embodiment 3-3 of the present invention.
Figure 20B:
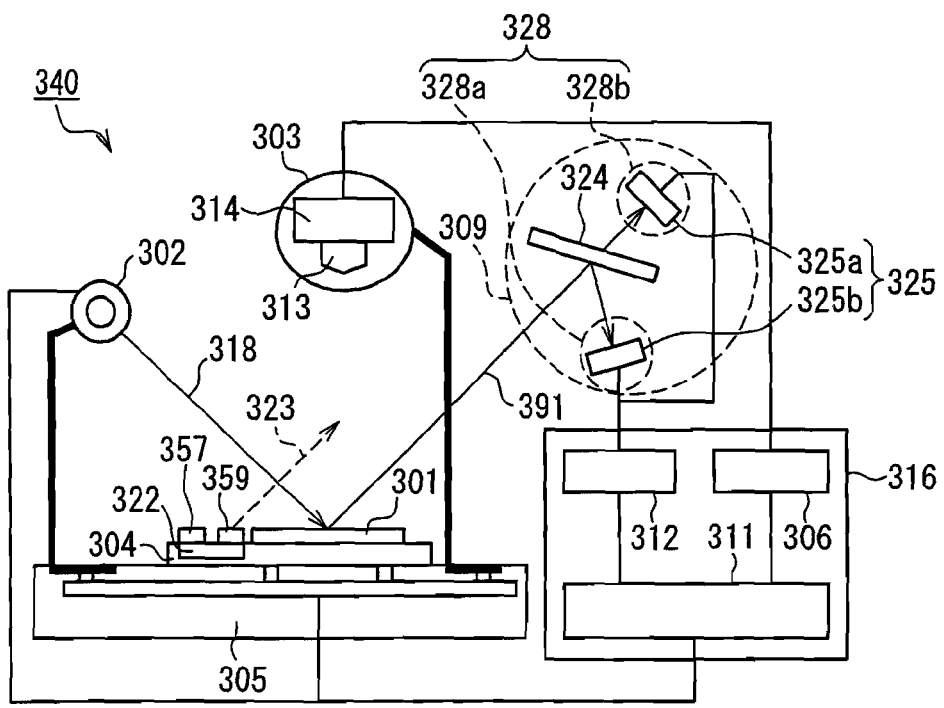
FIG. 20B is a schematic diagram showing another exemplary structure of the metal identifying device according to Embodiment 3-3 of the present invention.

FIG. 20A is a schematic diagram showing an exemplary structure of a metal identifying device according to Embodiment 3-3 of the present invention, and FIG. 20B is a schematic diagram showing another exemplary structure of the metal identifying device of Embodiment 3-3 of the present invention. A metal identifying device 330 of FIG. 20A and a metal identifying device 340 of FIG. 20B both have the same structure as the metal identifying device 320 of Embodiment 3-2, with the exception that the light reception unit 309 is a light receiving element or an integrating sphere.

The light reception unit 309 of the metal identifying device 330 shown in FIG. 20A includes a dichroic mirror 324 and light receiving elements 325 (325a, 325b). The inclusion of the two types of light receiving elements 325a and 325b enables simply and speedily measuring a dispersion spectrum in a specified wavelength range, instead of measuring a reflection rate dispersion spectrum in all ranges of the visible light range. This structure is particularly useful in, for example, a case of identifying test objects whose metal compositions have a clear difference in reflection rates in a specified wavelength range, as in the case of the iron material and the Invar alloy material. In the case of identifying the iron material and the Invar alloy material, the light receiving element 325a receives reflected light that is only in a band in the vicinity of the wavelength of 450 nm, the light receiving element 325b receives reflected light in other wavelength ranges, and the dispersion spectrum of each range is compared with a reference dispersion spectrum, thereby enabling identifying whether the metal composition is the iron material or the Invar alloy material. For example, a dichroic mirror whose surface is coated with a dielectric multilayer film that transmits only light in a band in the vicinity of the wavelength of 450 nm and reflects light in other ranges can be used as the dichroic mirror 324.

The light reception unit 309 of the metal identifying device 340 shown in FIG. 20B includes the dichroic mirror 324 and integrating spheres 328 (328a, 328b), and the light receiving elements 325a and 325b are disposed in the integrating spheres 328a and 328b respectively. Due to disposing the light receiving elements in the integrating spheres, light that has reflected off the light receiving elements is reflected off the interior of the integrating spheres and is again received by the light receiving elements, thereby improving the sensitivity of the light receiving elements. For this reason, metals can be identified simply, speedily, and highly precisely even if, for example, the amount of reflected light from the metal member is small, that is to say, the reflection rate is low.

Metals can be identified by the metal identifying devices 330 and 340 of the present Embodiment 3-3 using the same identifying method as in Embodiments 3-1 and 3-2.

Embodiment 3-4

Figure 21:
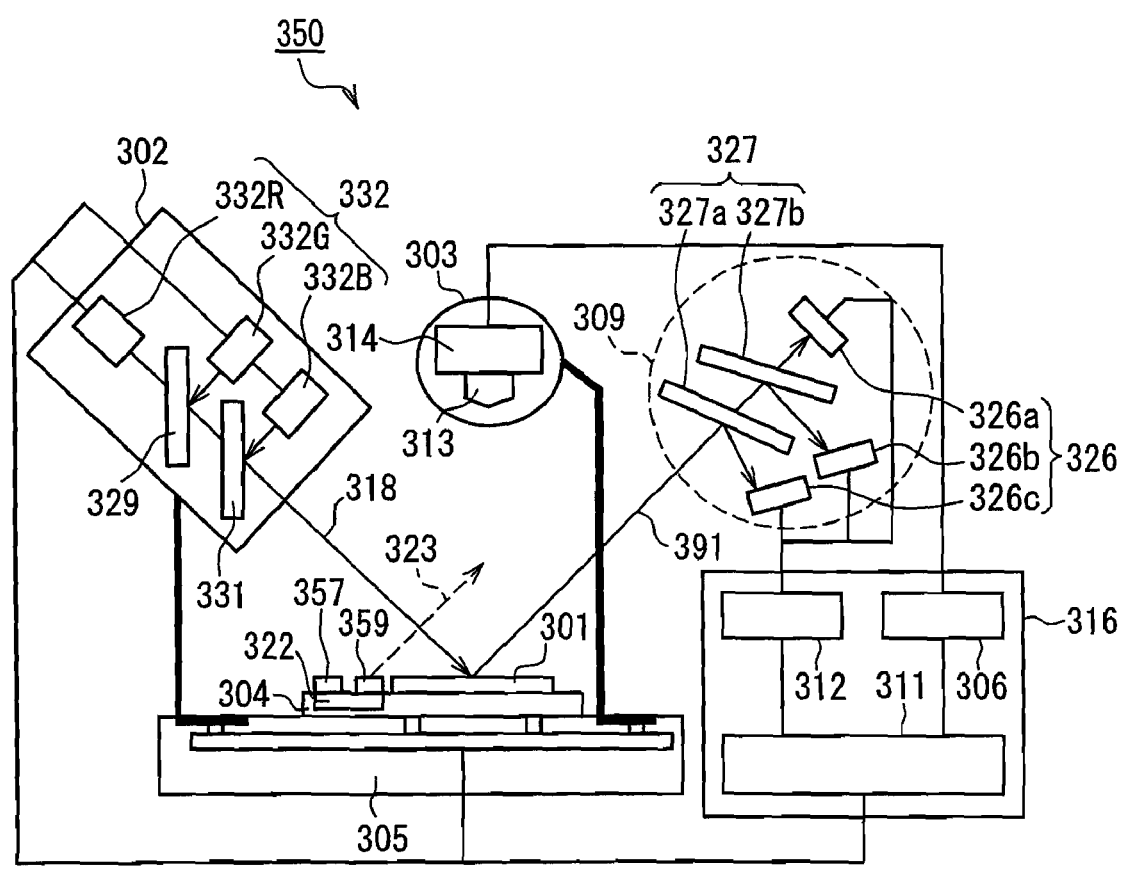
FIG. 21 is a schematic diagram showing an exemplary structure of a metal identifying device according to Embodiment 3-4 of the present invention.

FIG. 21 is a schematic diagram showing an exemplary structure of a metal identifying device according to Embodiment 3-4 of the present invention. A metal identifying device 350 of FIG. 21 has the same structure as the metal identifying device 320 of Embodiment 3-2, with the exception of the light source 302 and light reception unit 309.

The light source 302 includes a high intensity light source 332 in which a red light source (R light source) 332R, a green light source (G light source) 332G, and a blue light source (B light source) 332B are included, and dichroic mirrors 329 and 331. In the light source 302, light sources having three different wavelengths (the R light source 332R, G light source 332G and B light source 332B) irradiate light, and the dichroic mirrors 329 and 331 focus the irradiated light into the light beam 318 that has a single optical axis and irradiates the light beam 318 on the metal member 301 and monitor metal members 357 and 359. Laser light sources such as LEDs and semiconductor lasers can be used as the R light source 332R, G light source 332G and B light source 332B. Using LEDs or semiconductor lasers as the light source 302 makes it possible, for example, easily to obtain a high intensity light beam having a diameter of 100 μm or less, and improve the identification precision, with a simple optical member. Also, the size of the light source can be reduced, thereby enabling a reduction in the size of the metal identifying device. LEDs preferably are used as the R light source 332R, G light source 332G and B light source 332B from the viewpoint of the ability to narrow the light beam 318 into a very small spotlight and further improve the identification precision. Also, semiconductor lasers preferably are used as the R light source 332R and B light source 332B from the viewpoint of being small and highly efficient, and having low power consumption and being inexpensive. Note that although an example of using a light source including three types of light sources, namely the R light source 332R, G light source 332G and B light source 332B, as the light source 302 has been described, the present invention is not limited to this. It is sufficient for the light source 302 to include at least one light source.

The light reception unit 309 includes dichroic mirrors 327 (327a, 327b) and light receiving elements 326 (326a, 326b, 326c). According to this light reception unit 309, the reflected light in different wavelength ranges irradiated from the R light source 332R, G light source 332G and B light source 332B can be received by the separate light receiving elements 326a, 326b and 326c respectively. For example, in the reflected light 391 that has arrived at the light reception unit 309, only the blue light in the vicinity of the wavelength of 450 nm is reflected off the dichroic mirror 327a and is received by the light reception unit 326c. In the light that has passed through the dichroic mirror 327a, only green light in the vicinity of the wavelength of 530 nm is reflected off the dichroic mirror 327b and is received by the light reception unit 326b. In the light that has passed through the dichroic mirror 327b, light in the wavelength range that is longer than green light is received by the light receiving element 326a.

The metal identifying device 350 of the present Embodiment 3-4 includes the light source 302 that irradiates light in specified wavelength ranges and the light receiving elements 326 that can receive the light in the wavelength ranges, thereby enabling, for example, measuring a limited wavelength range of a light beam, and simple, speedy, and highly precise identification of a metal composition. Also, the metal identifying device 350 of the present Embodiment 3-4 can identify a metal using, for example, the same identifying method as in Embodiments 3-1 and 3-2.

The following describes metal identifying devices and metal identifying methods that identify the metal composition of a test object by luster, as Embodiments 4-1 to 4-4 of the present invention.

Embodiment 4-1

Figure 22A:
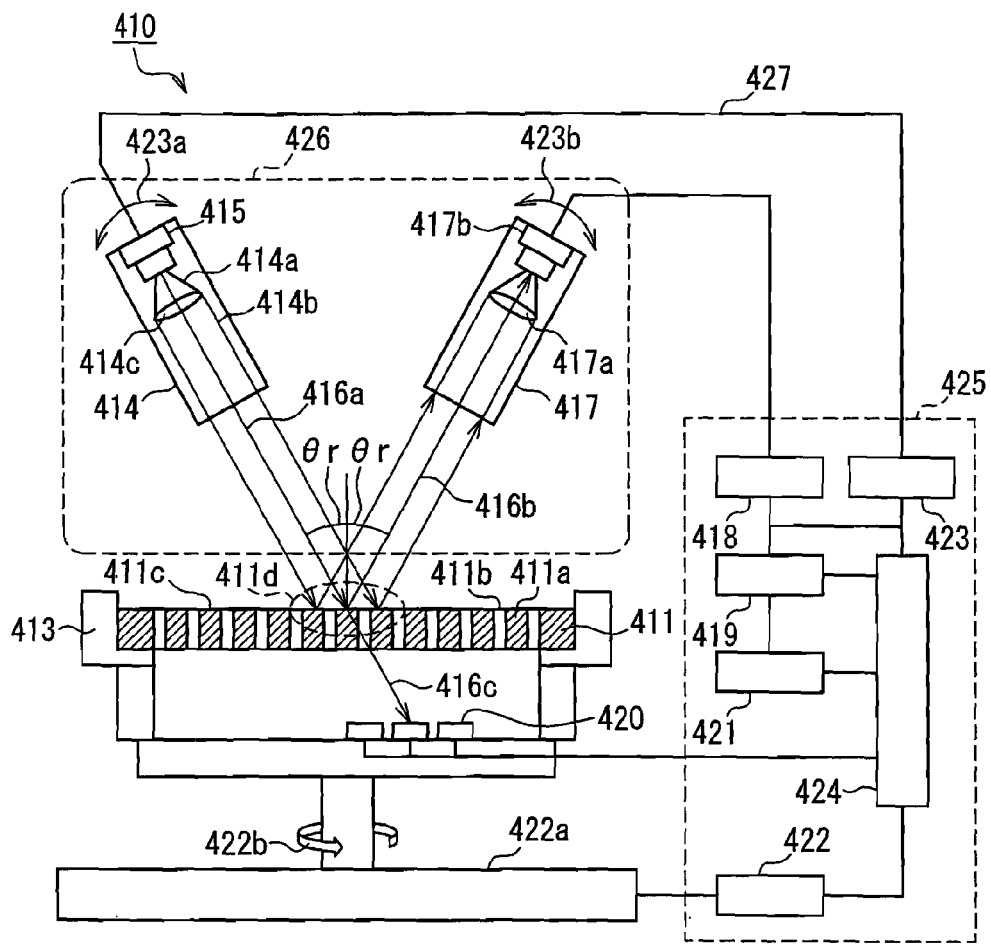
FIG. 22A is a schematic diagram showing an exemplary structure of a metal identifying device according to Embodiment 4-1 of the present invention.
Figure 22B:
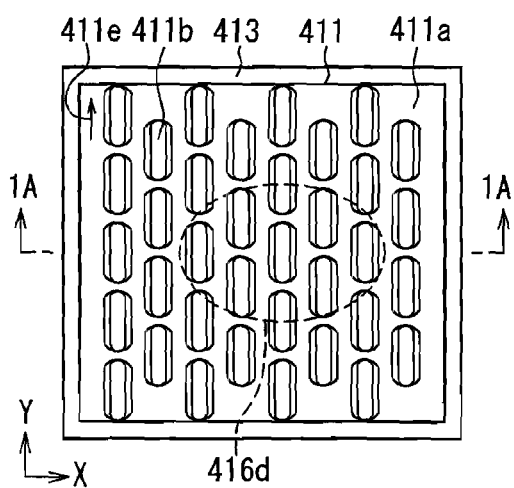
FIGS. 22B and 22C are plan views showing exemplary CRT shadow masks.
Figure 22C:
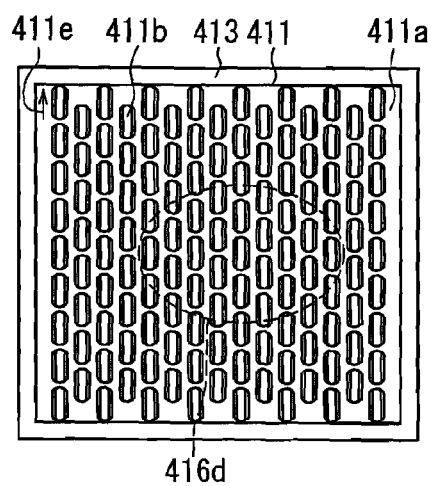

FIG. 22A is a schematic diagram showing an exemplary structure of a metal identifying device according to Embodiment 4-1 of the present invention, and FIGS. 22B and 22C are plan views showing exemplary press masks disposed on a mount unit 413. The mount unit 413 and a metal member 411 in FIG. 22A correspond to a cross-sectional view taken along a line 1A-1A in FIG. 22B.

The main constituent elements of a metal identifying device 410 in FIG. 22A are the mount unit 413, an irradiation unit 414, a luster intensity measurement unit 417, and a controller 425. In this embodiment, the irradiation unit 414 and luster intensity measurement unit 417 correspond to a measurement unit, and the controller 425 corresponds to a threshold value determination unit and a comparison/identification unit.

The mount unit 413 is disposed above a support unit 422a, and the metal member (test object) 411 having a plurality of through-hole portions penetrating through the metal member can be fixed on and gripped by the mount unit 413. The irradiation unit 414 includes a light source 415 and a collimating lens 414c. Irradiated light 414a irradiated from the light source 415 is converted into a parallel light beam 414b by the collimating lens 414c, and a light beam 416a can be irradiated on the metal member 411 at a predetermined angle θr. A light detection unit 420 is disposed between the mount unit 413 and support unit 422a, and by receiving the light beam 416a irradiated from the light source 415, the light detection unit 420 can detect a ratio (ratio of the through-hole portions) Rh of through-hole portions 411b to an irradiation area 411d in the metal member 411. The luster intensity measurement unit 417 includes a condensing lens 417a and a light reception unit 417b. The luster intensity measurement unit 417 measures a luster intensity by condensing reflected light 416b from the metal member 411 with use of the condensing lens 417a, and thereafter receiving the reflected light 416b with use of the light reception unit 417b.

The controller 425 includes a comparison circuit unit 418, a comparison/identification unit 419, a data unit 421, a direction modification unit 422, an angle modification unit 423, and a control unit 424. These units are connected by cables or the like. Via the cable 427 or the like, the angle modification unit 423 is connected to the irradiation unit 414, the comparison circuit unit 418 is connected to the luster intensity measurement unit 417, the control unit 424 is connected to the light detection unit 420, and the direction modification unit 422 is connected to the support unit 422a. The comparison circuit unit 418 compares an obtained luster intensity and a threshold value, and the comparison/identification unit 419 identifies the metal composition of the metal member based on the result of the comparison. The data unit 421 can store reference values etc. used by the comparison circuit unit 418. Examples of the reference values include reference luster intensities and luster intensities originating from the metal composition of the metal member 411. Examples of the reference luster intensities include metal-specific luster intensities obtained based on the reflected light 416b generated by irradiating the light beam 416a on metal members whose metal composition is known in advance; luster intensities selected, from among a plurality of luster intensities prepared according to the ratio of the through-hole portions to the measurement area in the metal member and/or the configuration of the through-hole portion, based on the ratio of the through-hole portions and/or the configuration of the through-hole portion; and luster intensities obtained by correcting the metal-specific light emission intensities based on the ratio of the through-hole portions in the metal member and/or the configuration of the through-hole portion.

As shown in FIG. 22A, the light detection unit 420 may be disposed on the side of the metal member 411 that is opposite to the light source 415, or may be disposed on the same side as the light source 415. If the light detection unit 420 is disposed on the side opposite to the light source 415, the through-hole ratio Rh can be detected by, for example, irradiating the light beam 416a in a direction perpendicular to a surface 411c of the metal member 411, and receiving a light beam 416c that has passed through the through-hole portions 411b. Specifically, first the light beam 416a is irradiated without the metal member 411 being disposed on the mount unit 413, and an intensity is measured. Next, the light beam 416a is irradiated with the metal member 411 being disposed on the mount unit 413, and an intensity is measured. The through-hole ratio Rh can be quantitatively calculated with use of the intensities from before and after the disposition of the metal member 411. Also, as shown in FIG. 20A, disposing a plurality of light detection units 420 enables performing detection without moving the irradiation unit 414 etc., even if, for example, the irradiating angle θr of the light beam 416a varies. On the other hand, if the light detection unit 420 is disposed on the same side as the light source 415, the through-hole ratio Rh can be detected by, for example, irradiating the light beam 416a on the surface 411c of the metal member 411, and receiving the reflected light 416b that has reflected off the metal portion 411 of the metal member 411. In this case, a configuration in which the light detection unit 420 is disposed in the luster intensity measurement unit 417 and the light detection unit 420 is disposed on the same side as the light source 415 enables, for example, performing measurement without changing the angle etc. of the light source 415 both when detecting the through-hole ratio Rh of the metal member 411 and measuring the luster intensity.

The through-hole ratio Rh obtained as described above can be used in, for example, determining the threshold value to be used by the comparison circuit unit 418, and amplification degree optimization in a case of the control unit 424 controlling the current supplied to the light source 415 or amplifying a signal generated by the detection performed by the light detection unit 420 or the luster intensity measurement unit 417. In other words, if the test object is a metal member having a plurality of through-hole portions penetrating through the metal member, the obtained luster intensity is different depending on the through-hole ratio Rh. For this reason, if the metal-specific reference luster intensity is used as the threshold value without modification, there are cases in which the metal composition cannot be identified sufficiently. For this reason, in the metal identifying device 410 of the present Embodiment 4-1, the threshold value is determined by, for example, the comparison circuit unit 418 correcting the metal-specific reference luster intensity based on the through-hole ratio Rh or the like. This determining method may involve, for example, determining correction data (a threshold value) that has been calculated in advance based on the configuration of the through-hole portion and the through-hole ratio Rh (the type of the shadow mask), determining a coefficient to be applied to the metal-specific reference luster intensity, or calculating a threshold value from the specific luster intensity and coefficient. Also, the luster intensity (measurement value) of the test object may be corrected using the above-described coefficient or the like. The method of correcting the measurement value in this way enables performing a comparison with the reference luster intensity by, for example, amplifying the numerical value of the measurement value. However, correcting the reference value is normally preferable due to avoiding the superposition of noise components resulting from signal amplification and improving the identification precision. The method of correcting the measurement value is useful in, for example, a case in which the through-hole ratio Rh in the metal member is high, that is to say, the ratio of the through-hole portions in the metal member is low.

As shown in FIGS. 22B and 22C, there are differences in the size of the through-hole portions 411b and the through-hole ratio Rh of press masks depending on the screen size of the CRT display to be used. For this reason, the number of through-hole portions 411b in an irradiated light spot (the irradiated area) 416d and the through-hole ratio Rh are different depending on the screen size, that is to say, the size of the shadow mask.

The mount unit 413, for example, may include a function for gripping the metal member 411 by applying tension or the like, or may be a structure (placement table) on which the metal member 411 merely is placed. If the mount unit 413 includes the gripping function, it is possible to suppress the detection of noise components in the luster intensity measurement unit 417 that appear along with reflected light of the light beam 416c that has passed through the through-hole portions 411b of the metal member 411. On the other hand, if the mount unit 413 is a placement table, for example, the placement table is preferably given an antireflective coating or colored black from the viewpoint of eliminating the aforementioned noise components to improve the identification precision. Also, if the metal member is a CRT shadow mask, there are cases in which the quantity of light that is received by the luster intensity measurement unit 417 is low since the test object deforms and loses its flatness at the time of measurement, due to the metal composition being identified after disassembly of the CRT. For this reason, the mount unit 413 preferably includes a structure for applying tensile force to the metal member 411 from the viewpoint of increasing the detection precision by increasing the quantity of light that is received by the luster intensity measurement unit 417.

The direction modification unit 422 can adjust a face direction 411e of the metal member 411 by, for example, rotating the mount unit 413 in the direction of an arrow 422b so that the obtained luster intensity is maximized. According to such a direction modification unit 422, even if the through-hole ratio Rh of the metal member is high and the intensity of the reflected light 416b is low, the luster intensity can be increased by adjusting the face direction of the metal member 411, thereby enabling performing stable luster intensity measurement. Such adjustment of the face direction is not limited to rotational movement. Adjustment may be performed by moving the metal member in an X or Y direction in a plane parallel to the surface of the metal member.

By moving the irradiation unit 414 and luster intensity measurement unit 417 in directions 423a and 423b respectively, the angle modification unit 423 can modify the irradiation angle θr and reflection angle θr of the light beam 416a, and adjust the obtained luster intensity. Adjusting the irradiation angle θr and reflection angle θr enables, for example, increasing the amount of reflected light 416b from the metal member 411, and along with this, increasing the luster intensity.

The control unit 424 is electrically connected to function units such as the irradiation unit 414 by a wiring 427, can perform overall control of the function units, and can control at least one of the luster intensity measurement unit 417 and the light source 415 in accordance with, for example, the luster intensity. The control unit 424 performs adjustment so that the obtained luster intensity is an optimal intensity, thereby enabling, for example identifying a metal member simply, speedily, and highly precisely.

In this way, the metal identifying device 410 of the present Embodiment 4-1 includes the light detection unit 420 that can detect the through-hole ratio Rh, thereby enabling, for example, easily determining an optimal threshold value with the use of the through-hole ratio Rh and reference values. The metal identifying device 410 of the present Embodiment 4-1, simply, speedily, and with high precision, can identify the metal composition of a test object. Also, although the irradiation unit 414 and luster intensity measurement unit 417 are disposed separately in FIG. 22A, the irradiation unit 414 and luster intensity measurement unit 417 may be disposed in the same housing as shown in the enclosing broken line in FIG. 22A, as a luster measurer 426.

Figure 23:
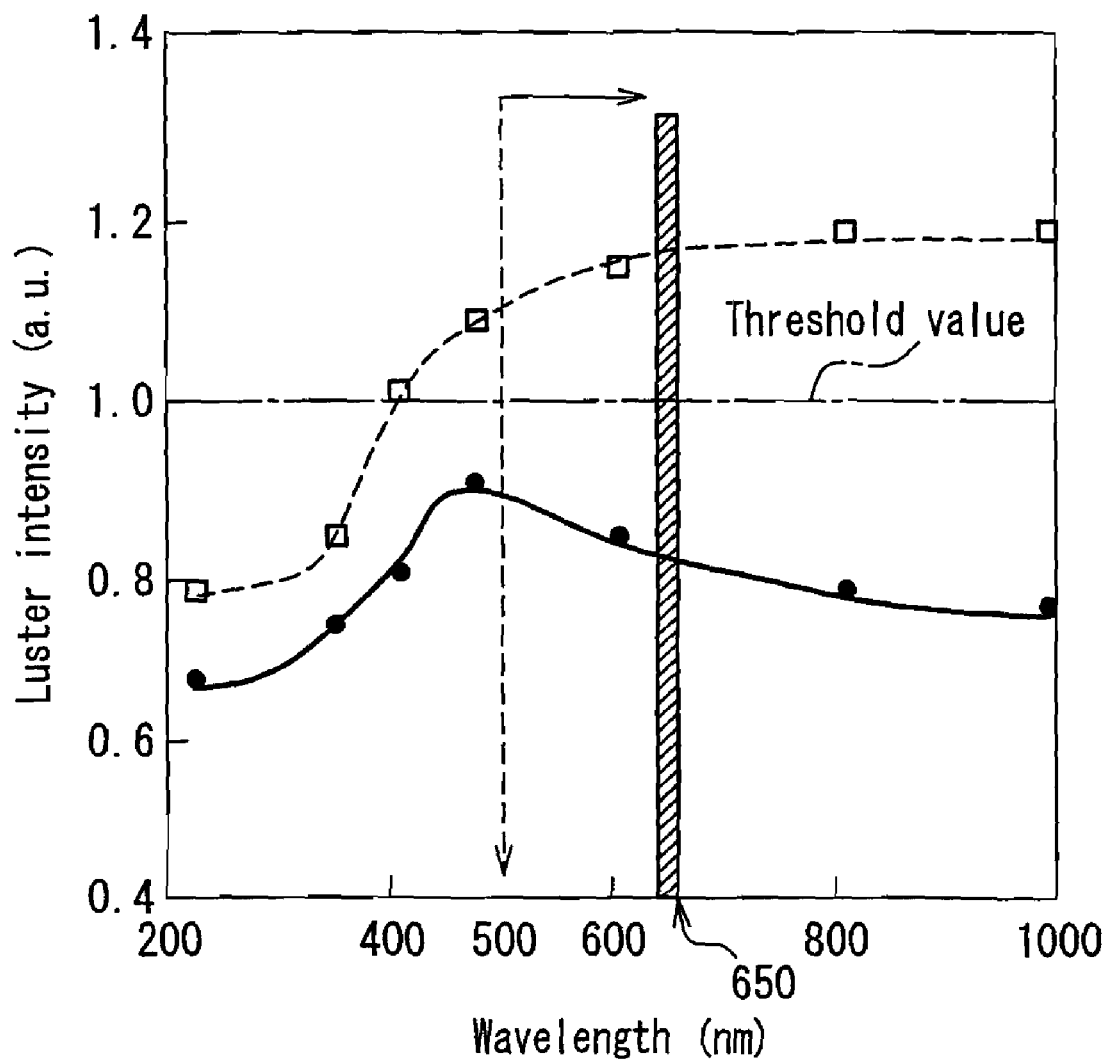
FIG. 23 is a graph showing exemplary optical spectrums of luster intensities obtained in Embodiment 4-1 of the present invention.

FIG. 23 shows luster intensity dispersion spectrums for a CRT shadow mask obtained using the metal identifying device 410 of the present Embodiment 4-1. The dispersion spectrums shown in FIG. 23 were obtained as a result of, for example, a dispersion generation unit (not shown), which is disposed between the luster intensity measurement unit 417 and the comparison circuit unit 418, performing decomposition for each wavelength component on luster intensities measured by the luster intensity measurement unit 417. In FIG. 23, the spectrum indicated by a solid line is an iron material dispersion spectrum, and the spectrum indicated by a broken line is an Invar alloy material dispersion spectrum. A white light source was used as the light source 415, and luster intensities in the wavelength range of 200 nm to 1,000 nm were measured. As shown in FIG. 23, a comparison of a short-wavelength range having wavelengths shorter than 550 nm and a long-wavelength range having wavelengths longer than 600 nm shows that the difference between iron material luster intensities and Invar alloy material luster intensities is greater in the long-wavelength range having wavelengths longer than 600 nm. For this reason, from the viewpoint of improving the identification precision, the metal composition of the test object is preferably identified by, for example, setting the threshold value luster intensity to 1.0 a.u., and performing a comparison using a luster intensity in the long-wavelength range having wavelengths longer than 600 nm. In this case, the metal composition can be identified as the Invar alloy material if the obtained luster intensity is greater than the threshold value, and can be identified as the iron material if the obtained luster intensity is less than the threshold value. From the viewpoint of identifying the metal composition more simply, the metal composition of a CRT shadow mask can be identified by using, for example, a 650 nm wavelength red LED or red laser as the light source 415 and performing a comparison using a luster intensity in the wavelength range in the vicinity of the wavelength of 650 nm. Note that in the case of comparing and identifying two types of metal compositions, an intermediate value between the two types may be used as the threshold value, or a value in the vicinity of the luster intensity of either of the metal compositions may be used as the threshold value.

Figure 24:
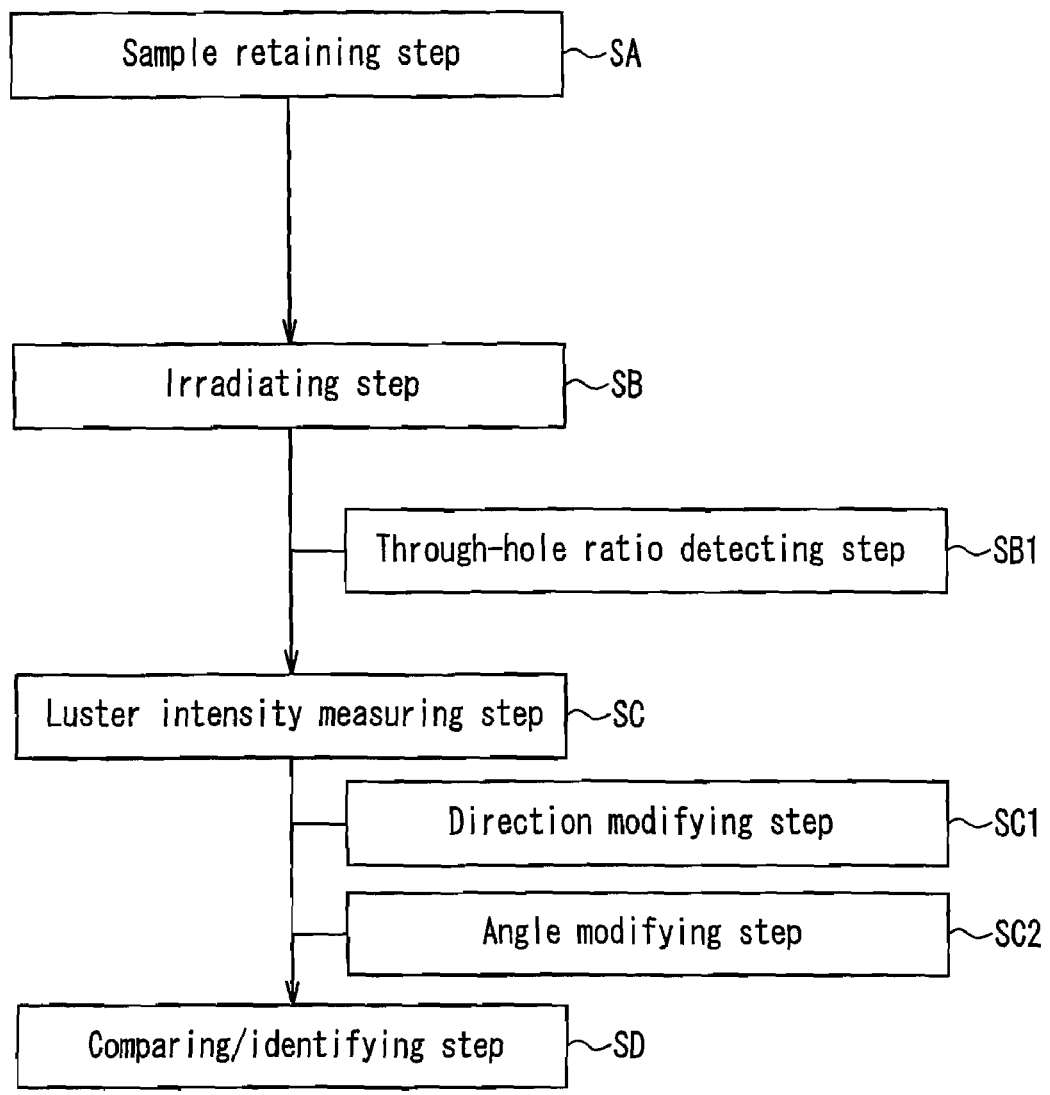
FIG. 24 is a flowchart showing an exemplary metal identifying method according to Embodiment 4-1 of the present invention.

The following describes a metal identifying method using the metal identifying device 410 of the present Embodiment 4-1 with reference to FIG. 22 and FIG. 24. FIG. 24 is a flowchart showing an exemplary metal identifying method using the metal identifying device 410 according to the present Embodiment 4-1. The identifying method of the present Embodiment 4-1 includes a sample retaining step (SA), an irradiating step (SB), a luster intensity measuring step (SC), and a comparing/identifying step (SD).

First, in the sample retaining step (SA), the metal member 411 is disposed on the mount unit 413. Next, in the irradiating step (SB), the irradiating unit 414, in which the light source 415 that irradiates the irradiation light 414a and the collimating lens 414c that converts the irradiation light 414a into the parallel light beam 414b are included, irradiates the light beam 416a on the metal member 411 at the predetermined angle θr. Then, in the luster intensity measuring step (SC), the luster intensity measurement unit 417 measures a luster intensity based on the reflected light 416b from the metal portion 411a of the metal member 411. Lastly, in the comparing/identifying step (SD), a threshold value is determined by selecting or correcting a reference luster intensity of the metal composition of the metal member 411 based on the ratio of the through-hole portions to the measurement area in the metal member and/or the configuration of the through-hole portion. The comparison circuit unit 418 compares the threshold value and the obtained luster intensity, and the comparison/identification unit 419 identifies the metal composition of the metal member (test object) 411. According to this method, identification is performed by comparing the above-described threshold value and the obtained luster intensity, thereby enabling identification of the metal composition of a test object simply, speedily, and precisely.

From the view point of improving the identification precision and enabling performing simple and speedy identification, the irradiating step (SB) may include, for example, a through-hole ratio detecting step (SB1). In this step, the light beam 416a and light detection unit 420 are used to detect the ratio Rh of through-hole portions 411b to the metal member 411. The through-hole ratio Rh can be used to, for example, determine the aforementioned threshold value and correct the obtained luster intensity, and is useful in improving the identification precision.

From the viewpoint of adjusting the intensity of the luster intensity measured by the luster intensity measurement unit 417 in order to enable improving the identification precision and performing simple and speedy identification, the luster intensity measuring step (SC) may include, for example, a direction modifying step (SC1) and an angle modifying step (SC2). The direction modifying step (SC1) is a step in which the face direction 411e of the metal member 411 is modified using the direction modification unit 422, thereby enabling adjusting the intensity of the luster intensity measured by the luster intensity measurement unit 417. Also, the angle modifying step (SC2) is a step in which the irradiation angle θr of the light beam 416a with respect to the metal member 411 is modified using the angle modification unit 423, thereby enabling adjusting the intensity of the luster intensity measured by the luster intensity measurement unit 417.

Embodiment 4-2

Figure 25:
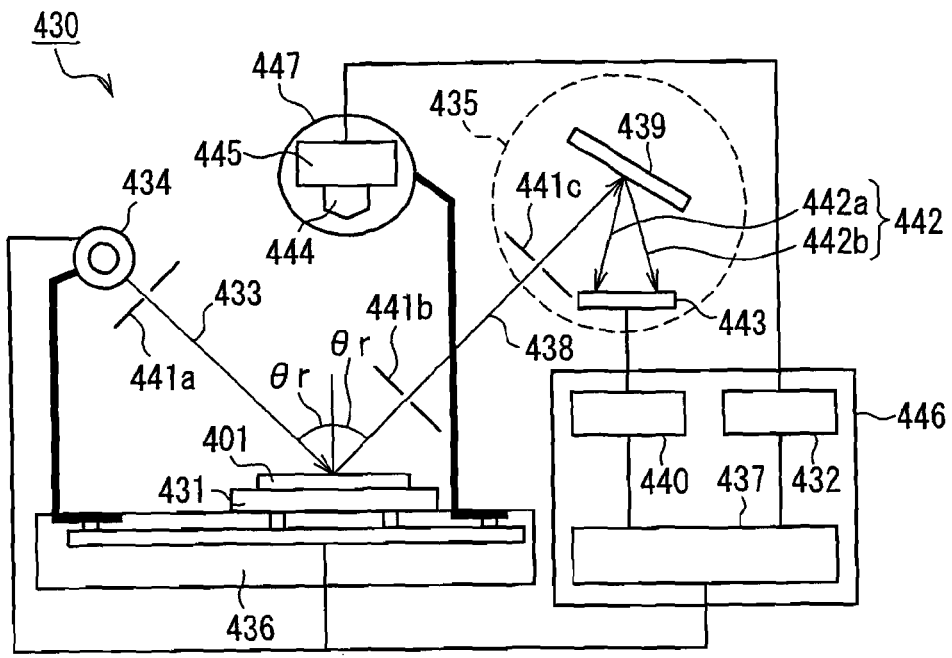
FIG. 25 is a schematic diagram showing an exemplary structure of a metal identifying device according to Embodiment 4-2 of the present invention.

FIG. 25 is a schematic diagram showing an exemplary structure of a metal identifying device according to Embodiment 4-2 of the present invention. The main constituent elements of a metal identifying device 430 shown in FIG. 25 are a mount unit 431, an irradiation unit 434, a position detection unit 447, a movement mechanism unit 436, a luster intensity measurement unit 435, and a controller 446. A metal member (test object) 401 that has a plurality of through-hole portions penetrating through the metal member can be placed on the mount unit 431. The mount unit 431 is disposed above the movement mechanism 436. For this reason, the mount unit 431 can be moved in a planar direction by controlling the movement mechanism unit 436. The luster intensity measurement unit 435 includes a dispersion generation unit 439, a linear image sensor 443 and an aperture 441c. The controller 446 includes a detected position storage unit 432, a movement mechanism control unit 437, and a spectrum comparison unit 440. The position detection unit 447 includes an image recognition device 445 and an imaging device 444, and is disposed above the mount unit 431. An aperture 441a is disposed between the irradiation unit 434 and the metal member 401, and an aperture 441b is disposed between the metal member 401 and the luster intensity measurement unit 435.

The irradiation unit 434 can irradiate a light beam 433 on the metal member 401. Part of the irradiated light from the light source (not shown) of the irradiation unit 434 is converted into parallel light in the irradiation unit 434, and the resulting light beam 433 passes through the aperture 441a. Luster 438 is generated by the light beam 433 being irradiated in, for example, an elliptical configuration on the surface of the metal member 401. The luster 438 passes through the aperture 441b and the aperture 441c in the lustrous intensity measurement unit 435, and arrives at the dispersion generation unit 439. Due to the luster 438 passing through the apertures 441b and 441c, portions of the light beam that scattered on the surface of the metal member 401 are eliminated. The diameter of the aperture 441a is preferably larger than the beam diameter of the light beam 433. Also, the apertures 441b and 441c preferably can transmit light having a beam diameter that is the same size as the aperture 441a. The light source of the irradiation unit 434 can be a light source that can irradiate a white light beam, such as a xenon discharge light, due to having a property of emitting light that has relatively little wavelength dependency in the visible light range, and emitting high-intensity light. In a case of irradiating the light beam 433 to generate the luster 438, the angle θr is generally set to 60 degrees or 20 degrees.

The dispersion generation unit 439 of the luster intensity measurement unit 435 generates a dispersion spectrum 442 based on the luster 438 that incidented thereon. The luster is dispersed into wavelengths, received by the linear image sensor 443 in this condition, and then stored in the spectrum comparison unit 440.

The imaging device 444 of the position detection unit 447 captures an image of the metal member 401, and the image recognition device 445 processes the image in order to, for example, detect positional coordinates of the through-hole portions in the metal member 401. The positional coordinates can be stored in the detected position storage unit 432 as two-dimensional position information. Based on the position information stored in the detected position storage unit 432, the movement mechanism control unit 437 controls either the irradiation unit 434 or mount unit 431 so that the light beam 433 is irradiated selectively on a portion of the metal member 401 other than the through-hole portions. Also, Instead of having a structure including the imaging device 444 and image recognition device 445, the position detection unit 447 may be an optical unit including a simple light emitting element and a light receiving element. In the case of having such a structure, the positions of the through-hole portions and metal portion of the metal member can be recognized by, for example, irradiating light from the light emitting element in a direction perpendicular to the metal member, and detecting changes in the quantity of reflected light with use of the light receiving element.

The mount unit 431 and movement mechanism unit 436, for example, may have the structures shown in FIGS. 10A and 10B, similarly to Embodiment 2-1. Such structures enable easily moving the mount unit 202 to the left and right with use of the linear motor 213. For this reason, the through-hole portions in the test object can be avoided easily when irradiating the light beam by, for example, moving the position of the irradiation unit or mount unit based on the through-hole portion position information detected by the detected position storage unit. According to this structure, the test object easily can be placed on and removed from the mount unit by, for example, blocking the coil current. Adjusting the strength of the electromagnet enables flattening out deformations in the test object, thereby improving the analysis precision. Furthermore, in the case of identifying the metal composition of a test object whose surface lacks projections, the metal member can be disposed in a condition of being in close contact with the bottom of the housing, thereby enabling, for example, measuring the luster intensity of the test object in a condition in which stray light has been reduced.

Similarly to Embodiment 3-1, the metal identifying device 430 of the present Embodiment 4-2 can, for example, identify the metal composition of CRT shadow masks having the structures shown in FIGS. 15B and 15C. The following describes a metal identifying method using the metal identifying device 430 of the present Embodiment 4-2, taking the example of identifying a CRT shadow mask having the structure shown in FIG. 15C.

First, the metal member 401 is placed on the mount unit 431. Then, the positions of the through-hole portions and metal portion of the metal member 401 are detected with use of the imaging device 444 and image recognition device 445, and stored in the detected position storage unit 432 in the controller 446.

Based on the position information, the movement mechanism control unit 437 in the controller 446 adjusts, with use of the movement mechanism 436, the positional relationship between the irradiation unit 434 and metal member 401. The light beam 433, which is a parallel beam having a diameter narrowed down to approximately 1 mm, is irradiated from the irradiation unit 434, passes through the aperture 441a, and is irradiated on the metal member 401. The diameter of the aperture 441a is, for example, approximately 1 mm. The luster 438 from the metal member 401 passes through the aperture 441b and aperture 441c, which transmit a light beam having a beam diameter that is the same size as the aperture 441a, and is measured by the luster intensity measurement unit 435. A reflective diffraction grating or the like may be disposed as the dispersion generation unit 439 in the luster intensity measurement unit 435. Examples of the reflective diffraction grating include a reflective diffraction grating that disperses the luster 438 by changing the angle thereof for each wavelength component in a range in the vicinity of visible light (a range of 200 nm to 1,000 nm inclusive). In this case, the luster 438 that has reflected off the dispersion generation unit 439 is received as a dispersion spectrum in which the wavelength components are dispersed from one edge of the linear image sensor 443 to the other edge. For example, in the dispersed luster 438, a dispersion spectrum 442a of ultraviolet light in the vicinity of a wavelength of 200 nm arrives at a right edge of the linear image sensor 443, and a dispersion spectrum 442b of infrared light in the vicinity of a wavelength of 1,000 nm arrives at a left edge of the linear image sensor 443. Also, a dispersion spectrum including visible light in the range of 200 nm to 1,000 nm inclusive and light in the vicinity thereof arrives at a center portion of the linear image sensor 443 that is sandwiched between the areas where the dispersion spectrum 442a and dispersion spectrum 442b are received.

Figure 26:
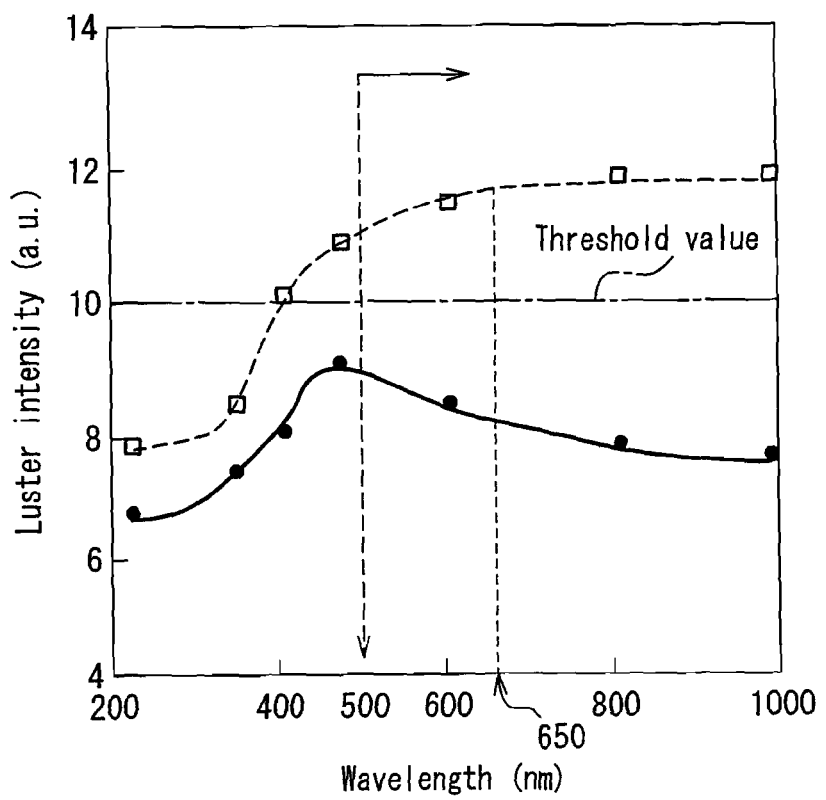
FIG. 26 is a graph showing exemplary dispersion spectrums of luster intensities obtained in Embodiment 4-2 of the present invention.

FIG. 26 shows luster intensity dispersion spectrums of a CRT shadow mask obtained using the metal identifying device 430 of the present Embodiment 4-2. In FIG. 26, the spectrum indicated by a solid line is an iron material dispersion spectrum, and the spectrum indicated by a broken line is an Invar alloy material dispersion spectrum. As shown in FIG. 26, there is a large difference between the iron material and the Invar alloy material with respect to the luster intensity dispersion spectrums indicated as wavelength dependency. The luster intensity of the iron material CRT shadow mask has a peak in the vicinity of a wavelength of 500 nm, but does not vary much in the wavelength range of 200 nm to 1,000 nm. On the other hand, the luster intensity of the Invar alloy material CRT shadow mask does not vary much in the wavelength range of 200 nm to 400 nm, rises greatly in the range of 400 nm to 500 nm, and is substantially constant upon exceeding 500 nm. In the wavelength range of 500 nm to 1,000 nm inclusive, the luster intensity of the Invar alloy material is clearly greater than the luster intensity of the iron material. Accordingly, determining the threshold value to be, for example, a luster intensity of 10 a.u. enables identifying whether a metal member is constituted from the iron material of the Invar alloy material.

By determining the threshold value in this way, and by the spectrum comparison unit 440 performing a comparison to judge whether the obtained luster intensity exceeds the threshold value, a metal composition can be identified with high precision, simply, and speedily.

Also, the luster dispersion spectrum of metal compositions to be identified may be stored in advance as reference dispersion spectrums, and the reference dispersion spectrums may be measured before measuring the test object. The metal composition of the test object can be identified by setting a reference dispersion spectrum as the threshold value and comparing the threshold value and the dispersion spectrum obtained from the test object. Here, a plurality of reference dispersion spectrums may be prepared according to the ratio of the through-hole portions to the measurement area in the metal member and/or the configuration of the through-hole portion, and the reference dispersion spectrum that is used may be selected from among the prepared reference dispersion spectrums based on the ratio of the through-hole portions and/or the configuration of the through-hole portion. Also, the reference dispersion spectrum may be obtained by performing correction on metal-specific dispersion spectrums based on the ratio of the through-hole portions and/or the configuration of the through-hole portion.

Figure 27:
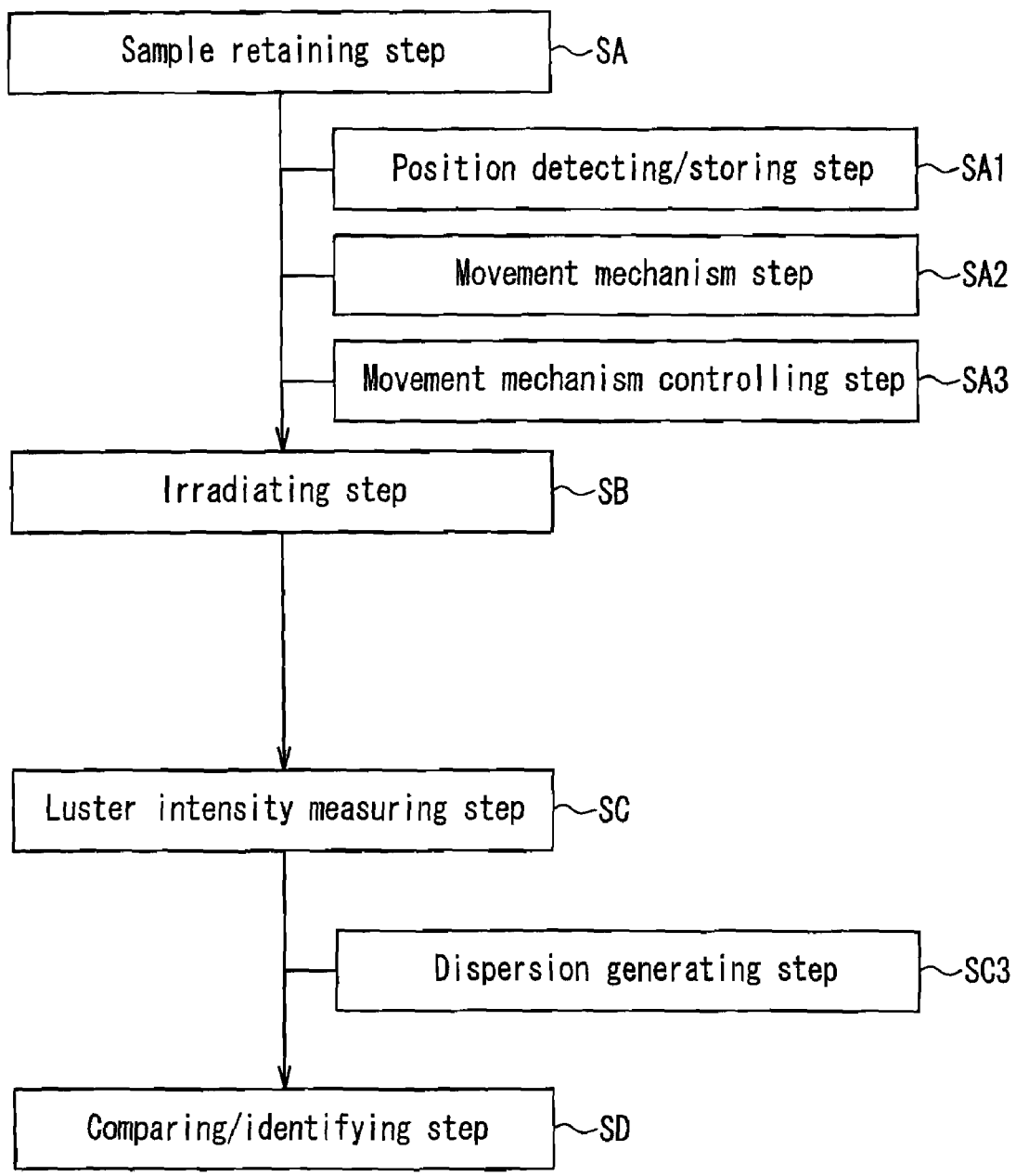
FIG. 27 is a flowchart showing an exemplary metal identifying method according to Embodiment 4-2 of the present invention.

The following describes a metal identifying method using the metal identifying device 430 of the present Embodiment 4-2 with reference to FIG. 25 and FIG. 27. FIG. 27 is a flowchart showing an exemplary metal identifying method using the metal identifying device 430 according to the present Embodiment 4-2. The identifying method of the present Embodiment 4-2 includes the sample retaining step (SA), the irradiating step (SB), the luster intensity measuring step (SC), and the comparing/identifying step (SD), and these steps can be performed similarly to as in Embodiment 4-1.

The sample retaining step (SA) further may include a position detecting/storing step (SA1), a movement mechanism controlling step (SA2) and a movement mechanism controlling step (SA3). In the position detecting/storing step (SA1), the positions of the through-hole portions in the metal member 401 are detected, and the obtained position information is stored in the detected position storage unit 432. In the movement mechanism step (SA2), the movement mechanism unit 436 moves at least one of the luster intensity measurement unit 435, and the irradiation unit 434 and mount unit 431. In the movement mechanism controlling step (SA3), the movement mechanism control unit 437 controls the position of the irradiation unit 434 and/or the mount unit 431 based on the position information stored in the detected position storage unit 432, so that the light beam 433 is selectively irradiated on the metal portion of the metal member 401. By including these steps, in the exemplary case where the luminous flux area of the light beam 433 is smaller than the area of a through-hole portion, moving the irradiation unit 434 or the like based on the position information enables selectively irradiating the light beam 433 so that the center of the irradiated light spot is irradiated on the metal portion of the metal member 401. Comparing the thus obtained luster 438 and the threshold value enables identifying the metal highly precisely, simply, and speedily.

The luster intensity measuring step (SC) further may include a dispersion generating step (SC3). In the dispersion generating step (SC3), the dispersion generation unit 439 generates a dispersion spectrum by performing spectrum decomposition on the luster intensity. Due to generating the dispersion spectrum, in the comparing/identifying step (SD), the comparison circuit unit 418 or spectrum comparison unit 440 can perform a comparison with use of the intensity of the dispersion spectrum. This enables highly precise, simple, and speedy identification of the metal.

Embodiment 4-3

Figure 28A:
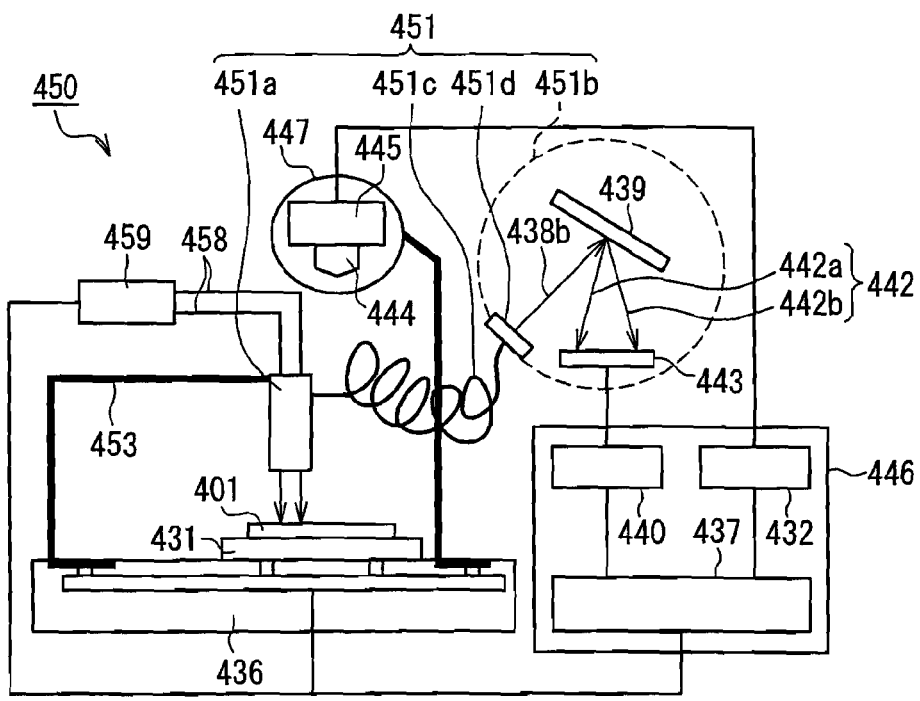
FIG. 28A is a schematic diagram showing an exemplary structure of a metal identifying device according to Embodiment 4-3 of the present invention.
Figure 28B:
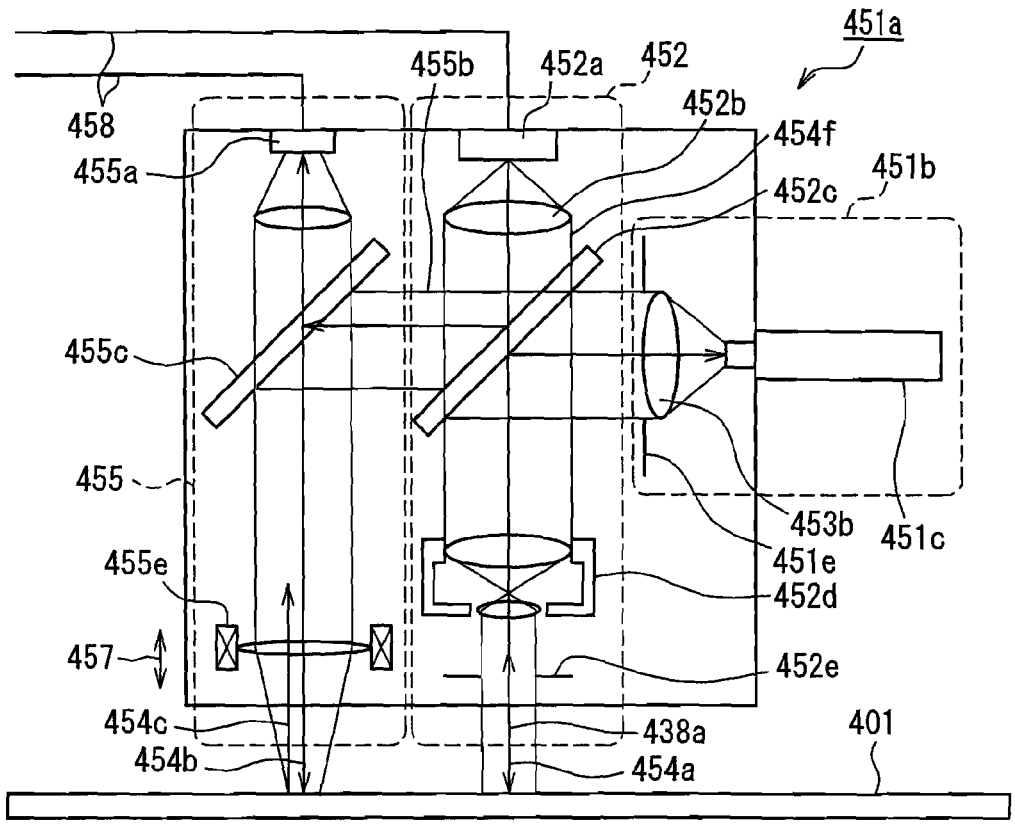
FIG. 28B is a schematic diagram showing an exemplary structure of a light reception/emission unit in the metal identifying device according to Embodiment 4-3 of the present invention.

FIG. 28A is a schematic diagram showing an exemplary structure of a metal identifying device according to Embodiment 4-3 of the present embodiment, and FIG. 28B is a schematic diagram showing an exemplary structure of a light reception/emission unit in the metal identifying unit. A metal identifying device 450 of FIG. 28A has the same structure as the metal identifying device 430 of Embodiment 4-2, with the exception that the irradiation unit and light reception unit have been integrated into a light reception/emission unit 451.

As shown in FIG. 28A, the light reception/emission unit 451 includes a light emission unit 451a, a luster intensity measurement unit 451b, an optical fiber 451c, and a luster incidence unit 451d. As shown in FIG. 28B, the light emission unit 451a includes an irradiation unit 452 and a light detection unit 455. The irradiation unit 452 includes a light source 452a, a lens 452b, a half mirror 452c, a beam converting lens 452d, and an aperture 452e. The light detection unit 455 includes a light reception unit 455a, a half mirror 455c, and a movable optical member 455e. A lens actuator or the like can be used as the movable optical member 455e.

As shown in FIG. 28B, in the irradiation unit 452, a light beam 454a is irradiated from the light source 452a, and the light beam 454a is converted into a parallel light beam 454f by passing through the beam converting lens 452b. Part of the parallel light beam 454f is reflected toward the light detection unit 455 by the half mirror 452c. The parallel light beam 454f that has passed through the half mirror 452c is narrowed to a beam diameter of 1 mm or less by the beam converting lens 452d, passes through the aperture 452c, and is irradiated on the metal member 401 as the light beam 454a that is parallel light.

As shown in FIG. 28B, in the light detection unit 455, a light beam 455b, which is part of the parallel light beam 454f that was reflected by the half mirror 452c, is reflected by the half mirror 455c and becomes detection light 454b. With use of the movable optical member 455e, the detection light 454b is irradiated on the metal member 401 so that the focus of the detection light 454b is positioned on the surface of the metal member 401. The detection light 454b is reflected off the metal member, and the resulting reflected detection light 454c is received by the light reception unit 455a, thereby detecting the presence/absence of a through-hole portion in the metal member 401. Luster 438a from the metal member 401 passes through the beam converting lens 452d, and thereafter is reflected toward the luster intensity measurement unit 451b by the half mirror 452c, passes through an aperture 451e and lens 453b, and incidents on the optical fiber 451c. The luster 438b passes through the luster incidence unit 451d in the luster intensity measurement unit 451 and is incident on the dispersion generation unit 439 as a parallel light beam.

According to the metal identifying device 450 of the present Embodiment 4-3, a light beam is irradiated on a metal material having through-hole portions, a dispersion spectrum for luster from the metal member is obtained, and a comparison is performed with the threshold value of a dispersion spectrum set in advance, thereby enabling simply, precisely, and speedily identifying the metal material. Even if the metal member has fine roughness or a foreign object is attached thereto, the metal member can be identified even more simply, precisely and speedily by, for example, self-selecting a flat portion of the metal material. In the present Embodiment 4-3, if the luminous flux area of the detection light 454b is larger than the area of a through-hole portion in the metal member, the through-hole ratio Rh of the metal member may be detected similarly to Embodiment 4-1.

Figure 29A:
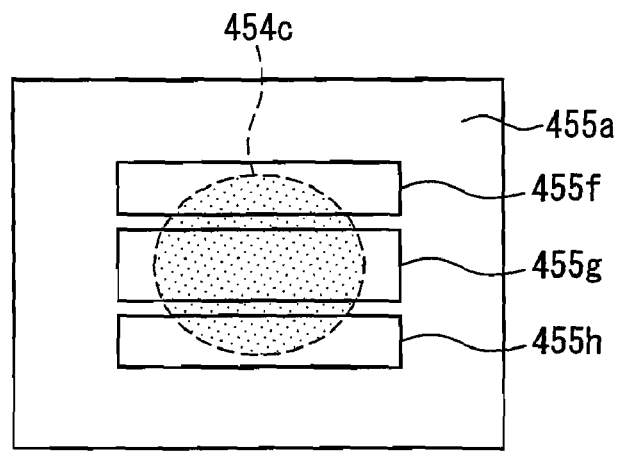
FIGS. 29A to 29C are schematic diagrams showing exemplary sizes of reflected detection light $454c$ detected in a light reception unit $455a$ shown in FIG. 28A.
Figure 29B:
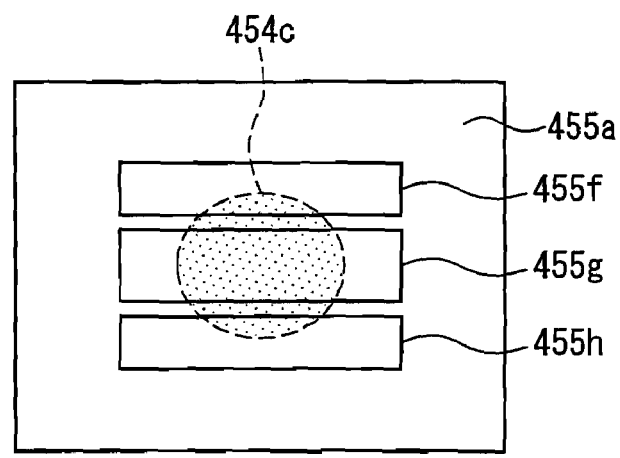
Figure 29C:
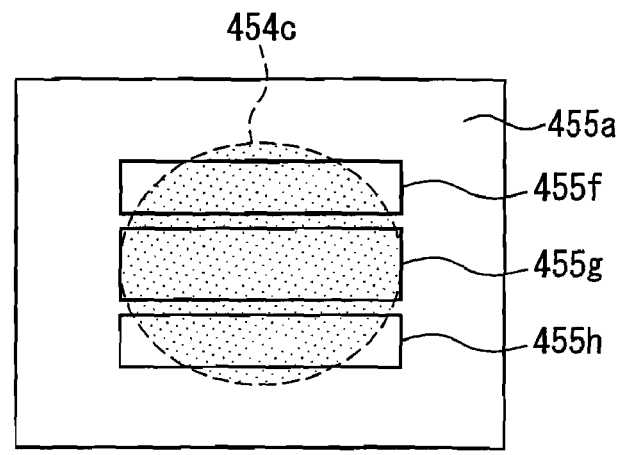

FIGS. 29A to 29C are schematic diagrams showing exemplary sizes of the reflected detection light 454c that are incident on the light reception unit 455a. FIG. 29A is a schematic diagram showing the size of the incidenting reflected detection light 454c in a case of the detection light 454b being focused on the surface of the metal member 401. FIGS. 29B and 29C are schematic diagram showing the size of the incidenting detection light 454c in a case of the focal position being shifted with respect to the surface of the metal member 401. FIG. 29B shows a case of being too far from the light detection unit 455, and FIG. 29C shows a case of being too close to the light detection unit 455.

As shown in FIGS. 29A to 29C, the light reception unit 455a is divided into three parts, namely light receiving elements 455f, 455g and 455h. If the detection light 454b is focused on the surface of the metal member 401, a difference between the signal output pertaining to the reflected detection light 454c detected by the light receiving element 455g and a sum of the signal output pertaining to the reflected detection light 454c detected by the light receiving element 455f and the signal output pertaining to the reflected detection light 454c detected by the light receiving element 455g is a substantially constant value. This value, which is a movement distance 457 of the movable optical member 455e, is stored in, for example, a drive unit 459 that is connected electrically to the light emission unit 451a by a wiring 458. As shown in FIGS. 29B and 29C, if the focal position is shifted with respect to the surface of the metal member 401, the difference between signal output obtained as described above becomes greater than or less than the constant value. The positional relationship between the light detection unit 455 and metal member 401, the movement distance 457 of the movable optical member 455e, and the like can be detected based on variation in the difference between signal output. As a result, the detection light 454b easily can be focused on the surface of the metal member 401. If a through-hole portion exists at the irradiation position of the detection light 454b, or the surface of the metal member at the irradiation position is not flat, the quantity of light in the reflected detection light 454c falls by a large amount, and therefore the signal output becomes extremely small. For this reason, the presence of through-hole portions, roughness and foreign objects on the surface of the metal member 401, and the like can be detected based on variations in the signal output. In the case of the surface of the mount unit 431, the depth of a through-hole portion can be detected based on variations in the signal output. In this way, the determination of the movement distance 57 of the movable optical member 455e, the detection of roughness on the surface of the metal member 401, the detection of the presence of a through-hole portion, and the like easily can be performed based on the size of the reflected detection light 454c on the light reception unit 455a.

Figure 30A:
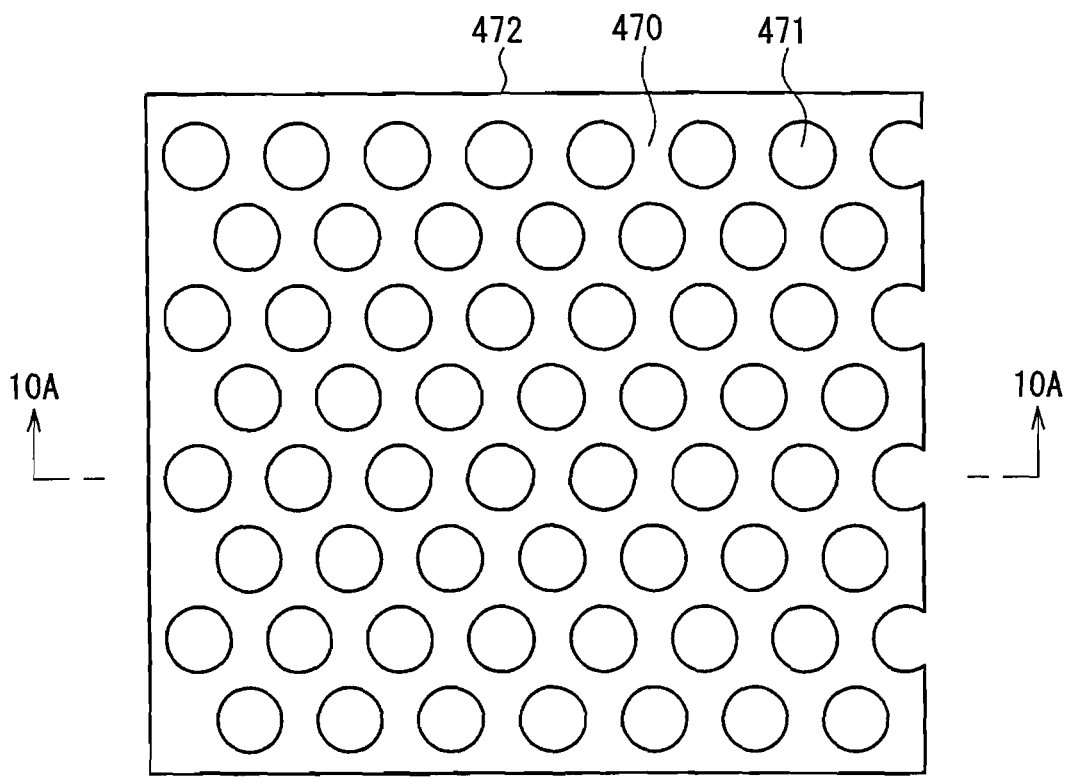
FIG. 30A is a plan view showing an exemplary metal member having through-hole portions.
Figure 30B:
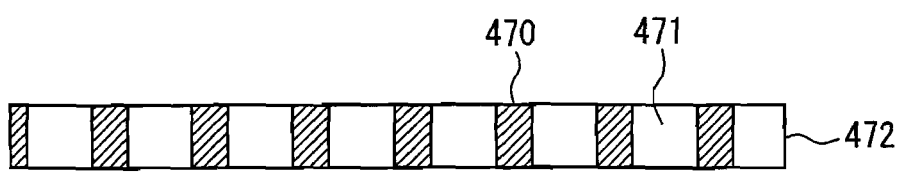
FIG. 30B is a cross-sectional view taken along a line 10A-10A in FIG. 30A.
Figure 30C:
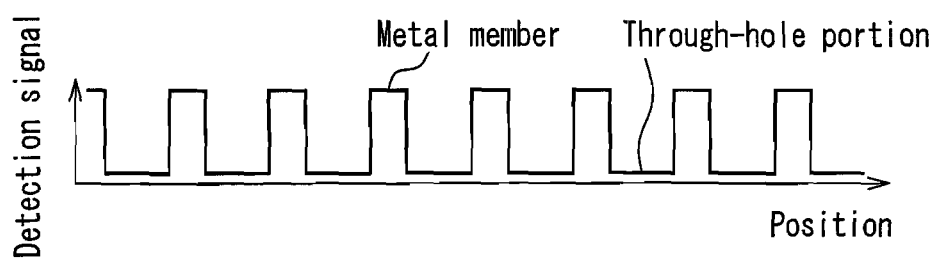
FIG. 30C is a diagrammatic view showing an exemplary detection signal at metal portions and through-hole portions of a metal member, which has been measured along the line 10A-10A.

The following describes a method of detecting a through-hole portion based on signal output using the metal identifying device 450 of the present Embodiment 4-3, with reference to FIG. 28 and FIGS. 30A to 30C. FIG. 30A is a plan view of a metal member having through-hole portions. FIG. 30B is a cross-sectional view taken along a line 10A-10A in FIG. 30A. FIG. 30C is a diagrammatic view showing an exemplary detection signal at metal portions and through-hole portions of the metal member, which has been measured along the line 10A-10A. As shown in FIG. 30C, the surface of the mount unit 431 has more roughness than the surface of the metal member 401. For this reason, the signal output at places corresponding to the through-hole portions is very low, and the signal output at places corresponding to the metal portion is high.

Based on the above, first a rough position of the through-hole portions in the metal member is detected with use of the imaging device 444 and image recognition device 445, and then a detailed condition of the surface of the metal member is detected with use of the light emission unit 451a of the light reception/emission unit 451. This enables measuring the luster 438a from the metal member with very high precision, thereby improving the metal identification precision.

Embodiment 4-4

Figure 31:
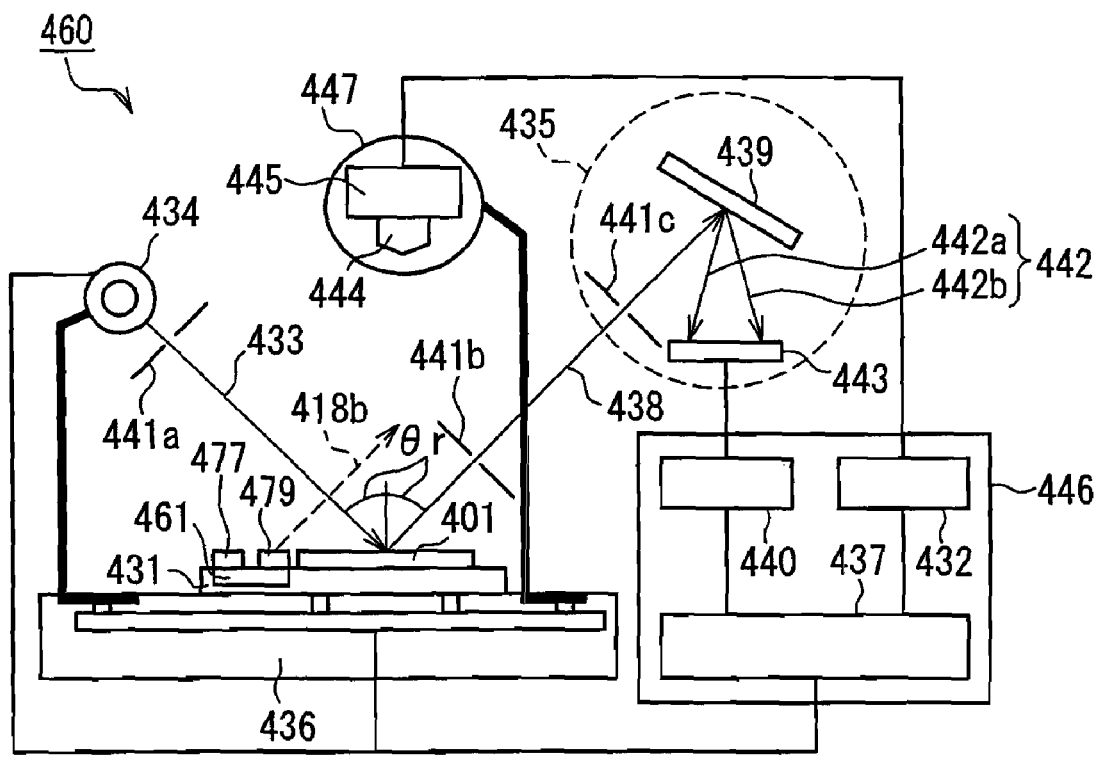
FIG. 31 is a schematic diagram showing an exemplary structure of a metal identifying device according to Embodiment 4-4 of the present invention.

FIG. 31 is a schematic diagram showing an exemplary structure of a metal identifying device according to Embodiment 4-3 of the present invention. A metal identifying device 460 of FIG. 31 has the same structure as the metal identifying device 430 of Embodiment 4-2, with the exception that the mount unit 431 includes a monitor metal member placing unit 461, and monitor metal members 477 and 479 can be disposed in addition to the metal member 401. The monitor metal members 477 and 479 can be the same as in Embodiment 4-2.

In the metal identifying device 460 of the present Embodiment 4-4, first the mount unit 431 is moved using the movement mechanism unit 436, and the irradiation unit 434 irradiates the light beam 433 on the monitor metal members 477 and 479. The luster intensity measurement unit 435 receives the luster 438, and the dispersion generation unit 439 generates a dispersion spectrum for each of the monitor metal members 477 and 479. Next, the mount unit 431 is moved using the movement mechanism unit 436, the irradiation unit 434 irradiates the light beam 433 on the metal member 401, and the dispersion generation unit 439 generates a dispersion spectrum based on the luster 438. The spectrum comparison unit 440 compares the dispersion spectrum based on the luster 438 from the metal member 401 and a reference dispersion spectrum. In this way, the metal composition of the metal member (test object) 401 is identified.

According to the metal identifying device 460 of the present Embodiment 4-4, since the monitor metal members 477 and 479 can be disposed, for example, beside the metal member 401, both the metal member 401 that is the test object and the monitor metal members 477 and 479 are irradiated by the light beam, thereby enabling measurement of the dispersion spectrum of the monitor metal members under the same conditions as the metal member 401 that is the test object. Comparing and analyzing the dispersion spectrums of the obtained luster enables improving the metal identification precision. Also, there is no need to, for example, measure metal-specific dispersion spectrums etc. in advance since the reference dispersion spectrums for comparison can be measured at the same time that the test object dispersion spectrum is measured. This enables simple and speedy identification of the metal composition of the test object.

Figure 32:
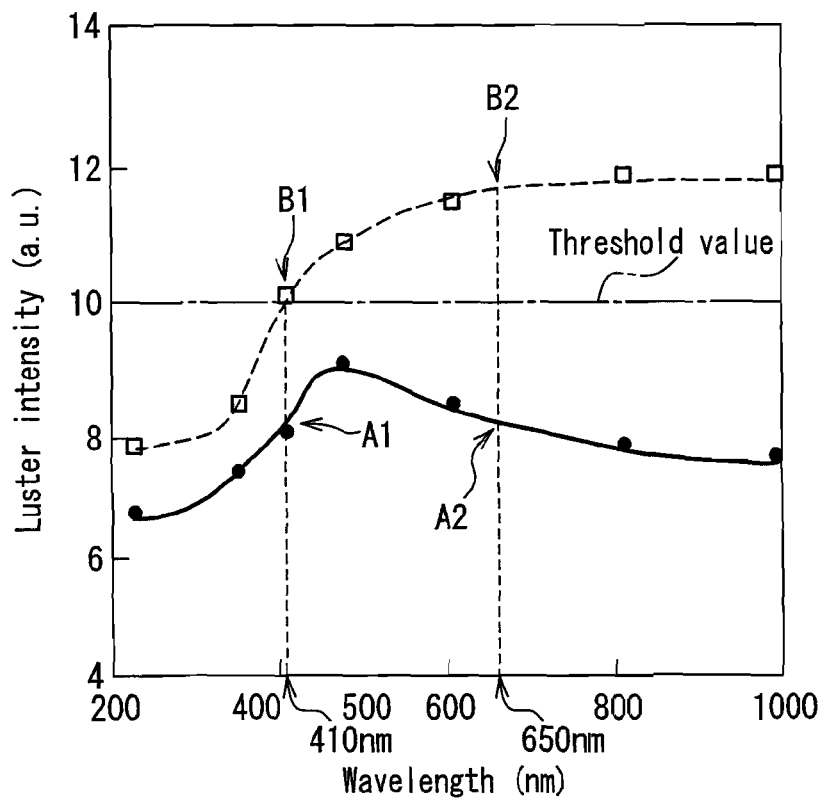
FIG. 32 is a graph showing exemplary dispersion spectrums of luster intensities obtained in Embodiment 4-4 of the present invention.

FIG. 32 shows luster intensity dispersion spectrums of a monitor metal members obtained using the metal identifying device 460 of the present Embodiment 4-4. In FIG. 32, the spectrum indicated by a solid line is an iron material dispersion spectrum, and the spectrum indicated by a broken line is an Invar alloy material dispersion spectrum. As shown in FIG. 32, the wavelength range to be compared can be set to, for example, 400 nm to 800 nm, and a threshold value Th can be set to, for example, 9.5. The luster intensity of the metal member is measured, and if the obtained luster intensity exceeds the threshold value Th in the wavelength range of 400 nm to 800 nm, the metal composition of the test object can be identified as the Invar alloy material. On the other hand, if the obtained luster intensity is less than or equal to the threshold value Th, the metal composition of the test object can be identified as the iron material. Also, the identification may be performed based on the luster intensity in a specified wavelength (e.g., 410 nm or 650 nm), or based on a luster intensity difference between specified wavelengths. In the former case, the metal can be identified by setting the threshold value at a specified wavelength (e.g., 410 nm or 650 nm), and comparing the threshold value at that wavelength and the obtained luster intensity. In the latter case, the metal can be identified by calculating a difference between luster intensities at, for example, 410 nm and 650 nm, and comparing the difference and the threshold value. Specifically, in the graph of FIG. 32, in the case of the Invar alloy material, the difference between luster intensities (B2−B1) is approximately 1.5, and in the case of the iron material, the difference between luster intensities (A2−A1) is approximately 0.2. Accordingly, the threshold value Th is set to, for example, 1, the threshold value and the difference between obtained luster intensities is compared, and the metal can be identified according to the magnitude relationship therebetween.

In this way, the spectrum comparison unit 440 compares, for example, luster intensities only in specified wavelengths or a specified wavelength range in a wavelength range of infrared light to ultraviolet light, thereby enabling more simple, speedy, and highly precise identification of the metal composition of the test object.

Figure 33:
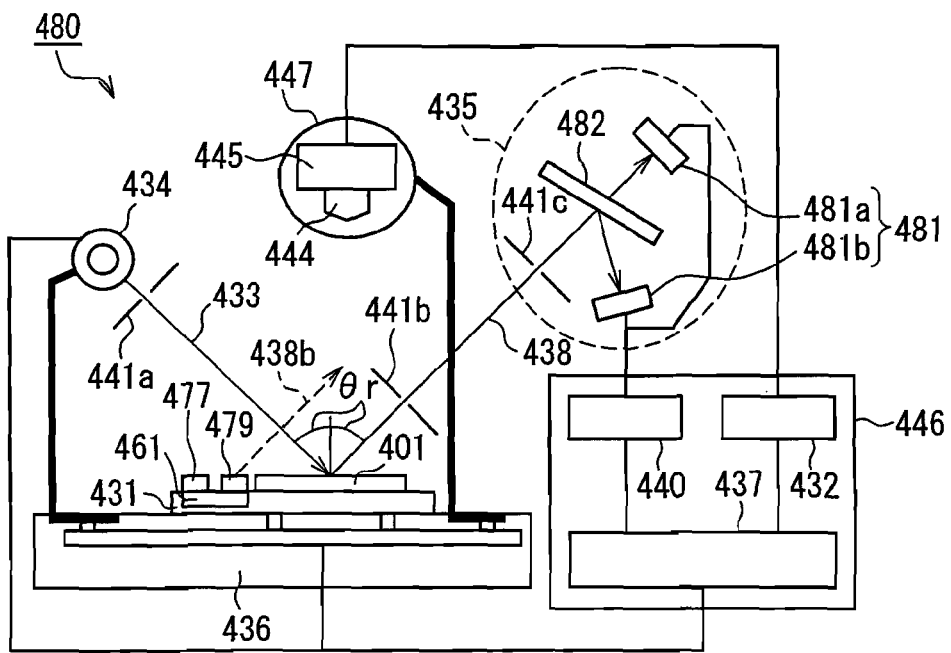
FIG. 33 is a schematic diagram showing another structure of the metal identifying device according to Embodiment 4-4 of the present invention.

FIG. 33 is a schematic diagram showing another example of a metal identifying device according to Embodiment 4.4 of the present invention. A metal identifying device 480 of FIG. 33 has the same structure as the metal identifying device 460, with the exception that the luster intensity measurement unit 435 is constituted from light receiving elements 481a and 481b and a dichroic mirror 482.

The luster intensity measurement unit 435 of the metal identifying device 480 includes light receiving elements 481

(481a and 481b) and the dichroic mirror 482. In this way, including two types of light receiving elements, namely the light receiving elements 481a and 481b enables simply and speedily measuring a dispersion spectrum in a specified wavelength range, instead of measuring, for example, luster dispersion spectrums in the entire visible light range. This is particularly beneficial if, for example, there is a clear difference between reflection rates in a specified wavelength range, such as with the iron material and the Invar alloy material. In the case of identifying the iron material and the Invar alloy material, luster only in a band in the vicinity of a wavelength of 650 nm is received by the light receiving element 481a, and reflected light in the other long-wavelength range is received by the light receiving element 481b. Comparing a reference dispersion spectrum and the dispersion spectrum of each range enables identifying whether the metal material is the iron material or the Invar alloy material. For example, a dichroic mirror whose surface is coated with a dielectric multi-layer film that transmits only light in a band in the vicinity of the wavelength of 650 nm and reflects light in other ranges can be used as the dichroic mirror 482. The metal identifying device 480 of the present Embodiment 4-4 enables more highly precise, simple, and speedy identification of the metal.

Also, similarly to Embodiment 3-4, the light source and irradiation unit of Embodiments 4-1 to 4-4 may include at least one each of a red light source, a green light source and a blue light source. Also, these light sources may be used independently or simultaneously, as necessary. The light sources may be the same as in Embodiment 3-4.

Also, as described above, since the luster intensity dispersion spectrums differ depending on the configuration of the through-hole portion and/or the ratio of the through-hole portions, the provision of a plurality of threshold values for each metal composition enables further improving the identification precision. Furthermore, as described in Embodiment 4-1, from the viewpoint of improving the identification precision, the threshold values and luster intensity measurement values may be corrected based on correction data or the through-hole ratio Rh of the metal member in the other embodiments as well. The method of correcting the measurement values in this way is particularly beneficial in the case of, for example, the through-hole ratio Rh of the metal member being high, that is to say, the ratio of the through-hole portions to the measurement area in the metal members being low, since the numerical value of the measurement value is amplified and the degree of freedom in setting the threshold value is increased.

The above embodiments describe cases in which a single measurement means is applied when identifying the metal composition of a test object. In the recycling process, test objects are generally disassembled by pressing, separation, and the like, and therefore there are very often cases in which the condition of the test object at the time of identification is very degraded, such as having fractures in the metal portions forming the through-hole portions, a lack of flatness, and surface contamination due to the attachment of dust etc. in the disassembly processing. Also, the strength of tension masks is weak since, as shown in FIG. 1B, the Y axis direction width of the metal portion that extends in the X axis direction is very narrow. For this reason, there are cases in which unique problems (measurement errors etc.) occur in a case of identifying a plate-shaped metal member having a plurality of through-hole portions penetrating through the metal member, such as a shadow mask. In the exemplary case of measuring electrical resistance, there are cases in which deflection occurs in the metal member when the four-terminal measurement probe is brought into contact with the metal member. There are thought to be cases in which the measurement probe cannot be in sufficient contact with the metal member due to such deflection. Also, in a case of measuring an emission spectrum by a discharge, there are thought to be cases in which the emission intensity is weak and a peak value and/or peak shape sufficient to enable identification cannot be obtained since, for example, the absolute quantity of the metal member that is to cause a discharge is too little.

In such a case, the identification precision can be improved further by measuring a plurality of different properties of the metal member. In other words, in the above embodiments, there are electrical resistance values, emission spectrums, reflection spectrums, and luster intensities. Also, the above roughly can be classified by, for example, the presence or absence of contact with the metal member, or the presence or absence of breakdown in the metal member. In other words, a measurement means in which electrical resistance values are applied involves contact-type measurement in which the four-terminal measurement probe is brought into contact with the metal member to perform measurement, whereas a measurement means in which reference spectrums, luster intensities and emission spectrums are applied involves contactless measurement in which measurement is performed by detecting a light beam from the metal member. Also, a means in which emission spectrums are applied involves breakdown-type measurement in which the metal member constituting the periphery of the through-hole portions melts due to a discharge, whereas a measuring means in which electrical resistance values, reflection spectrums and emission intensities are applied involves non-breakdown measurement in which breakdown etc. in the metal member such as above does not occur. In other words, examples include a combination of contact-type measurement and contactless measurement (e.g., a combination of electrical resistance value measurement and emission intensity measurement), and a combination of non-breakdown measurement and breakdown-type measurement (a combination of emission intensity measurement and either reflection intensity measurement or luster intensity measurement). Since the properties differ in this way, using a combination of different properties enables further improving the identification precision and ensuring highly reliable identification performance. Note that specific measurement values of these combined embodiments are not different from the values described in detail in the above embodiments, and a description of a specific measurement method has been omitted since methods can be realized based on the above embodiments.

The above embodiments describe cases in which a CRT shadow mask is taken as an example, and the metal identifying device and metal identifying method of the present invention are applied to a disassembly-sorting line for CRT display metal parts. However, the metal identifying device and metal identifying method of the present invention are not limited to use in a disassembly-sorting line for CRT display metal parts. They can be used in any process that requires identification of the material of a CRT shadow mask, and any process that requires the identification of the metal composition of a metal member having a plurality of through-hole portions penetrating through the metal member. Instead of merely identifying the material of a shadow mask after rough disassembly of a CRT display housing and a CRT as in the above embodiments, the material can be identified in any process in which the electrical resistance value etc. of a shadow mask is measured, such as an intermediate process in a disassembly or assembly process.

Also, although the above embodiments describe exemplary cases in which there are two types of metal compositions of a test object, namely the iron material and the Invar alloy material, the metal identifying device and metal identifying method of the present invention are effective even if there are three or more types of materials to be identified. Also, types of metals other than the above, such as a non-ferrous metal material like aluminum, can be identified.

INDUSTRIAL APPLICABILITY

A metal identifying device of the present invention can be installed and used in, for example, a CRT display recycling line for disassembling and sorting shadow masks, support members therefor, and the like, and is very useful in metal resource recycling. Also, a metal identifying device of the present invention is highly applicable in a case of identifying metals in metal reprocessing processes etc., and is very useful in the protection of the global environment and the efficient use of resources.

The invention claimed is:

1. A metal identifying device comprising:
   a measurement unit that obtains a measurement value by measuring an electrical property and/or an optical property of a test object that is a plate-shaped metal member having a plurality of through-hole portions penetrating through the metal member;
   a threshold value determination unit that determines a threshold value with use of a reference value obtained by measuring the property of a metal member having a metal composition to be identified, and information indicating a ratio of the through-hole portions to a measurement area in the test object and/or information indicating a configuration of the through-hole portion; and
   a comparison/identification unit that identifies a metal composition of the test object by comparing the measurement value and the threshold value.

2. The metal identifying device of claim 1,
   wherein the measurement unit is a measurement unit that measures an electrical resistance value by two measurement probes,
   each measurement probe is constituted from a current application terminal that applies a constant current to a metal member and a voltage measurement terminal that comes into contact with a metal member and measures a potential difference, and
   the two measurement probes have been disposed so that the voltage measurement terminals thereof are positioned at a predetermined separation distance between each other.

3. The metal identifying device of claim 2,
   wherein the separation distance is 50 mm or greater.

4. The metal identifying device of claim 1,
   wherein the measurement unit includes a discharge electrode that causes the metal member to generate a discharge and an emitted light reception unit that collects and receives emitted light from the metal member that has been excited by the discharge.

5. The metal identifying device of one of claim 4,
   wherein the measurement unit includes a spectral analysis unit that generates a dispersion spectrum for light received by the reception unit.

6. The metal identifying device of claim 1,
   wherein the measurement unit includes a light source that irradiates a light beam on the metal member and a reflected light reception unit that receives reflected light from the metal member.

7. The metal identifying device of claim 6,
   wherein the measurement unit includes a collimating lens that converts irradiated light from the light source into a parallel beam.

8. The metal identifying device of one of claim 6,
   wherein the measurement unit includes an angle modification unit that, by moving the light source, modifies an angle formed between a center axis of the light beam and a surface of the metal member.

9. The metal identifying device of claim 1,
   wherein the measurement unit includes a light source that irradiates a light beam on the metal member and a luster reception unit that receives luster from the metal member.

10. The metal identifying device of claim 1, further comprising a mount unit on which the metal member has been mounted.

11. The metal identifying device of claim 10, further comprising a movement control unit that moves at least one of the mount unit and the measurement unit.

12. The metal identifying device of one of claim 1, further comprising a measurement position detection unit that detects a measurement position on the metal member.

13. The metal identifying device of one of claim 1, further comprising a through-hole portion detection unit that detects a position of a through-hole portion in the metal member.

14. The metal identifying device of one of claim 1,
    wherein the metal member is a CRT shadow mask.

15. The metal identifying device of one of claim 1,
    wherein the metal member is a metal member obtained by a recycling processing line for used electronic appliances.

16. A metal identifying method comprising the steps of:
    obtaining a measurement value by measuring an electrical property and/or an optical property of a test object that is a plate-shaped metal member having a plurality of through-hole portions penetrating through the metal member;
    determining a threshold value with use of a reference value obtained by measuring the property of a metal member having a metal composition to be identified, and information indicating a ratio of the through-hole portions to a measurement area in the test object and/or information indicating a configuration of the through-hole portion; and
    identifying a metal composition of the test object by comparing the measurement value and the threshold value.

17. The metal identifying method of claim 16, further comprising a step of sorting the metal member according to an identification result obtained in the comparing/identifying step.

18. The metal identifying method of claim 16, wherein the metal member is a metal member obtained by a recycling processing line for used electronic appliances.

* * * * *